US009309251B2

(12) United States Patent
Combs et al.

(10) Patent No.: US 9,309,251 B2
(45) Date of Patent: Apr. 12, 2016

(54) BICYCLIC AZAHETEROCYCLOBENZYLAMINES AS PI3K INHIBITORS

(71) Applicants: Incyte Corporation, Wilmington (DE); Incyte Holdings Corporation, Wilmington, DE (US)

(72) Inventors: Andrew P. Combs, Kennett Square, PA (US); Richard B. Sparks, Wilmington, DE (US); Thomas P. Maduskuie, Jr., Wilmington, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 35 days.

(21) Appl. No.: 13/854,789

(22) Filed: Apr. 1, 2013

(65) Prior Publication Data

US 2013/0261101 A1  Oct. 3, 2013

Related U.S. Application Data

(60) Provisional application No. 61/776,608, filed on Mar. 11, 2013, provisional application No. 61/619,210, filed on Apr. 2, 2012.

(51) Int. Cl.
| | | |
|---|---|---|
| A61K 31/553 | (2006.01) |
| C07D 413/06 | (2006.01) |
| C07D 413/12 | (2006.01) |
| C07D 413/14 | (2006.01) |
| C07D 487/04 | (2006.01) |
| A61K 31/519 | (2006.01) |

(52) U.S. Cl.
CPC ............ C07D 487/04 (2013.01); A61K 31/519 (2013.01); A61K 31/553 (2013.01)

(58) Field of Classification Search
CPC .. A61K 31/553; C07D 413/03; C07D 413/12; C07D 413/14
USPC ................. 514/211.05, 212.01; 540/490, 552
See application file for complete search history.

(56) References Cited

U.S. PATENT DOCUMENTS

| | | | |
|---|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential role for the p110δ phosphoinositide 3-kinase in the allergic response," Nature. 2004, 431(7011):1007-11.

Allen, et al., "Synthesis of C-6 substituted pyrazolo[1,5-a]pyridines with potent activity against herpesviruses," *Bioorganic & Medicinal Chemistry* (2006), 14(4), 944-954.

Bader, et al., "Cancer-specific mutations in PIK3CA are oncogenic in vivo," Proc Natl Acad Sci U S A. 2006, 103(5):1475-9.

Barber, et al., "PI3Kγ inhibition blocks glomerulonephritis and extends lifespan in a mouse model of systemic lupus," Nat Med. 2005, 11(9):933-5.

(Continued)

*Primary Examiner* — Brenda Coleman
(74) *Attorney, Agent, or Firm* — Fish & Richardson P.C.

(57) ABSTRACT

The present invention provides bicyclic azaheterocyclobenzylamines of Formula I:

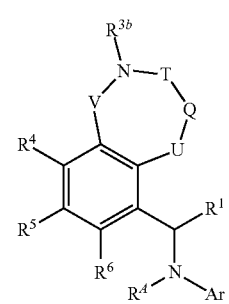

wherein the variables are defined herein, that modulate the activity of phosphoinositide 3-kinases (PI3Ks) and are useful in the treatment of diseases related to the activity of PI3Ks including, for example, inflammatory disorders, immune-based disorders, cancer, and other diseases.

29 Claims, No Drawings

(56) References Cited

U.S. PATENT DOCUMENTS

| | | |
|---|---|---|
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0281884 A1 | 11/2011 | Combs et al. |
| 2011/0312979 A1 | 12/2011 | Li et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121222 A1 | 5/2014 | Li et al. |
| 2014/0275127 A1 | 9/2014 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |

(56) References Cited

FOREIGN PATENT DOCUMENTS

| | | |
|---|---|---|
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |

OTHER PUBLICATIONS

Barragan et al., "Protein Kinases in the Regulation of Apoptosis in B-cell Chronic Lymphocytic Leukemia," *Leukemia and Lymphoma*, 2003, 44(11):1865-1870.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Berge et al., "Pharmaceutical Salts," J Pharma Sci, 1977, 66(1):1-19.

Bergman, et al., "Synthesis of indolocarbazole quinones; potent aryl hydrocarbon receptor ligands," *Tetrahedron* (2002), 58(7), 1443-1452.

Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.

Billottet, et al., "A selective inhibitor of the p110δ isoform of PI 3-kinase inhibits AML cell proliferation and survival and increases the cytotoic effects of VP16," Oncogene. 2006, 25(50):6648-59.

Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.

Blom et al., Preparative LC-MS Purification: Improved Compound Specific Method Optimization, J. Combi. Chem. 2004, 6(6), 874-883.

Boger, et al., "First and Second Generation Total Synthesis of the Teicoplanin Aglycon," JACS, 123(9), 1862-1871, 2001.

Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.

Brock et al., "Roles of Gβγ in membrane recruitment and activation of p110γ/p101 phosphoinositide 3-kinaseγ," J Cell Biol., 2003 160(1):89-99.

Brown, et al., "Small molecule inhibitors of IgE synthesis," *Bioorganic & Medicinal Chemistry Letters* (2006), 16(17), 4697-4699.

(56) References Cited

OTHER PUBLICATIONS

Camps, et al., "Blockade of PI3Kγ suppresses joint inflammation and damage in mouse models of rheumatoid arthritis," Nat Med. 2005, 11(9):936-43.
Cantley, "The Phosphoinositide 3-Kinase Pathway," Science, (2002) 296 (5573):1655-7.
Chai, et al., "Synthesis and in vitro anti-hepatitis B virus activities of some ethyl 6-bromo-5-hydroxy-1H-indole-3-carboxylates,"*Bioorganic & Medicinal Chemistry* (2006), 14(4), 911-917.
Clayton, et al., "A Crucial Role for the p110δ Subunit of Phosphatidylinositol 3-Kinase in B Cell Development and Activiation," J Exp Med. 2002, 196(6):753-63.
DeBerardinis et al., "The Biology of Cancer: Metabolic Reprogramming Fuels Cell Growth and Proliferation," Cell Metabolism, Jan. 2008, 7:11-20.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Fruman and Bismuth, "Fine Tuning the Immune Response with PI3K," *Immunological Revs.*, 2006, 228:253-272.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008), 18(15), 4368-4372.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999).
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing-Remitting Multiple Sclerosis," The New England Journal of Medicine, 358(7):676-688, 2008.

Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.
Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.
Huang et al., "Synthesis and bioassay of a fluorine-containing cytokinin, N6-pentafluoro-benzyladenosine," *Youji Huaxue* (1988), 8(2), 147-8 (with English abstract).
Ihle et al., "Inhibitors of phosphatidylinositol-3-kinase in cancer therapy", *Molecular Aspects of Medicine*, 31(2):135-144, 2010.
Irie, et al., "Discovery of selective and nonpeptidic cathepsin S inhibitors," *Bioorganic & Medicinal Chemistry Letters* (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-riboftiranoside," *Tetrahedron Letters* (1998), 39(26), 4695-4696.
Itaya, et al., "Synthesis and structure of the marine ascidian 8-oxoadenine aplidiamine," *Chemical & Pharmaceutical Bulletin* (1999), 47(9), 1297-1300.
Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.
Jager, et al., "Molecular recognition analyzed by EPR, ENDOR, and NMR spectroscopy," *Angewandte Chemie*, International Edition in English (1996), 35(16), 1815-1818.
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian *Aplidiopsis* sp.," *Tetrahedron Letters* (1997), 38(6), 941-944.
Kang, et al., "Phosphtidylinositol 3-kinase mutations identified in human cancer are oncogenic," Proc Natl Acad Sci U S A. 2005, 102(3):802-7.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.
Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," *Bioorganic & Medicinal Chemistry* (1997), 5(3), 507-514.
Kong and Yamori, "Advances in Development of Phosphatidylinositol 3-Kinase Inhibitors," Current Medicinal Chemistry, 16:2839-2854, 2009.

(56) References Cited

OTHER PUBLICATIONS

Kuduk et al., "Heterocyclic fused pyridone carboxylic acid M1 positive allosteric modulators," *Bioorganic & Medicinal Chemistry Letters* (2010), 20(8), 2533-2537.

Kung et al., "Characterization of a Murine Model of Allergic Pulmonary Inflammation," Int. Arch. Allergy Immunol., (abstract), 105(1):83-90, 1994.

Kurimoto, et al., "Synthesis and Biological Evaluation of 8-Oxoadenine Derivatives as Toll-like Receptor 7 Agonists Introducing the Antedrug Concept", *Journal of Medicinal Chemistry* (2010), 53(7),2964-2972.

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al., "Inhibition of phosphoinositide 3-kinase δ attenuates allergic airway inflammation and hyperresponsiveness in murine asthma model," FASEB J. 2006 20(3):455-65.

Li et al., "Design, synthesis and antitumor activities of novel 4-anilino-5H-pyridazino[4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Li, et al., "Optimization of the heterocyclic core of the quinazolinone-derived CXCR3 antagonists," *Bioorganic & Medicinal Chemistry Letters* (2008), 18(2), 688-693.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) 2002), 60, No pp. given CODEN: ORHNBA URL: http://www3.interscience.wiley.com/cgi-bin/mrwhome/107610747/HOME.

Lucas, et al., "Rauwolfia alkaloids. XXXI. The synthesis and activity of some reserpine analogs," *Journal of the American Chemical Society* (1959), 81, 1928-32.

Ma, et al., "Two new constituents from Artemisia capillaris Thunb", Molecules (2008), 13(2), 267-271.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McLean, et al., "Discovery of covalent inhibitors for MIF tautomerase via cocrystal structures with phantom hits from virtual screening ," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

Meijer et al., "Treatment of primary Sjögren syndrome with rituximab: extended follow-up, safety and efficacy of retreatment," Ann. Rheum. Dis., 68(2):284-285, 2009.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society, Perkin Transactions 1* (2001), (18), 2213-2216.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+ Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., Generation and behavior of naphthoyloxyl radicals in photocleavage of 1-(naphthoyloxy)-2-pyridones, *Chemistry Letters* (2001), (10), 1064-1065.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Nettekoven, M., "A combinatorial approach towards 2-acyl-3-amino-indole derivatives," *Tetrahedron Letters* (2000), 41(43), 8251-8254.

Norman, P., "Selective PI3Kδ inhibitors , a review of the patent literature", Expert Opinion on Therapeutic Patents, Informa Healthcare, 21(11):1773-1790, 2011.

Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.

Okkenhaug, et al., "Impaired B and T Cell Antigen Receptor Signaling in p110δ PI 3-Kinase Mutant Mice," Science, 2002, 297(5583):1031-4).

Park et al., "Phosphoinositide 3-kinase δ inhibitor as a novel therapeutic agent in asthma," Respirology, 13:764-771, 2008.

Phillips, et al., "The reaction of anils with 8-quinolinol," *Journal of Organic Chemistry* (1954), 19, 907-9 CODEN: JOCEAH; ISSN: 0022-3263.

Pinedo and Slamon, "Translational Research: The Role of VEGF in Tumor Angiogenesis," The Oncologist, 5(1):1-2, 2000.

Platts, et al., "A concise synthesis of HIV integrase inhibitors bearing the dipyridone acid motif," *Tetrahedron Letters* (2011), 52(4), 512-514.

Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).

Prezent, et al., STN Abstract, Accession No. 2004:358794, "Boron chelates as intermediates in the synthesis of new functionalized pyridines and pyrimidines from α, α-dioxoketene aminals," *Boron Chemistry at the Beginning of the 21st Century, [Proceedings of the International Conference on the Chemistry of Boron]*, 11th, Moscow, Russian Federation, Jul. 28-Aug. 1, 2002 (2003), Meeting Date 2002,

(56) References Cited

OTHER PUBLICATIONS 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ0 in inflammatory arthritis and tissue localization of neutrophils," Eur. J. Immunol , 2008, 38(5):1215-24.
Reich, et al., "Preparation of a,b-unsaturated carbonyl compounds and nitriles by selenoxide elimination ," Organic Reactions (Hoboken, NJ, United States) (1993), 44, No pp. given.
Remington's Pharmaceutical Sciences, 17th ed., Mack Publishing Company, Easton, Pa., 1985, p. 1418.
Ringshausen et al., "Constitutively Actived phosphatidylinositol-3-kinase (PI-3K) is involved in the defect of apoptosis is B-CLL: associate with protein kinase C delta," Blood, 2002, 100:3741-3748.
Roxas-Duncan, et al., "Identification and biochemical characterization of small-molecule inhibitors of Clostridium botulinum neurotoxin serotype A," Antimicrobial Agents and Chemotherapy (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," Science of Synthesis (2004), 16, 1155-1267.
Samuels, et al., "High Frequency of Mutations of the PIK3CA Gene in Human Cancers," Science, 2004, 304(5670):554.
Samuels and Ericson, "Oncogenic PI3K and its role in cancer," Curr Opin Oncol., 2006,18(1):77-82.
Sasaki, et al., "Function of PI3Kγ in Thymocyte Development, T Cell Activation, and Neutrophil Migration," Science, 2000, 287(5455):1040-6.
Saxena, et al., "Pharmacophore-based virtual screening and docking studies on Hsp90 inhibitors", SAR and QSAR in Environmental Research (2010), 21(5-6), 445-462.
Schell, et al., "Versatile Solid-Phase Synthesis of Trisubstituted 1H-Pyrido[2,3-d]pyrimidin-4-ones and Related Heterocycles," Journal of Combinatorial Chemistry (2005), 7(1), 96-98.
Sen, et al., "Reaction of aldehydes and amines with 8-hydroxyquinaldine and 8-quinolinol. II," Journal of the Indian Chemical Society (1960), 37, 640-2.
Shi, et al., "Synthesis and preliminary cytotoxic evaluation of substituted indoles as potential anticancer agents," Chinese Chemical Letters (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Singh et al., "Application of Nazarov cyclization to access [6-5-6] and [6-5-5]tricyclic core embedded new heterocycles: an easy entry to structures related to Taiwaniaquinoids," Organic & Biomolecular Chemistry (2009), 7(9), 1858-1867, CODEN: OBCRAK; ISSN: 1477-0520.
Steliou, et al., "Does diatomic sulfur(S2) react as a free species?", Journal of the American Chemical Society (1992), 114(4), 1456-62.
Stüve et al., "Long-term B-Lymphocyte Depletion With Rituximab in Patients With Relapsing-Remitting Multiple Sclerosis," Arch. Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," Bioorganic & Medicinal Chemistry (2009), 17(5), 1938-1947.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," Acta Crystallographica, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Xu et al., "Activation of the PI3K/AKT/mTOR pathway in diffuse large B cell lymphoma: clinical significance and inhibitory effect of rituximab," Ann Hematol., 2013 92:1351-1358.
Yaguchi et al., "Antitumor Activity of ZSTK474, a new Phosphatidinylinositol 3-Kinase Inhibitor," J Natl. Cancer Inst., 2006, 98(8):545-556.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yanni, et al., "Synthesis and biological activity of some 7-substituted aminomethyl-8-hydroxyquinoline-5-sulfonic acids," Indian Journal of Chemistry, Section B: Organic Chemistry Including Medicinal Chemistry (1982), 21B(7), 705-6.
Yanni, A. S., "Synthesis of some new 5-iodo-7-substituted-aminomethyl-8-hydroxyquinoline," Revue Roumaine de Chimie (1994), 39(7), 833-6 CODEN: RRCHAX; ISSN: 0035-3930.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," Archives of Pharmacal Research (2008), 31(2), 142-147 CODEN: APHRDQ; ISSN: 0253-6269.
Yoshida, et al., "MexAB-OprM specific efflux pump inhibitors in Pseudomonas aeruginosa. Part 5: Carbon-substituted analogues at the C-2 position," Bioorganic & Medicinal Chemistry (2006), 14(6), 1993-2004.
Zhang et al., "Advances in preclinical small molecules for the treatment of NSCLC", Expert Opinion on Therapeutic Patents, 19(6):731-751, 2009.
Zhao, et al., "Synthesis and in vitro anti-hepatitis B virus activities of some ethyl 5-hydroxy-1H-indole-3-carboxylates," Bioorganic & Medicinal Chemistry (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).

(56) References Cited

OTHER PUBLICATIONS

International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
"Angiogenesis" Merriam-Webster.com. Merriam-Webster, n.d. Web Jun. 16, 2014, www.merriam-webster.com/dictionary/angiogenesis, 3 pages.
"Arthritis: MedlinePlus Medical Encyclopedica," 2014, p. 1-5, accessed online Oct. 7, 2014; http://www.nlm.nih.gove/medlineplus/ency/article/001243.htm.
"Autoimmune disorders: MedlinePlus Medical Encyclopedia," 2013, p. 1-4, accessed online Oct. 7, 2014; http://www.nlm.nih.gov/medlineplus/ency/article/000816.htm.
Baek et al., "Complete remission induced by rituximab in refractory, seronegative, muscle-specific, kinase-positive myasthenia gravis," J Neurol Neurosurg Psychiatry, 2007, 78(7):771.
Ball, "PI3K inhibitors as potential therapeutics for autoimmune disease," Drug Discovery Today, 2014, pp. 1195-119.
Cannon, Burger's Medicinal Chemistry and Drug Discovery, Fifth Edition, vol. 1 Principles and Practice, Wiley-Interscience 1995, Ch. 19, pp. 783-803, 784.
Collins et al., "Rituximab treatment of fibrillary glomerulonephritis," Am J Kidney Dis., 2008, 52(6):1158-62.
Crabbe, "The PI3K inhibitor arsenal: choose your weapon!" Trends Biochem Sci., 2007, 32(10):450-56.
Devauchelle-Pensec, "Treatment of Primary Sjogren Syndrome with Rituximab," Annal Internal Med., 2014, 160:233-242.
Lipsky, "Systemic lupus erythematosus: an autoimmune disease of B cell hyperactivity," Nat Immunol., 2001, 2(9):764-6.
Liu et al., "Inhibition of the mitotic kinesin Eg5 up-regulates Hsp70 through the phosphatidylinositol 3-kinase/Akt pathway in multiple myeloma cells," J Biol Chem., 2006 281(26):18090-18097.
MedicineNet.com' [online]. "Definition of Cancer," Sep. 18, 2004, retrieved on Sep. 16, 2005. Retrieved from the Internet: http://www.medterms.com, 1 page.
Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.
Segarra et al., "Successful treatment of membranous glomerulonephritis with rituximab in calcineurin inhibitor-dependent patients," Clin J Am Soc Nephrol., 2009, 4(6):1083-8.
Schafer and Kolkhof, "Failure is an option: learning from unsuccessful proof-of-concept trials," Drug Discovery Today, Nov. 2008, 13(21/22):913-916.
WebMD. Lung Disease & Respiratory Health Center: Lung Disease Overview, May 23, 2014, www.webmd.com/lung/lung-diseases-overview, 3 pages.
WebMD. Lung Disease & Respiratory Health Center: ARDS, May 21, 2014, www.webmd.com/lung/ards-acute-respiratory-distress-syndrome?page=2, 4 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
WebMD. Bladder Cancer Health Center: Bladder Cancer-Prevention, Apr. 30, 2013, www.webmd.com/cancer/bladder-cancer/bladder-cancer-prevention, 1 page.
WebMD. Arthritis Health Center: What is Inflammation? Jul. 6, 2012, www.webmd.com/arthritis/about-inflammation?page=2, 4 pages.
International Preliminary Report on Patentability for PCT/US2012/053398, issued Mar. 4, 2014 (6 pgs.).
Office Action in CO Application No. 11-179.464, received on Mar. 14, 2014, 17 pages.
Office Action in JP Application No. 2012-518563, dated Jul. 8, 2014, 6 pages (with English translation).
"A to Z List of Cancers," National Cancer Institute (http://www.cancer.gov/) (Downloaded May 29, 2014), 22 pages.
Bhatia and Rose, "Autoimmunity and autoimmune disease," Principles of Med Biol., 1996, 6:239-263, 244.
Brachmann et al., "PI3K and mTOR inhibitors—a new generation of targeted anticancer agents," Current Opinion Cell Biol., 2009, 21:194-198.
Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941.
Delmas and Meunier, "The Management of Paget's Disease of Bone," N Engl J Med., 1997, 336:558-566.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fine et al., "Neoplasms of the Central Nervous System," Cancer Principles Practice Oncol., 2005, 2:1834-1887.
Ghigo et al., "PI3K inhibition in inflammation: Toward tailored therapies for specific diseases," BioEssays, 2010, 32:185-196.
Harley, "Medical Management of Actue Renal Failure," Renal Failure Replacement Therapies, 2008, pp. 26-32.
Hayter and Cook, "Updated assessment of the prevalence, spectrum and case definition of autoimmune disease," Autoimmunity Reviews, 2012, 11:754-765.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kim et al., "A signaling network in Phenylephrine-Induced Benign Prostatic Hyperplasia," Endocrinology, 2009, 150:3576-3583.

(56) References Cited

OTHER PUBLICATIONS

Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.

Kong and Yamori, "Phosphatidylinositol 3-kinase inhibitors: promising drug candidates for cancer theraphy," Cancer Sci., 2008, 9:1734-1740.

Kuster (ed), Kinase Inhibitors: Methods and Protocols Methods in Molecular Biology, 2012, 795:1-44.

Liu et al., "mTOR mediated anti-cancer drug discovery," Drug Discovery Today: Therapeutic Strategies, 2009, 6:47-55.

Luo et al., "Principles of Cancer Therapy: Oncogene and Non-oncogene Addiction," Cell, 2009, 36:823-837.

Martelli et al., "Targeting the PI3K/AKT/mTOR signaling network in acute myelogenous leukemia," Expert Opin Investig Drugs. Sep. 2009;18(9):1333-49.

McDermott and Settleman, "Personalized Cancer Theraphy with Selective Kinase Inhibitors: An Emerging Paradigm in Medical Oncology," J Clinical Oncol., 2009, 27:5650-5659.

medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&__suid=14297429843880910545130428968 4>. 10 pages.

Sawyers, "The cancer biomarker problem," Nature, 2008, 452:548-552.

Silverman, R. B., "The organic Chemistry of Drugs Design and Drug Action." Elsevier. Northwestern University. Second Edition. Evanstons Illinois. 2004. p. 29 and table 2.2 *too voluminous to cite*.

Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.

Yamada et al., "Alpha-1 Adrenoceptors in Human Prostate: Characterization and Alteration in Benign Prostatic Hypertrophy," J Pharmacol Experimental Therapeutics, 1987, 242(1):326-330.

Yoon et al., "Impact of fluoroquinolones on the diagnosis of pulmonary tuberculosis initially treated as bacterial pneumonia," Int'l J Tuberculosis and Lung Dis, 2005, 9:1215-1219.

Zhao and Vogt, "Class I PI3K in oncogenic cellular transformation," Oncogene, 2008, 27:5486-5496.

Apsel et al., "Targeted polypharmacology: discovery of dual inhibitors of tyrosine and phosphoinositide kinases," Nat. Chem. Biol., 2008, 4(11): 691-699.

Bendell, J.C., "Phase I, dose-escalation study of BKM120, an oral pan-Class I PI3K inhibitor, in patients with advanced solid tumors," Journal of Clincial Oncology (2011): JCO-2011.

Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.

Chen, X., "Targeting oxidative stress in embryonal rhabdomyosarcoma," Cancer cell 24.6 (2013): 710-724.

Umar, A., "Future directions in cancer prevention," Nature Reviews Cancer, 12.12 (2012): 835-848.

Wallin, J.J., "GDC-0980 is a novel class I PI3K/mTOR kinase inhibitor with robust activity in cancer models driven by the PI3K pathway," Molecular cancer therapeutics 10.12 (2011): 2426-2436.

Yuan, T.L., "PI3K pathway alterations in cancer: variations on a theme," Oncogene, 2008, 27.41: 5497-551.

Office Action in JP Application No. 2013-546274, dated Sep. 15, 2015, 7 pages (with English Translation).

BICYCLIC AZAHETEROCYCLOBENZYLAMINES AS PI3K INHIBITORS

This application claims the benefit of priority of U.S. Provisional Application 61/619,210, filed Apr. 2, 2012, and U.S. Provisional Application 61/776,608, filed Mar. 11, 2013, each of which is incorporated herein by reference in its entirety.

FIELD OF THE INVENTION

The present invention provides bicyclic azaheterocyclobenzylamine derivatives, for example, pyrazolopyrimidines, that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol. Chem., 2002, 277(44):41556-62) whereas PI3Kγ associates with two regulatory subunits (p101 and p84) and its activation is driven by the activation of G-protein-coupled receptors (Brock, et al., J. Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4): 194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat. Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat. Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

B cell proliferation has shown to play a major role in the development of inflammatory autoimmune diseases (Puri, Frontiers in Immunology (2012), 3(256), 1-16; Walsh, Kidney International (2007) 72, 676-682). For example, B cells support T-cell autoreactivity, an important component of inflammatory autoimmune diseases. Once activated and matured, B cells can traffic to sites of inflammation and recruit inflammatory cells or differentiate to plasmablasts. Thus, activity of B-cells can be affected by targeting B-cell stimulatory cytokines, B-cell surface receptors, or via B-cell depletion. Rituximab—an IgG1 κ mouse/human chimeric monoclonal antibody directed against the B-cell surface receptor CD20—has been shown to deplete CD20+ B cells. Use of rituximab has been shown to have efficacy in treating idiopathic thrombocytopenic purpura, autoimmune hemolytic anemia, or vasculitis. For example, treatment with rituximab resulted in remission of the disease in patients suffering from anti-neutrophil cytoplasm antibody associated (ANCA) systemic vasculitis (AASV) with demonstrated peripheral B-cell depletion (Walsh, 2007; Lovric, Nephrol Dial Transplant (2009) 24: 179-185). Similarly, a complete response was reported in one-third to two-thirds of patients having mixed cryoglobulinemia vasculitis after treatment with rituximab, including patients who presented with a severe form of vasculitis that was resistant or intolerant to other treatments (Cacoub, Ann Rheum Dis 2008; 67:283-287). Similarly, rituximab has been shown to have efficacy in treating patients with idiopathic thrombocytopenic purpura (or immune thrombocytopenic purpura) (Garvey, British Journal of Haematology, (2008) 141, 149-169; Godeau, Blood (2008), 112(4), 999-1004; Medeo, European Journal of Haematology, (2008) 81, 165-169) and autoimmune hemolytic anemia (Garvey, British Journal of Haematology, (2008) 141, 149-169).

PI3Kδ signaling has been tied to B cell survival, migration, and activation (Puri, *Frontiers in Immunology*, 2012, 3(256), 1-16, at pages 1-5; and Clayton, *J Exp Med*, 2002, 196(6): 753-63). For example, PI3Kδ is required for antigen-dependent B-cell activation driven by B cell receptor. By blocking B-cell adhesion, survival, activation, and proliferation, PI3Kδ inhibition can impair the ability of B cells to activate T cells, preventing their activation and reducing secreation of autoantibodies and pro-inflammatory cytokines. Hence, by their ability to inhibit B cell activation, PI3Kδ inhibitors would be expected to treat B cell mediated diseases that were treatable by similar methods such as B cell depletion by rituximab. Indeed, PI3Kδ inhibitors have been shown to be useful mouse models of various autoimmune diseases that are also treatable by rituximab such as arthritis (Puri (2012)).

Further, innate-like B cells, which are linked to autoimmunity are sensitive to PI3Kδ activity, as MZ and B-1 cells are nearly absent in mice lacking the p110δ gene (Puri (2012). PI3Kδ inhibitors can reduce trafficking of and activation of MZ and B-1 cells, which are implicated in autoimmune diseases.

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA, 2005, 102(3): 802-7; Bader, et al., Proc Natl Acad Sci USA. 2006, 103(5): 1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3): 1063-6) and inhibitors of PI3Kδ can prevent the growth of leukemic cells (Billottet, et al., Oncogene, 2006, 25(50):6648-59). Elevated expression of PI3Kγ is seen in chronic myeloid leukemia (Hickey, et al., J Biol. Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44): 5083-90; Mizoguchi, et al., Brain Pathol. 2004, 14(4):372-7; Knobbe, et al., Neuropathol Appl Neurobiol. 2005, 31(5): 486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and others.

SUMMARY

The present invention provides, inter alia, a compound of Formula I:

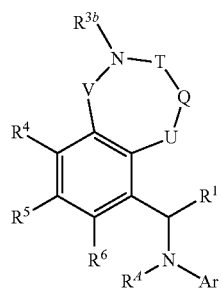

I or a pharmaceutically acceptable salt thereof, wherein the variables are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of the invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

The present invention provides, inter alia, a compound of Formula I:

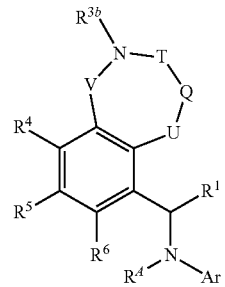

I or a pharmaceutically acceptable salt thereof, wherein:
V is C(=O), S(=O)$_2$, CH$_2$, CHR$^{3c}$, and CR$^{3c}$R$^{3c}$;
T is C(=O), S(=O)$_2$, CH$_2$, CHR$^{3a}$, and CR$^{3a}$R$^{3a}$;
Q is C(=O), S(=O)$_2$, (CH$_2$)$_n$, (CHR$^{3a}$)$_n$, and (CR$^{3a}$R$^{3a}$)$_n$;
wherein n is 0, 1, or 2;
U is O or NR$^{3d}$;
provided that when T is C(=O) or S(=O)$_2$, then Q is (CH$_2$)$_n$, (CHR$^{3a}$)$_n$, or (CR$^{3a}$R$^{3a}$)$_n$;
further provided that when Q is C(=O) or S(=O)$_2$, then T is CH$_2$, CHR$^{3a}$, or CR$^{3a}$R$^{3a}$, and U is NR$^{3d}$;
R$^A$ is H or C$_{1-3}$ alkyl;

Ar is

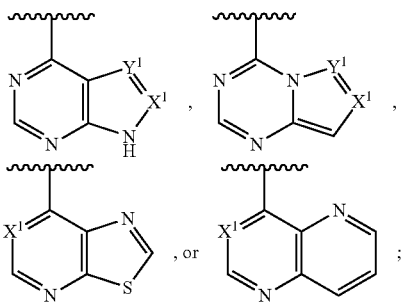

$X^1$ is CH or N;
$Y^1$ is CH or N;
or alternatively, $R^A$ and Ar, together with the N to which they are attached, combine to form a moiety of formula:

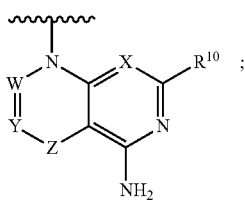

X is $CR^9$ or N;
W is $CR^7$ or N;
Y is $CR^8$, $CR^{8a}$, or N;
Z is a bond or $C(=O)$;
provided that —W=Y—Z— is —$CR^7$=$CR^8$—, —N=$CR^8$—, —$CR^7$=$CR^{8a}$—C(=O)—, —N=$CR^{8a}$—C(=O)—, or —$CR^7$=N—C(=O)—;
$R^1$ is $C_{1-3}$ alkyl;
each $R^{3a}$ is independently selected from $C_{1-6}$ alkyl, $C_{2-6}$ alkenyl, $C_{2-6}$ alkynyl, $C_{1-6}$ haloalkyl, and $Cy^1$; wherein said $C_{1-6}$ alkyl, $C_{2-6}$ alkenyl, and $C_{2-6}$ alkynyl are each optionally substituted with 1, 2, or 3 independently selected $R^{11}$ groups;
$R^{3b}$ is H, Cy, —($C_{1-3}$ alkylene)-Cy, $C_{1-6}$ alkyl, $C_{2-6}$ alkenyl, $C_{2-6}$ alkynyl, $C_{1-6}$ haloalkyl, $C(=O)R^b$, $C(=O)NR^cR^d$, $C(=O)OR^a$, $C(=NR^e)R^b$, $C(=NR^e)NR^cR^d$, $S(=O)_2R^b$, or $S(=O)_2NR^cR^d$; wherein said $C_{1-6}$ alkyl, $C_{2-6}$ alkenyl, and $C_{2-6}$ alkynyl are each optionally substituted by 1, 2, 3, or 4 independently selected $R^{13b}$ groups;
each $R^{3c}$ is independently selected from $C_{1-4}$ alkyl, $C_{1-4}$ haloalkyl, $C_{1-4}$ alkoxy-$C_{1-4}$ alkyl, and $C_{1-4}$ haloalkoxy-$C_{1-4}$ alkyl;
$R^{3d}$ is H, $C_{1-4}$ alkyl, $C_{1-4}$ haloalkyl, $C_{1-4}$ alkoxy-$C_{1-4}$ alkyl, or $C_{1-4}$ haloalkoxy-$C_{1-4}$ alkyl;
$R^4$ is H, halo, OH, CN, $C_{1-4}$ alkyl, $C_{1-4}$ haloalkyl, $C_{1-4}$ alkoxy, or $C_{1-4}$ haloalkoxy;
$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;
$R^6$ is H, halo, OH, CN, $C_{1-4}$ alkyl, $C_{1-4}$ haloalkyl, $C_{1-4}$ alkoxy, or $C_{1-4}$ haloalkoxy;
$R^7$ is H or $C_{1-4}$ alkyl;
$R^8$ is H, halo, —OH, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $C(=NR^e)R^{b2}$, $C(=NR^e)NR^{c2}R^{d2}$, $NR^{c2}C(=NR^e)NR^{c2}R^{d2}$, $NR^{c2}S(=O)R^{b2}$, $NR^{c2}S(=O)_2NR^{c2}R^{d2}$, $S(=O)R^{b2}$, $S(=O)_2R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^{8a}$ is H, halo, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $C(=O)R^{b2}$, $C(=O)NR^{c2}R^{d2}$, $C(=O)OR^{a2}$; $NR^{c2}R^{d2}$; $NR^{c2}C(=O)R^{b2}$; $NR^{c2}C(=O)OR^{b2}$, $NR^{c2}C(=O)NR^{c2}R^{d2}$, $NR^{c2}S(=O)R^{b2}$, $NR^{c2}S(=O)_2NR^{c2}R^{d2}$; $S(=O)R^{b2}$, $S(=O)_2R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^9$ is H, halo, OH, CN, $C_{1-4}$ alkyl, $C_{1-4}$ haloalkyl, $C_{1-4}$ alkoxy, or $C_{1-4}$ haloalkoxy;
$R^{10}$ is H or $C_{1-4}$ alkyl;
each $R^{11}$ is independently selected from halo, OH, $NO_2$, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, amino sulfonyl, $C_{1-3}$ alkylaminosulfonyl, di($C_{1-3}$ alkyl)aminosulfonyl, amino sulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;
each $R^{13b}$ is independently selected from $Cy^1$, —($C_{1-3}$ alkylene)-$Cy^1$, halo, CN, $NO_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$, $S(=O)R^{b1}$, $S(=O)_2R^{b1}$, and $S(=O)_2NR^{c1}R^{d1}$; wherein said $C_{1-6}$ alkyl, $C_{2-6}$ alkenyl, $C_{2-6}$ alkynyl are each optionally substituted with 1, 2, or 3 independently selected $R^{11}$ groups;
each Cy is independently selected from $C_{3-7}$ cycloalkyl, 4-10 membered heterocycloalkyl, phenyl, naphthyl, and 5-10 membered heteroaryl, wherein said $C_{3-7}$ cycloalkyl, 4-10 membered heterocycloalkyl, phenyl, naphthyl, and 5-10 membered heteroaryl are optionally substituted with 1, 2, 3, or 4 independently selected $R^{13b}$ groups;
each $R^a$, $R^c$, and $R^d$ is independently selected from H, $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups;
each $R^b$ is independently selected from $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups; or
alternatively, $R^c$ and $R^d$ together with the N atom to which they are attached form a 4-, 5-, 6-, or 7 membered heterocycloalkyl group, which is optionally substituted with 1, 2, or 3 independently selected $R^{13b}$ groups;
each $R^e$ is independently selected from H, CN, OH, $C_{1-4}$ alkyl, and $C_{1-4}$ alkoxy;
each $Cy^1$ is independently selected from $C_{3-7}$ cycloalkyl, 4-7 membered heterocycloalkyl, phenyl, and 5-6 membered heteroaryl, wherein said $C_{3-7}$ cycloalkyl, 4-7 membered heterocycloalkyl, phenyl, and 5-6 membered heteroaryl are optionally substituted with 1, 2, 3, or 4 independently selected $R^{11}$ groups;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; or alternatively, $R^{c1}$ and $R^{d1}$ together with the N atom to which they are attached form a 4-, 5-, 6-, or 7 membered heterocycloalkyl group, which is optionally substituted with —OH or $C_{1-3}$ alkyl;

each $Cy^2$ is independently selected from $C_{3-7}$ cycloalkyl, 4-7 membered heterocycloalkyl, phenyl, 5-6 membered heteroaryl, and 9-10-membered bicyclic heteroaryl, each of which is optionally substituted with 1, 2, 3, or 4 independently selected $R^{11}$ groups;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; and each $R^{b2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; or alternatively, $R^{c2}$ and $R^{d2}$ together with the N atom to which they are attached form a 4-, 5-, 6-, or 7 membered heterocycloalkyl group, which is optionally substituted with —OH or $C_{1-3}$ alkyl.

The present invention further provides a compound of Formula I:

I or a pharmaceutically acceptable salt thereof, wherein:
V is C(=O), S(=O)$_2$, CH$_2$, CHR$^{3c}$, and CR$^{3c}$R$^{3c}$;
T is C(=O), S(=O)$_2$, CH$_2$, CHR$^{3a}$, and CR$^{3a}$R$^{3a}$;
Q is C(=O), S(=O)$_2$, (CH$_2$)$_n$, (CHR$^{3a}$)$_n$, and (CR$^{3a}$R$^{3a}$)$_n$; wherein n is 0, 1, or 2;
U is O or NR$^{3d}$;

provided that when T is C(=O) or S(=O)$_2$, then Q is (CH$_2$)$_n$, (CHR$^{3a}$)$_n$, or (CR$^{3a}$R$^{3a}$)$_n$;
further provided that when Q is C(=O) or S(=O)$_2$, then T is CH$_2$, CHR$^{3a}$, or CR$^{3a}$R$^{3a}$, and U is NR$^{3d}$;
$R^A$ is H or $C_{1-3}$ alkyl;
Ar is $X^1$ is CH or N;
$Y^1$ is CH or N;
or alternatively, $R^A$ and Ar, together with the N to which they are attached, combine to form a moiety of formula:

X is CR$^9$ or N;
W is CR$^7$ or N;
Y is CR$^8$, CR$^{8a}$, or N;
Z is a bond or C(=O);
provided that —W=Y—Z— is —CR$^7$=CR$^8$—, —N=CR$^8$—, —CR$^7$=CR$^{8a}$—C(=O)—, —N=CR$^{8a}$—C(=O)—, or —CR$^7$=N—C(=O)—;
$R^1$ is $C_{1-3}$ alkyl;
each $R^{3a}$ is independently selected from $C_{1-6}$ alkyl, $C_{2-6}$ alkenyl, $C_{2-6}$ alkynyl, $C_{1-6}$ haloalkyl, and Cy$^1$; wherein said $C_{1-6}$ alkyl, $C_{2-6}$ alkenyl, and $C_{2-6}$ alkynyl are each optionally substituted with 1, 2, or 3 independently selected $R^{11}$ groups;
$R^{3b}$ is H, Cy, —(C$_{1-3}$ alkylene)-Cy, $C_{1-6}$ alkyl, $C_{2-6}$ alkenyl, $C_{2-6}$ alkynyl, $C_{1-6}$ haloalkyl, C(=O)R$^b$, C(=O)NR$^c$R$^d$, C(=O)OR$^a$, C(=NR$^e$)R$^b$, C(=NR$^e$)NR$^c$R$^d$, S(=O)$_2$R$^b$, or S(=O)$_2$NR$^c$R$^d$; wherein said $C_{1-6}$ alkyl, $C_{2-6}$ alkenyl, and $C_{2-6}$ alkynyl are each optionally substituted by 1, 2, 3, or 4 independently selected $R^{13b}$ groups;
each $R^{3c}$ is independently selected from $C_{1-4}$ alkyl, $C_{1-4}$ haloalkyl, $C_{1-4}$ alkoxy-$C_{1-4}$ alkyl, and $C_{1-4}$ haloalkoxy-$C_{1-4}$ alkyl;
$R^{3d}$ is H, $C_{1-4}$ alkyl, $C_{1-4}$ haloalkyl, $C_{1-4}$ alkoxy-$C_{1-4}$ alkyl, or $C_{1-4}$ haloalkoxy-$C_{1-4}$ alkyl;
$R^4$ is H, halo, OH, CN, $C_{1-4}$ alkyl, $C_{1-4}$ haloalkyl, $C_{1-4}$ alkoxy, or $C_{1-4}$ haloalkoxy;
$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;
$R^6$ is H, halo, OH, CN, $C_{1-4}$ alkyl, $C_{1-4}$ haloalkyl, $C_{1-4}$ alkoxy, or $C_{1-4}$ haloalkoxy;
$R^7$ is H or $C_{1-4}$ alkyl;
$R^8$ is H, halo, —OH, —CN, $C_{1-6}$ alkyl, $C_{2-6}$ alkenyl, $C_{2-6}$ alkynyl, $C_{1-6}$ haloalkyl, Cy$^2$, —(C$_{1-3}$ alkylene)-Cy$^2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, NR$^{c2}$C(=O)R$^{b2}$, NR$^{c2}$C(=O)OR$^{b2}$, NR$^{c2}$C(=O)NR$^{c2}$R$^{d2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$S(=O)R$^{b2}$, NR$^{c2}$S(=O)$_2$NR$^{c2}$R$^{d2}$, S(=O)R$^{b2}$, S(=O)$_2$R$^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;

$R^{8a}$ is H, halo, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $C(=O)R^{b2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)R^{b2}$, $NR^{c2}S(=O)_2NR^{c2}R^{d2}$, $S(=O)R^{b2}$, $S(=O)_2R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;

$R^9$ is H, halo, OH, CN, $C_{1-4}$ alkyl, $C_{1-4}$ haloalkyl, $C_{1-4}$ alkoxy, or $C_{1-4}$ haloalkoxy;

$R^{10}$ is H or $C_{1-4}$ alkyl;

each $R^{11}$ is independently selected from halo, OH, $NO_2$, CN, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino;

each $R^{13b}$ is independently selected from $Cy^1$, —($C_{1-3}$ alkylene)-$Cy^1$, halo, CN, $NO_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$, $S(=O)R^{b1}$, $S(=O)_2R^{b1}$, and $S(=O)_2NR^{c1}R^{d1}$; wherein said $C_{1-6}$ alkyl, $C_{2-6}$ alkenyl, $C_{2-6}$ alkynyl are each optionally substituted with 1, 2, or 3 independently selected $R^{11}$ groups;

each Cy is independently selected from $C_{3-7}$ cycloalkyl, 4-10 membered heterocycloalkyl, phenyl, naphthyl, and 5-10 membered heteroaryl, wherein said $C_{3-7}$ cycloalkyl, 4-10 membered heterocycloalkyl, phenyl, naphthyl, and 5-10 membered heteroaryl are optionally substituted with 1, 2, 3, or 4 independently selected $R^{13b}$ groups;

each $R^a$, $R^c$, and $R^d$ is independently selected from H, $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups;

each $R^b$ is independently selected from $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups; or alternatively, $R^c$ and $R^d$ together with the N atom to which they are attached form a 4-, 5-, 6-, or 7 membered heterocycloalkyl group, which is optionally substituted with 1, 2, or 3 independently selected $R^{13b}$ groups;

each $R^e$ is independently selected from H, CN, OH, $C_{1-4}$ alkyl, and $C_{1-4}$ alkoxy;

each $Cy^1$ is independently selected from $C_{3-7}$ cycloalkyl, 4-7 membered heterocycloalkyl, phenyl, and 5-6 membered heteroaryl, wherein said $C_{3-7}$ cycloalkyl, 4-7 membered heterocycloalkyl, phenyl, and 5-6 membered heteroaryl are optionally substituted with 1, 2, 3, or 4 independently selected $R^{11}$ groups;

each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; or alternatively, $R^{c1}$ and $R^{d1}$ together with the N atom to which they are attached form a 4-, 5-, 6-, or 7 membered heterocycloalkyl group, which is optionally substituted with —OH or $C_{1-3}$ alkyl;

each $Cy^2$ is independently selected from $C_{3-7}$ cycloalkyl, 4-7 membered heterocycloalkyl, phenyl, 5-6 membered heteroaryl, and 9-10-membered bicyclic heteroaryl, each of which is optionally substituted with 1, 2, 3, or 4 independently selected $R^{11}$ groups;

each $R^{a2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; and each $R^{b2}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; or alternatively, $R^{c2}$ and $R^{d2}$ together with the N atom to which they are attached form a 4-, 5-, 6-, or 7 membered heterocycloalkyl group, which is optionally substituted with —OH or $C_{1-3}$ alkyl.

In some embodiments, V is $C(=O)$ or $CH_2$.
In some embodiments, V is $C(=O)$.
In some embodiments, V is $S(=O)_2$.
In some embodiments, V is $CHR^{3c}$.
In some embodiments, V is $CH_2$.
In some embodiments, T is $CH_2$.
In some embodiments, T is $C(=O)$.
In some embodiments, T is $S(=O)_2$.
In some embodiments, T is $CHR^{3a}$.
In some embodiments, T is $CH(CH_3)$.
In some embodiments, Q is $S(=O)_2$.
In some embodiments, Q is $(CHR^{3a})_n$; wherein n is 0, 1, or 2.
In some embodiments, Q is $(CH_2)_n$; wherein n is 0, 1, or 2.
In some embodiments, Q is $CH_2$, $CH(CH_3)$, $CH(CH_2CH_3)$, or $CH_2CH_2$.
In some embodiments, n is 1.
In some embodiments, n is 0.
In some embodiments, Q is $CHR^{3a}$.
In some embodiments, Q is $CH_2$.
In some embodiments, Q is $CH(CH_3)$.
In some embodiments, Q is $CH(CH_2CH_3)$.
In some embodiments, Q is $CH_2CH_2$.
In some embodiments, U is O.
In some embodiments, U is $NR^{3d}$.
In some embodiments, U is NH.
In some embodiments, U is $NCH_3$.

In some embodiments, $R^A$ is H; and Ar is

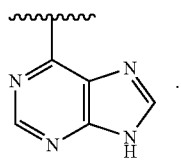

In some embodiments, $R^A$ is H; and Ar is

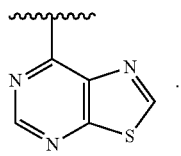 [SMILES: *c1ncnc2scnc12]

In some embodiments, $R^A$ is H; and Ar is

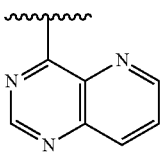

In some embodiments, $R^A$ and Ar, together with the N to which they are attached, combine to form a moiety of formula:

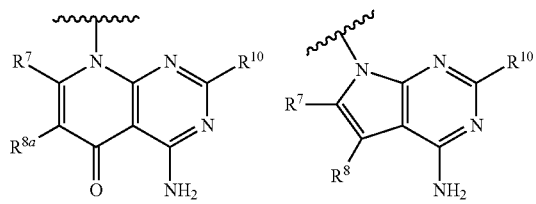

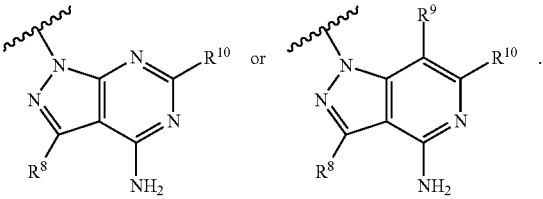

In some embodiments, $R^A$ and Ar, together with the N to which they are attached, combine to form a moiety of formula:

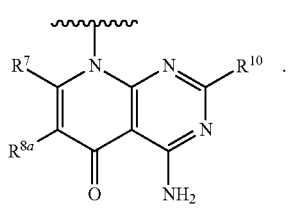

In some embodiments, $R^A$ and Ar, together with the N to which they are attached, combine to form a moiety of formula:

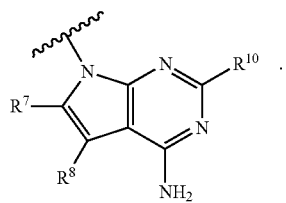

In some embodiments, $R^A$ and Ar, together with the N to which they are attached, combine to form a moiety of formula:

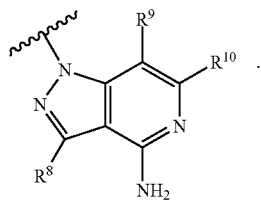

In some embodiments, $R^A$ and Ar, together with the N to which they are attached, combine to form a moiety of formula:

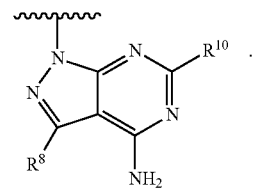

In some embodiments, $R^A$ and Ar, together with the N to which they are attached, combine to form a moiety of formula:

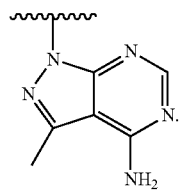

In some embodiments, $R^1$ is methyl.
In some embodiments, $R^1$ is methyl or ethyl.
In some embodiments, $R^4$ is $C_{1-4}$ alkyl, halo, or CN.
In some embodiments, $R^4$ is $C_{1-4}$ alkyl.
In some embodiments, $R^4$ is methyl.
In some embodiments, $R^4$ is halo.
In some embodiments, $R^4$ is F.
In some embodiments, $R^4$ is CN.
In some embodiments, $R^5$ is halo.
In some embodiments, $R^5$ is chloro.
In some embodiments, $R^6$ is H.

In some embodiments, $R^{3b}$ is H, Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups.

In some embodiments, $R^{3b}$ is H, Cy, $C_{1-6}$ alkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl, $C_{1-6}$ haloalkyl, and Cy; wherein said $C_{1-6}$ alkyl are each optionally substituted with 1, 2, or 3 independently selected $R^{13b}$ groups.

In some embodiments, $R^{3b}$ is H, Cy, —($C_{1-3}$ alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups.

In some embodiments, $R^{3b}$ is H, Cy, —($C_{1-3}$ alkylene)-Cy, $C_{1-6}$ alkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl, $C_{1-6}$ haloalkyl, and Cy; wherein said $C_{1-6}$ alkyl are each optionally substituted with 1, 2, or 3 independently selected $R^{13b}$ groups.

In some embodiments, each Cy is independently selected from $C_{3-7}$ cycloalkyl, 4-8 membered heterocycloalkyl, phenyl, and 5-10 membered heteroaryl, wherein said $C_{3-7}$ cycloalkyl, 4-8 membered heterocycloalkyl, phenyl, and 5-10 membered heteroaryl are optionally substituted with 1, 2, 3, or 4 independently selected $R^{13b}$ groups.

In some embodiments, each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups.

In some embodiments, each $R^{13b}$ is independently selected from CN, $C_{1-6}$ alkyl, $C_{1-6}$ haloalkyl, $OR^{a1}$, $C(=O)R^{b1}$, or $C(=O)OR^{a1}$.

In some embodiments, each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1, 2, or 3 independently selected $R^{11}$ groups.

In some embodiments, each $R^{a1}$, $R^{b1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

In some embodiments, each $R^{11}$ is independently selected from OH, CN, $C_{1-3}$ alkoxy, amino, $C_{1-3}$ alkylamino, di($C_{1-3}$ alkyl)amino, carbamyl, $C_{1-3}$ alkylcarbamyl, and di($C_{1-3}$ alkyl)carbamyl.

In some embodiments, each $R^{11}$ is independently selected from OH and carbamyl.

In some embodiments, the compound is a compound of Formula II:

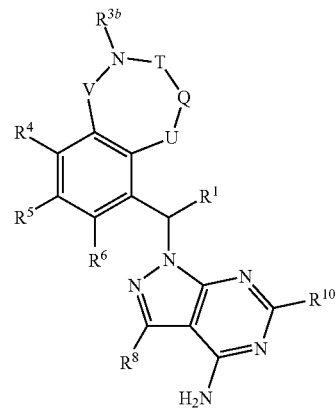

II or a pharmaceutically acceptable salt thereof.

In some embodiments, the compound is a compound of Formula III:

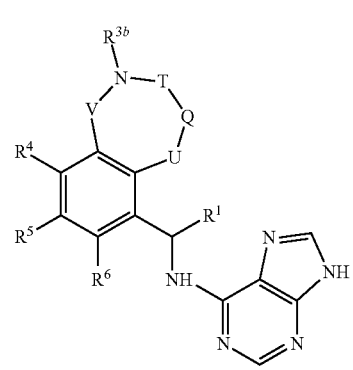

III or a pharmaceutically acceptable salt thereof.

In some embodiments, the compound is a compound of Formula IV:

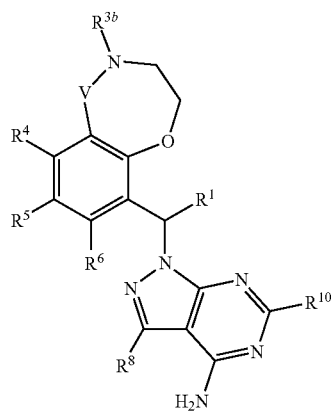

IV or a pharmaceutically acceptable salt thereof.

In some embodiments of the compound of Formula IV, V is $C(=O)$ or $CH_2$.

In some embodiments, the compound is a compound of Formula IVa:
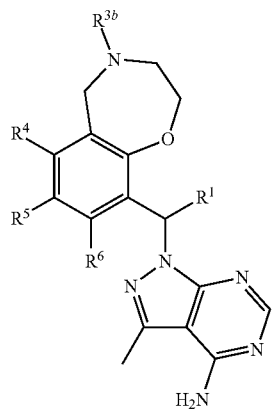
IVa
or a pharmaceutically acceptable salt thereof.
In some embodiments, the compound is a compound of Formula IVb:
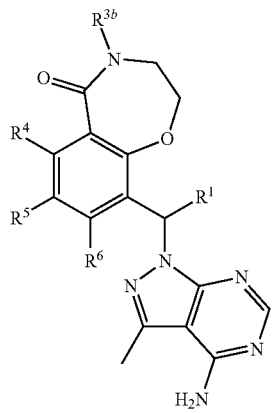
IVb
or a pharmaceutically acceptable salt thereof.
In some embodiments, the compound is a compound of Formula V, VI, VII, VIII, IX, X, XI, XII, XIII, XIV, XV, XVI, XVII, XVIII, XIX, or XX:
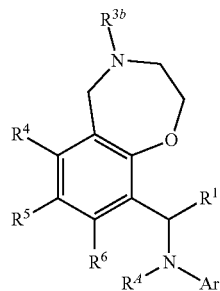
V
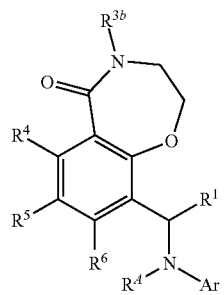
VI
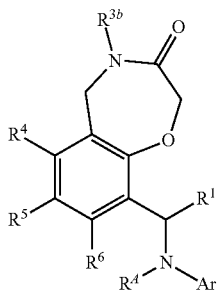
VII
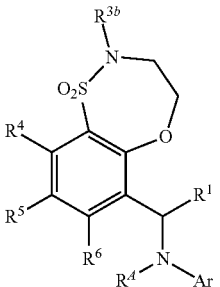
VIII
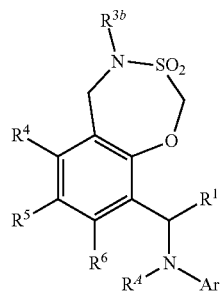
IX
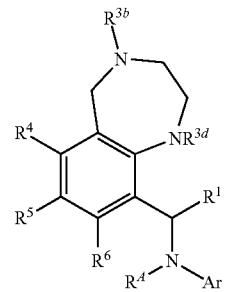
X XI 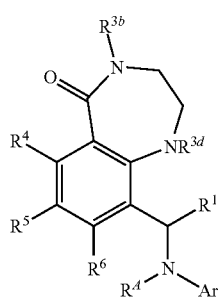
XII 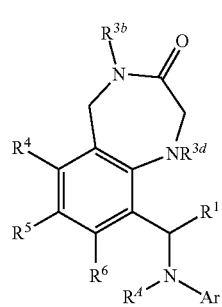
XIII 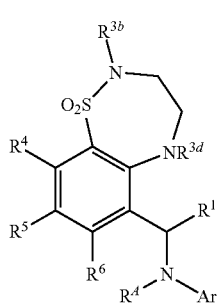
XIV 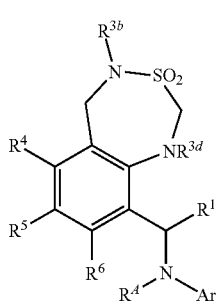
XV 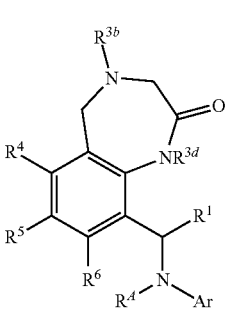
XVI 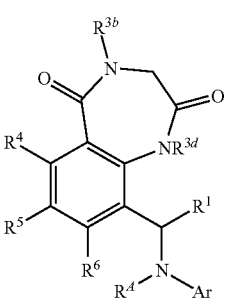
XVII 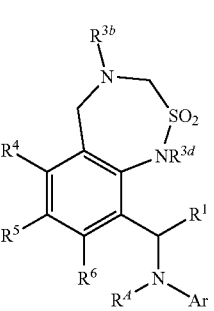
XVIII 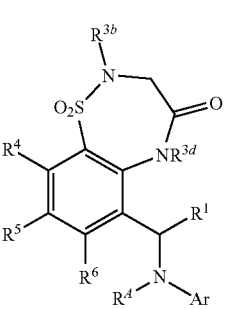
XIX 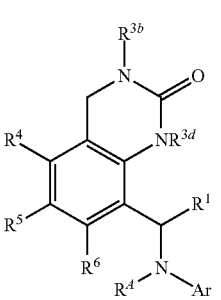
XX 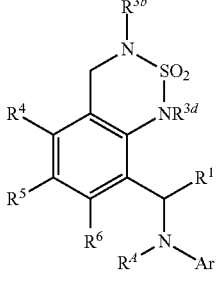
or a pharmaceutically acceptable salt thereof.

In some embodiments, the compound is a compound of Formula XXI, XXII or XXIII:

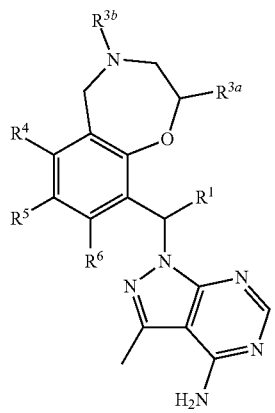

XXI

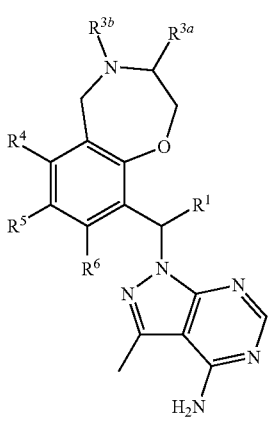

XXII

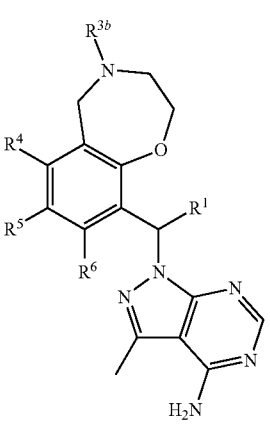

XXIII or a pharmaceutically acceptable salt thereof.

In some embodiments, $R^a$ is methyl or ethyl for the compound of Formula XXI, XXII, or XIII, or pharmaceutically acceptable salt thereof.

In some embodiments, the compound is a compound of Formula XXIa, XXIb, or XXIIa:

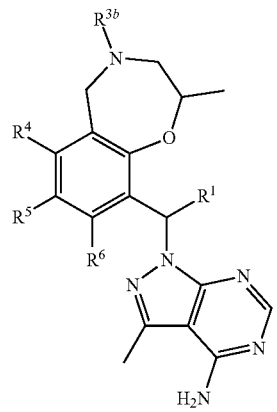

XXIa

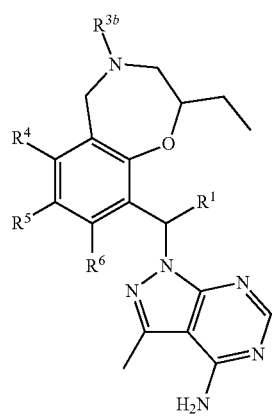

XXIb

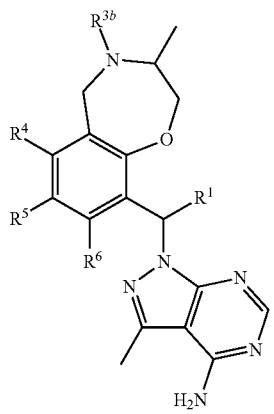

XXIIa or a pharmaceutically acceptable salt thereof.

In some embodiments, the compound is a compound of Formula XXIV:

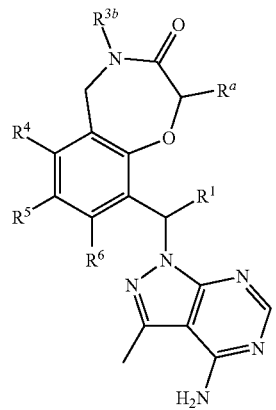

XXIV or a pharmaceutically acceptable salt thereof.

In some embodiments, $R^a$ is methyl for the compound of Formula XXIV, or pharmaceutically acceptable salt thereof.

In some embodiments, the compound is a compound of Formula II:

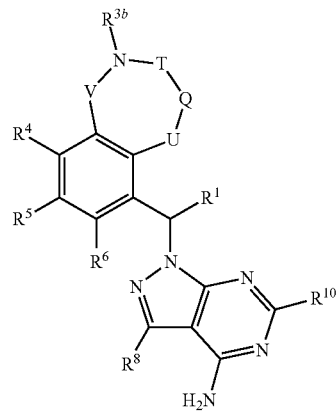

II or a pharmaceutically acceptable salt thereof, wherein:

V is C(=O), S(=O)$_2$, or CH$_2$;
T is C(=O), S(=O)$_2$, or CH$_2$;
Q is C(=O), S(=O)$_2$, or CH$_2$;
U is O or NR$^{3d}$;
provided that when T is C(=O) or S(=O)$_2$, then Q is CH$_2$;
further provided that when Q is C(=O) or S(=O)$_2$, then T is CH$_2$, and U is NR$^{3d}$;
$R^1$ is C$_{1-3}$ alkyl;
$R^{3b}$ is H, Cy, —(C$_{1-3}$ alkylene)-Cy, C$_{1-6}$ alkyl, C$_{2-6}$ alkenyl, C$_{2-6}$ alkynyl, C$_{1-6}$ haloalkyl, C(=O)R$^b$, C(=O)NR$^c$R$^d$, C(=O)OR$^a$, S(=O)$_2$R$^b$, or S(=O)$_2$NR$^c$R$^d$; wherein said C$_{1-6}$ alkyl, C$_{2-6}$ alkenyl, and C$_{2-6}$ alkynyl are optionally substituted by 1, 2, 3, or 4 independently selected R$^{13b}$ groups;
$R^{3d}$ is H, C$_{1-4}$ alkyl, C$_{1-4}$ haloalkyl, C$_{1-4}$ alkoxy-C$_{1-4}$ alkyl, or C$_{1-4}$ haloalkoxy-C$_{1-4}$ alkyl;
$R^4$ is H, halo, OH, CN, C$_{1-4}$ alkyl, C$_{1-4}$ haloalkyl, C$_{1-4}$ alkoxy, or C$_{1-4}$ haloalkoxy;
$R^5$ is halo, OH, CN, C$_{1-4}$ alkyl, C$_{1-4}$ haloalkyl, C$_{1-4}$ alkoxy, C$_{1-4}$ haloalkoxy, or cyclopropyl;
$R^6$ is H;
$R^8$ is H, halo, —OH, —CN, C$_{1-6}$ alkyl, or C$_{1-6}$ haloalkyl;
$R^{10}$ is H or C$_{1-4}$ alkyl;

each $R^{11}$ is independently selected from halo, OH, NO$_2$, CN, C$_{1-3}$ alkyl, C$_{1-3}$ haloalkyl, C$_{1-3}$ alkoxy, C$_{1-3}$ haloalkoxy, amino, C$_{1-3}$ alkylamino, and di(C$_{1-3}$ alkyl)amino;

each $R^{13b}$ is independently selected from halo, CN, NO$_2$, C$_{1-6}$ alkyl, C$_{2-6}$ alkenyl, C$_{2-6}$ alkynyl, C$_{1-6}$ haloalkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$S(=O)R$^{b1}$, NR$^{c1}$S(=O)$_2$NR$^{c1}$R$^{d1}$, S(=O)R$^{b1}$, S(=O)$_2$R$^{b1}$, and S(=O)$_2$NR$^{c1}$R$^{d1}$; wherein said C$_{1-6}$ alkyl, C$_{2-6}$ alkenyl, C$_{2-6}$ alkynyl are each optionally substituted with 1, 2, or 3 independently selected R$^{11}$ groups;

each Cy is independently selected from C$_{3-7}$ cycloalkyl, 4-10 membered heterocycloalkyl, phenyl, and 5-10 membered heteroaryl, wherein said C$_{3-7}$ cycloalkyl, 4-10 membered heterocycloalkyl, phenyl, and 5-10 membered heteroaryl are optionally substituted with 1, 2, 3, or 4 independently selected R$^{13b}$ groups;

each $R^a$, $R^c$, and $R^d$ is independently selected from H, C$_{1-6}$ alkyl, C$_{1-6}$ haloalkyl, C$_{2-6}$ alkenyl, C$_{2-6}$ alkynyl, and Cy; wherein said C$_{1-6}$ alkyl, C$_{2-6}$ alkenyl, and C$_{2-6}$ alkynyl are each optionally substituted with 1, 2, or 3 independently selected R$^{13b}$ groups;

each $R^b$ is independently selected from C$_{1-6}$ alkyl, C$_{1-6}$ haloalkyl, C$_{2-6}$ alkenyl, C$_{2-6}$ alkynyl, and Cy; wherein said C$_{1-6}$ alkyl, C$_{2-6}$ alkenyl, and C$_{2-6}$ alkynyl are each optionally substituted with 1, 2, or 3 independently selected R$^{13b}$ groups; or each $R^{a1}$, $R^{c1}$, and $R^{d1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, 4-7 membered heterocycloalkyl, phenyl, and 5-6 membered heteroaryl; wherein said C$_{1-6}$ alkyl, C$_{2-6}$ alkenyl, C$_{2-6}$ alkynyl, C$_{3-7}$ cycloalkyl, 4-7 membered heterocycloalkyl, phenyl and 5-6 membered heteroaryl are each optionally substituted with 1, 2, or 3 independently selected R$^{11}$ groups; and each $R^{b1}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, 4-7 membered heterocycloalkyl, phenyl, and 5-6 membered heteroaryl; wherein said C$_{1-6}$ alkyl, C$_{2-6}$ alkenyl, C$_{2-6}$ alkynyl, C$_{3-7}$ cycloalkyl, 4-7 membered heterocycloalkyl, phenyl and 5-6 membered heteroaryl are each optionally substituted with 1, 2, or 3 independently selected R$^{11}$ groups; or each Cy$^2$ is independently selected from C$_{3-7}$ cycloalkyl, 4-7 membered heterocycloalkyl, phenyl, 5-6 membered heteroaryl, and 9-10-membered bicyclic heteroaryl, each of which is optionally substituted with 1, 2, 3, or 4 independently selected R$^{11}$ groups.

In some embodiments, the compound is a compound of Formula II:

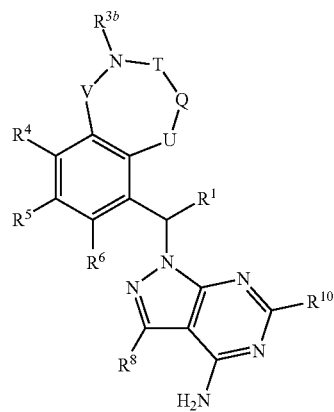

II or a pharmaceutically acceptable salt thereof, wherein:

V is $C(=O)$, $S(=O)_2$, or $CH_2$;

T is $C(=O)$, $S(=O)_2$, $CH_2$, or $CH(CH_3)$;

Q is $C(=O)$, $S(=O)_2$, $CH_2$, $CH(CH_3)$, $CH(CH_2CH_3)$, or $CH_2CH_2$;

U is O or $NR^{3d}$;

provided that when T is $C(=O)$ or $S(=O)_2$, then Q is $CH_2$ or $CH(CH_3)$;

further provided that when Q is $C(=O)$ or $S(=O)_2$, then T is $CH_2$, and U is $NR^{3d}$;

$R^1$ is $C_{1-3}$ alkyl;

$R^{3b}$ is H, Cy, —($C_{1-3}$ alkylene)-Cy, $C_{1-6}$ alkyl, $C_{2-6}$ alkenyl, $C_{2-6}$ alkynyl, $C_{1-6}$ haloalkyl, $C(=O)R^b$, $C(=O)NR^cR^d$, $C(=O)OR^a$, $S(=O)_2R^b$, or $S(=O)_2NR^cR^d$; wherein said $C_{1-6}$ alkyl, $C_{2-6}$ alkenyl, and $C_{2-6}$ alkynyl are optionally substituted by 1, 2, 3, or 4 independently selected $R^{13b}$ groups;

$R^{3d}$ is H, $C_{1-4}$ alkyl, $C_{1-4}$ haloalkyl, $C_{1-4}$ alkoxy-$C_{1-4}$ alkyl, or $C_{1-4}$ haloalkoxy-$C_{1-4}$ alkyl;

$R^4$ is H, halo, OH, CN, $C_{1-4}$ alkyl, $C_{1-4}$ haloalkyl, $C_{1-4}$ alkoxy, or $C_{1-4}$ haloalkoxy;

$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;

$R^6$ is H;

$R^8$ is H, halo, —OH, —CN, $C_{1-6}$ alkyl, or $C_{1-6}$ haloalkyl;

$R^{10}$ is H or $C_{1-4}$ alkyl;

each $R^{11}$ is independently selected from halo, OH, $NO_2$, CN, $C_{1-3}$ alkyl, $C_{1-3}$ haloalkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, and di($C_{1-3}$ alkyl)carbamyl;

each $R^{13b}$ is independently selected from halo, CN, $NO_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}S(=O)R^{b1}$, $NR^{c1}S(=O)_2NR^{c1}R^{d1}$, $S(=O)R^{b1}$, $S(=O)_2R^{b1}$, and $S(=O)_2NR^{c1}R^{d1}$; wherein said $C_{1-6}$ alkyl, $C_{2-6}$ alkenyl, $C_{2-6}$ alkynyl are each optionally substituted with 1, 2, or 3 independently selected $R^{11}$ groups;

each Cy is independently selected from $C_{3-7}$ cycloalkyl, 4-10 membered heterocycloalkyl, phenyl, and 5-10 membered heteroaryl, wherein said $C_{3-7}$ cycloalkyl, 4-10 membered heterocycloalkyl, phenyl, and 5-10 membered heteroaryl are optionally substituted with 1, 2, 3, or 4 independently selected $R^{13b}$ groups;

each $R^a$, $R^c$, and $R^d$ is independently selected from H, $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups;

each $R^b$ is independently selected from $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups; or each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; and each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; or each $Cy^2$ is independently selected from $C_{3-7}$ cycloalkyl, 4-7 membered heterocycloalkyl, phenyl, 5-6 membered heteroaryl, and 9-10-membered bicyclic heteroaryl, each of which is optionally substituted with 1, 2, 3, or 4 independently selected $R^{11}$ groups.

In some embodiments:

$R^4$ is $C_{1-4}$ alkyl;

$R^5$ is halo;

$R^6$ is H;

$R^{3b}$ is H, Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl, $C_{1-6}$ haloalkyl, and Cy; wherein said $C_{1-6}$ alkyl are each optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, and $C(=O)OR^{a1}$;

each $R^{a1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

In some embodiments:

$R^1$ is methyl;

$R^4$ is methyl, F or CN;

$R^5$ is Cl;

$R^6$ is H;

$R^{3b}$ is H, Cy, —($C_{1-3}$ alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

In some embodiments, the compound is a compound of Formula II:

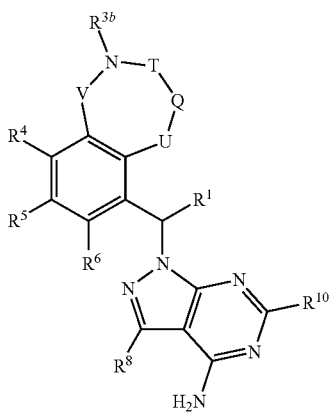

II or a pharmaceutically acceptable salt thereof, wherein:
$R^4$ is $C_{1-4}$ alkyl;
$R^5$ is halo;
$R^6$ is H;
$R^{10}$ is H or $C_{1-4}$ alkyl;
$R^{3b}$ is H, Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;
each $R^a$, $R^b$, $R^c$, and $R^d$ is independently selected from $C_{1-6}$ alkyl, $C_{1-6}$ haloalkyl, and Cy; wherein said $C_{1-6}$ alkyl are each optionally substituted with 1, 2, or 3 independently selected $R^{13b}$ groups;
each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;
each $R^{13b}$ is independently selected from CN, $C_{1-6}$ alkyl, $C_{1-6}$ haloalkyl, $OR^{a1}$, $C(=O)R^{b1}$ and $C(=O)OR^{a1}$;
each $R^{a1}$ is independently selected from H, $C_{1-6}$ alkyl, and $C_{1-6}$ haloalkyl; and
each $R^{b1}$ is independently selected from $C_{1-6}$ alkyl and $C_{1-6}$ haloalkyl.

In some embodiments, the compound is a compound of Formula IV:

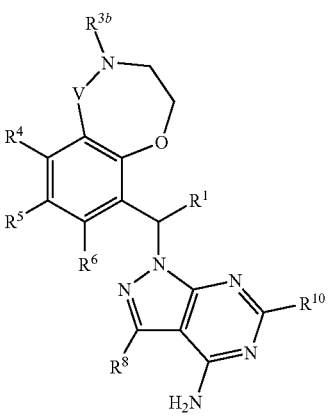

IV or a pharmaceutically acceptable salt thereof, wherein:
V is C(=O) or $CH_2$;
$R^4$ is $C_{1-4}$ alkyl;
$R^5$ is halo;
$R^6$ is H;
$R^8$ is $C_{1-6}$ alkyl;
$R^{10}$ is H or $C_{1-4}$ alkyl;
$R^{3b}$ is H, Cy, $C_{1-6}$ alkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;
each $R^a$, $R^b$, $R^c$, and $R^d$ is independently selected from $C_{1-6}$ alkyl and Cy; wherein said $C_{1-6}$ alkyl are each optionally substituted with 1, 2, or 3 independently selected $R^{13b}$ groups;
each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;
each $R^{13b}$ is independently selected from CN, $C_{1-6}$ alkyl, $OR^{a1}$, $C(=O)R^{b1}$, and $C(=O)OR^{a1}$;
each $R^{a1}$ is independently selected from H, $C_{1-6}$ alkyl, and $C_{1-6}$ haloalkyl; and
each $R^{b1}$ is independently selected from $C_{1-6}$ alkyl and $C_{1-6}$ haloalkyl.

In some embodiments, the compound is a compound of Formula IV:

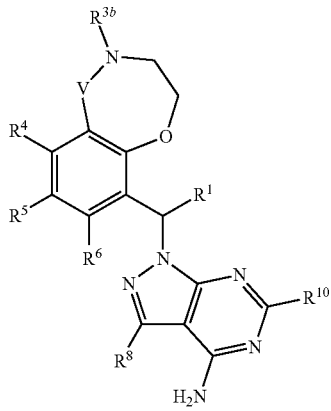

IV or a pharmaceutically acceptable salt thereof, wherein:
V is C(=O) or $CH_2$;
$R^1$ is methyl;
$R^4$ is methyl, F or CN;
$R^5$ is Cl;
$R^6$ is H;
$R^{3b}$ is H, Cy, —($C_{1-3}$ alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;
each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;
each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

In some embodiments, the compound is a compound of Formula XXI, XXII, or XXXIII:

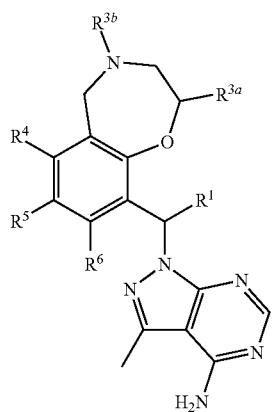

XXI

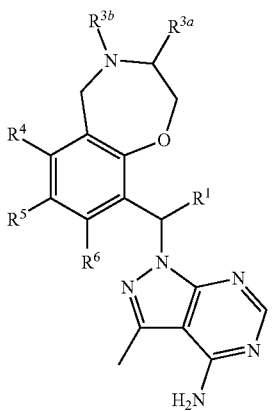

XXII

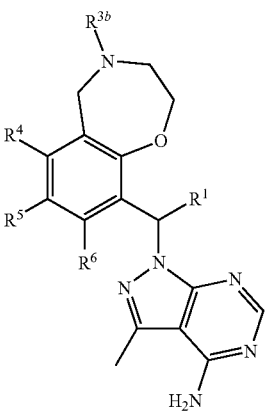

XXIII or a pharmaceutically acceptable salt thereof, wherein:
$R^1$ is methyl;
$R^{3a}$ is methyl or ethyl;
$R^4$ is methyl, F or CN;
$R^5$ is Cl;
$R^6$ is H;
$R^{3b}$ is H, Cy, —($C_{1-3}$ alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}OR^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

In some embodiments, the compound is a compound of Formula XXIV:

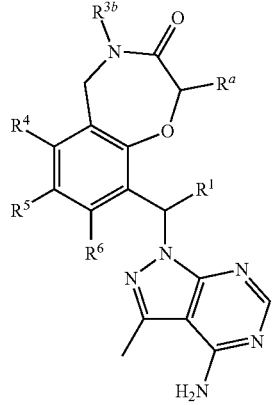

XXIV or a pharmaceutically acceptable salt thereof, wherein:
$R^1$ is methyl;
$R^{3a}$ is methyl;
$R^4$ is methyl, F or CN;
$R^5$ is Cl;
$R^6$ is H;
$R^{3b}$ is H, Cy, —($C_{1-3}$ alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

It is appreciated that certain features of the invention, which are, for clarity, described in the context of separate embodiments, can also be provided in combination in a single embodiment (the embodiments in the specification should be construed as if they were written as claims, which are multiply dependent on each of the other embodiments). Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R'')$_n$— includes both —NR(CR'R'')$_n$— and —(CR'R'')$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(=O)— group. Also may be written as C(O).

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, the term "$C_{1-3}$ alkoxy-$C_{1-3}$ alkyl" refers to a group of formula —($C_{1-3}$ alkylene)-O($C_{1-3}$ alkyl).

As used herein, the term "$C_{1-4}$ alkoxy-$C_{1-4}$ alkyl" refers to a group of formula —($C_{1-4}$ alkylene)-O($C_{1-4}$ alkyl).

As used herein, the term "$C_{1-4}$ haloalkoxy-$C_{1-4}$ alkyl" refers to a group of formula —($C_{1-4}$ alkylene)-O($C_{1-4}$ haloalkyl).

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, the halo group is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, or 7 ring-forming carbons ($C_{3-7}$). Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

A "bicyclic $C_{9-10}$ heteroaryl" is bicyclic fused heteroaryl having 9 to 10 ring members.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration (e.g., at the carbon to which $R^1$ is attached). In some embodiments, the compound has the (S)-configuration (e.g., at the carbon to which $R^1$ is attached).

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

In the Schemes below, the enantiomers of the compounds of Formula (I) (e.g., the carbon to which $R^1$ is attached is a chiral carbon) can be separated by chiral chromatography to afford a single enantiomer. Alternatively, a chiral intermediate may be separate by chiral chromatography and then used in the remaining steps of the Scheme to form a compound of Formula (I).

Compounds of Formula I can be formed as shown in Scheme I. Compound (i) can be acylated with a suitable acylating reagent (e.g., $R^1$—COCl) to form an ester which can be rearranged under Lewis acid conditions (e.g., $BF_3$/HOAc complex) to afford ketone (ii). Halogenation of ketone (ii) using $NX^2S$ (e.g., $NX^2S$=N-chlorosuccinamide, N-bromosuccinamide or N-iodosuccinamide) can give compound (iii) where $X^2$=Cl, Br, or I. The phenol can be converted to the ether (v) using standard Mitsunobu conditions (e.g., R"OH, where R"OH=HO-Q-T-$NR^{3b}$, for example $HOCH_2CH_2NR^{3b}P$, where P is a protecting group, such as Boc or Cbz, and activating agents, such as DEAD, $Ph_3P$;) or standard alkylating conditions (base and R"-Lg, where Lg=leaving group; for example $Na_2CO_3$ and $BrCH_2CH_2NHP$, where P is a protecting group, such as Boc or Cbz). The halo group of (v) can be coupled to a vinyl boronic acid or vinyl boronic ester (vi) ($R^{3c}$-M, where M is a boronic acid, boronic ester or an appropriately substituted metal (e.g., $R^{3c}$-M is $R^{3c}$—$B(OH)_2$, $R^{3c}$—$Sn(Bu)_4$, or Zn—$R^{3c}$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a vinyl derivative (vii). Oxidation of the vinyl group of compound (vii) under standard conditions (e.g., $OsO_4$ and then $NaIO_4$ or ozone and then a reducing agent, such as triphenylphosphine or DMS, can provide compound (viii). Deprotection of the nitrogen protecting group can give the amine that can cyclize to form the imine and be reduced with a suitable reagent, such as $NaBH_4$, to give an alcohol which can be converted to an intermediate (ix) bearing a leaving group, (e.g., Lg is chloride via reaction with $SO_2Cl_2$ or cyanuric chloride or mesylate via reaction with methanesulfonic anhydride). The intermediate (ix) can be reacted with a heterocycle (x) in the presence of a base (e.g., $CsCO_3$ or NaH) to give a heterocyclic derivative (xi). Alternatively, the intermediate (ix) can be converted to an azide derivative which can be reduced to an amine (xii) under appropriate reducing conditions, such as trimethylphosphine or TMSI. The amine (xii) can be optionally reacted with an appropriate alkylating agent $R^4X$ (e.g., MeI) or reacted under reductive amination conditions to give a secondary amine which can be reacted with a heteroaryl halide compound (e.g., Ar—X, such as 6-chloro-9H-purine) to give a compound of Formula I (xiii). The reaction of amine (xii) with $R^4$—$X^3$ can be skipped to give compounds of Formula I (xiii), wherein $R^4$ is H.

Scheme I

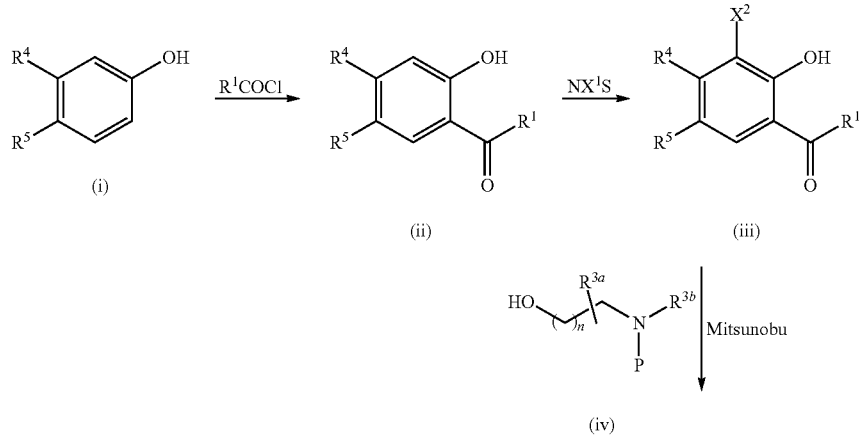

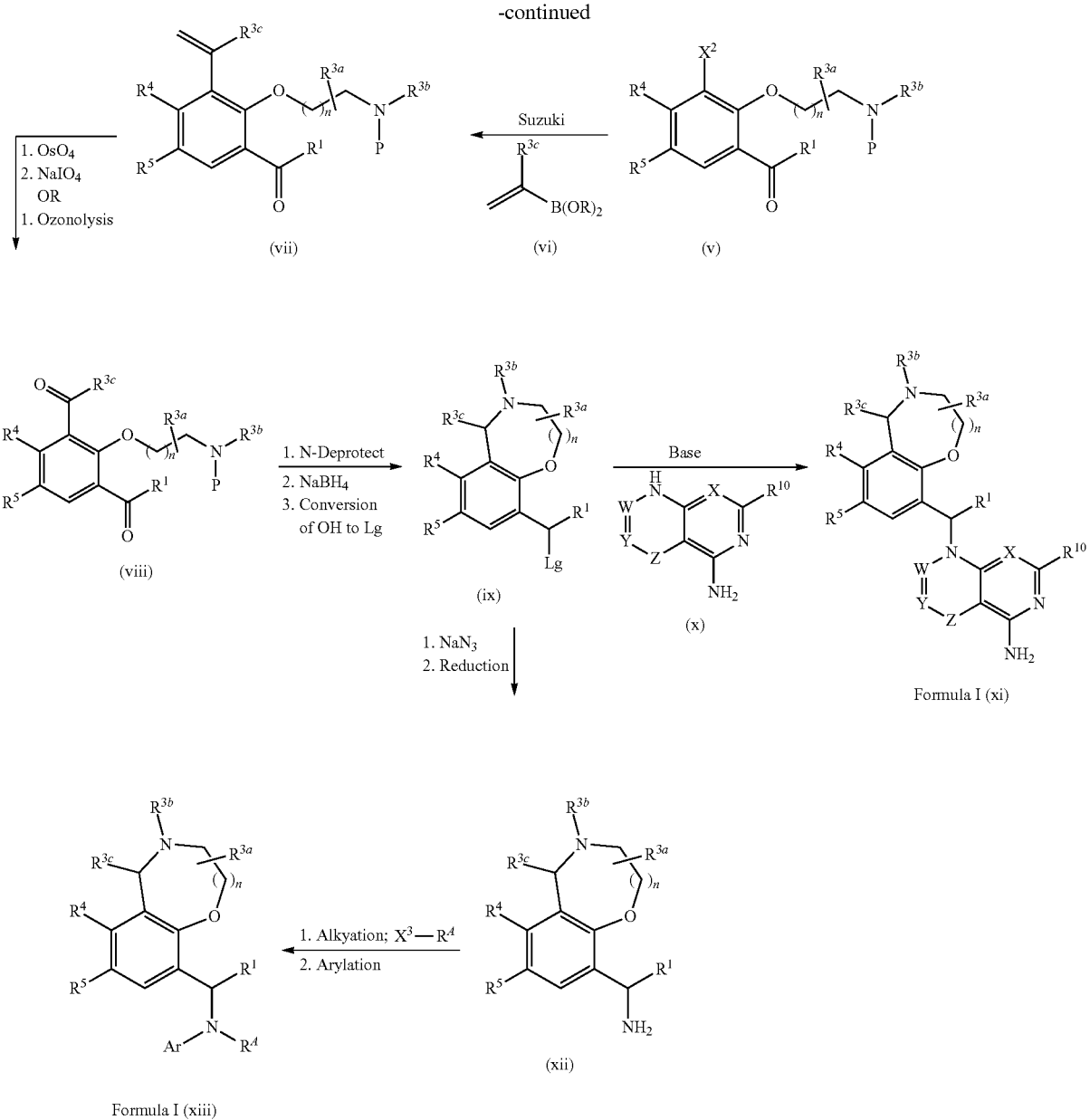

Compounds of Formula I can be formed as shown in Scheme II. Carbonyl derivative (i) (compound viii from Scheme I where $R^{3b}$=H) can be N-deprotected to give an amine that can cyclize to form an imine and then be reduced with a suitable reagent, such as NaBH$_4$, to give a bicyclic alcohol containing compound (ii). The alcohol (ii) which can be converted to a derivative bearing a leaving group, (e.g., Lg is chloride via reaction with SO$_2$Cl$_2$ or cyanuric chloride or mesylate via reaction with methanesulfonic anhydride) and then reacted with a heterocycle (iii) in the presence of a base (e.g., CsCO$_3$ or NaH) to give a heterocyclic derivative (iv). N-deprotection and reaction with a variety of acylating or alkylating or arylating agents can provide compounds (v). Alternatively, ketone (i) (compound (viii) from Scheme I where $R^{3b}$=H) can be N-deprotected to give an amine that can cyclize to form an imine and then be reduced with a suitable reagent, such as NaCNBH$_3$ to give a bicyclic amine (vi). Reaction of the amine (vi) with a variety of acylating or alkylating or arylating agents and then reduction of the ketone and conversion of the alcohol to a derivative bearing a leaving group, (e.g., Lg is chloride via reaction with SO$_2$Cl$_2$ or cyanuric chloride or mesylate via reaction with methanesulfonic anhydride) can provide compounds (vii). Reaction with a heterocycle (iii) in the presence of a base (e.g., CsCO$_3$ or NaH) can give a bicyclic derivative (v). Alternatively, intermediate (vii) can be converted to an azide and reduced with a suitable agent, such as trimethylphosphine or TMSI. The amine (viii) can be optionally reacted with an appropriate alkylating agent $R^A X^3$ (e.g., MeI) or reacted under reductive amination conditions to give a secondary amine which can be reacted with a heteroaryl halide compound (e.g., Ar—X$^4$, such as 6-chloro-9H-purine) to give a compound of Formula I (ix). The reaction of amine (viii) with $R^4$—X$^3$ can be skipped to give compounds of Formula I (ix), wherein $R^A$ is H.

Scheme II

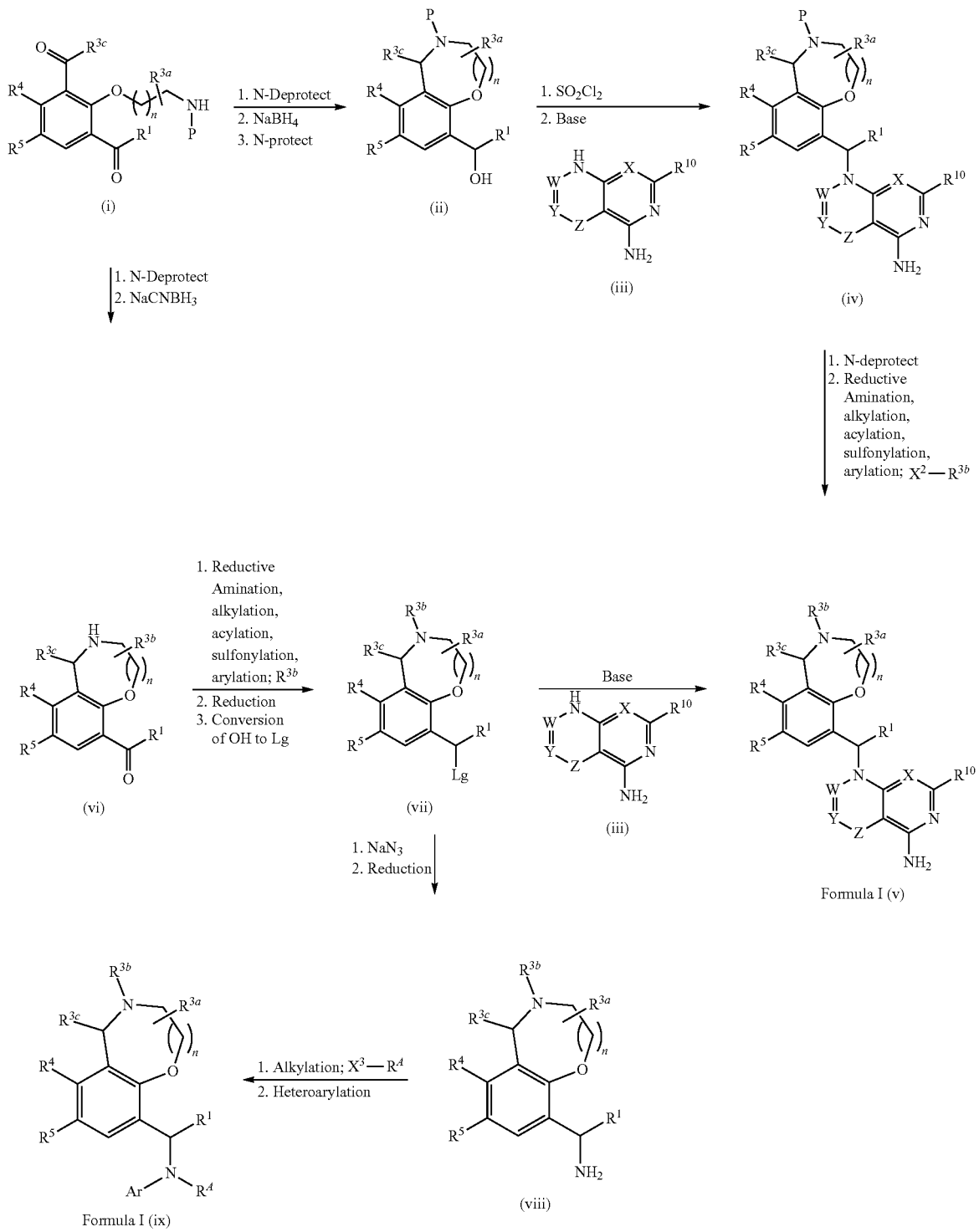

Compounds of Formula I can be formed as shown in Scheme III. Aldehyde (i) (compound viii from Scheme I) can be oxidized to the corresponding carboxylic acid and then N-deprotected to give an amine that can cyclize under standard peptide coupling conditions (e.g., HATU with DIEA) to provide an amide (ii). Alternatively, when $R^{3b}$=H, the amine of the carboxylic acid can be N-deprotected and converted to a secondary amine under reductive amination conditions or alkylation (e.g., $NaCNBH_3$ and $R^{3b}CHO$ or $R^{3b}$-halo and base) and then cyclized under standard peptide coupling conditions (e.g., HATU with DIEA) to provide an amide (ii). The ketone of compound (ii) can be converted to compounds of Formula I (iv and vi) by similar methods as described in Schemes I and II.

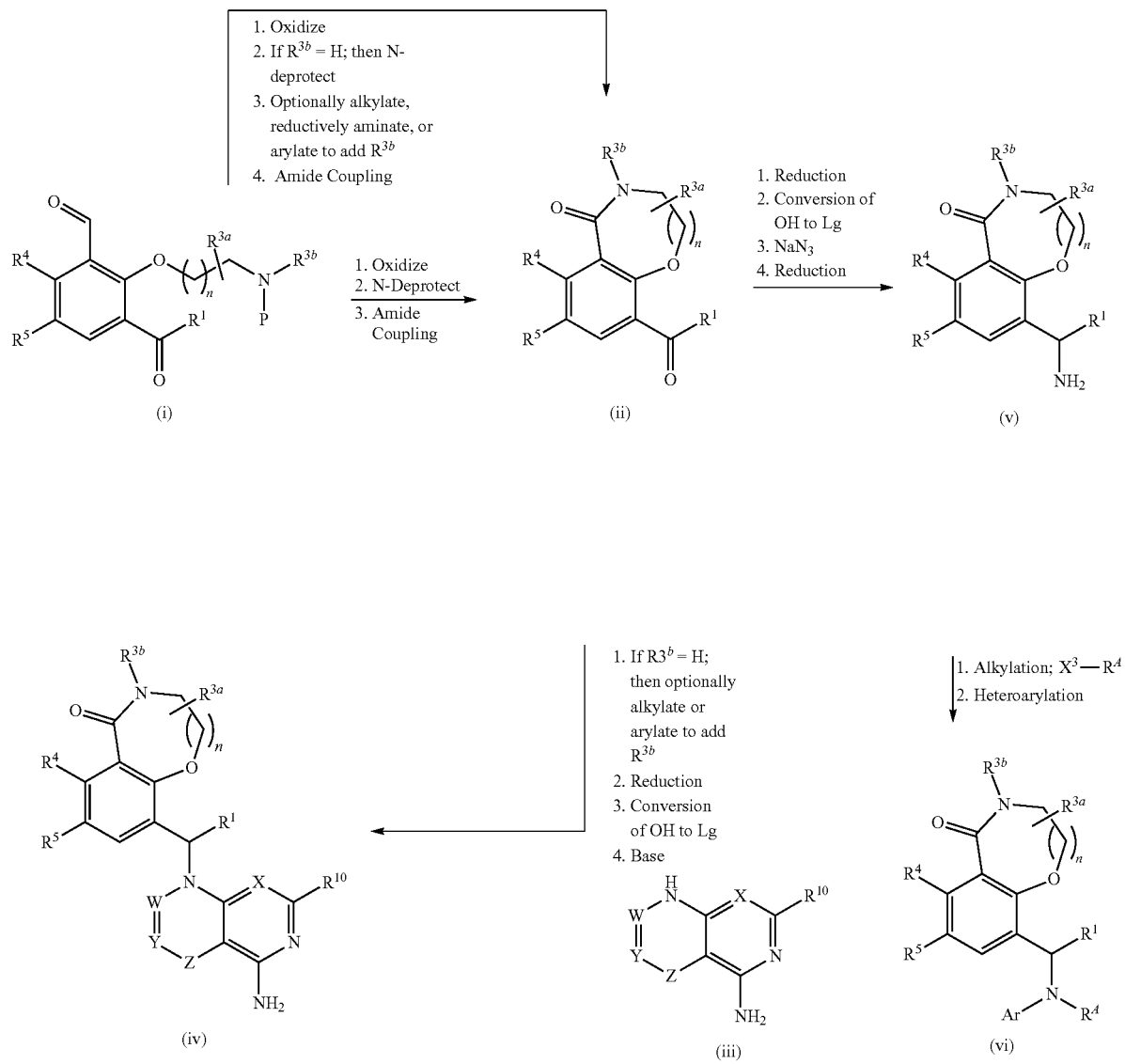

Scheme III

Compounds of Formula I can be formed as shown in Scheme IV. Phenol (i) can be converted to the corresponding triflate (ii) using triflic anhydride and base and then coupled to an amine (iv) by heating in base or under Buchwald conditions (e.g., in the presence of a palladium(0) catalyst, such as tetrakis(triphenylphosphine)palladium(0) and a base (e.g., an alkoxide base)) to afford diamine (iii). Halogenation of diamine (iii) using $NX^2S$ (e.g., $NX^2S$=N-chlorosuccinamide, N-bromosuccinamide or N-iodosuccinamide) can give compound (v) where $X^2$=Cl, Br, or I. The halo group of (v) can be coupled to a vinyl boronic acid or vinyl boronic ester (vi) ($R^{3c}$-M, where M is a boronic acid, boronic ester or an appropriately substituted metal (e.g., $R^{3c}$-M is $R^{3c}$—$B(OH)_2$, $R^{3c}$—$Sn(Bu)_4$, or Zn—$R^{3c}$), under standard Suzuki conditions or standard Stille conditions (e.g., in the presence of a palladium(0) catalyst, such as tetrakis(triphenylphosphine) palladium(0) and a base (e.g., a bicarbonate or carbonate base) or standard Negishi conditions (e.g., in the presence of a palladium(0) catalyst, such as tetrakis(triphenylphosphine) palladium(0), to give a vinyl derivative (vii). Oxidation of the vinyl group of compound (vii) under standard conditions (e.g., $OsO_4$ and then $NaIO_4$ or ozone and then a reducing agent, such as triphenylphosphine or DMS) can provide compound (viii). Deprotection of the nitrogen protecting group can give the amine that can cyclize to form the imine and be reduced with a suitable reagent, such as $NaBH_4$, to give an alcohol that can be converted to a intermediate (ix) bearing a leaving group, (e.g., Lg is chloride via reaction with $SO_2Cl_2$ or cyanuric chloride or mesylate via reaction with methanesulfonic anhydride). Intermediate (ix) can be converted to compounds of Formula I (xi and xiii) by similar methods as described in Schemes I and II.

Scheme IV

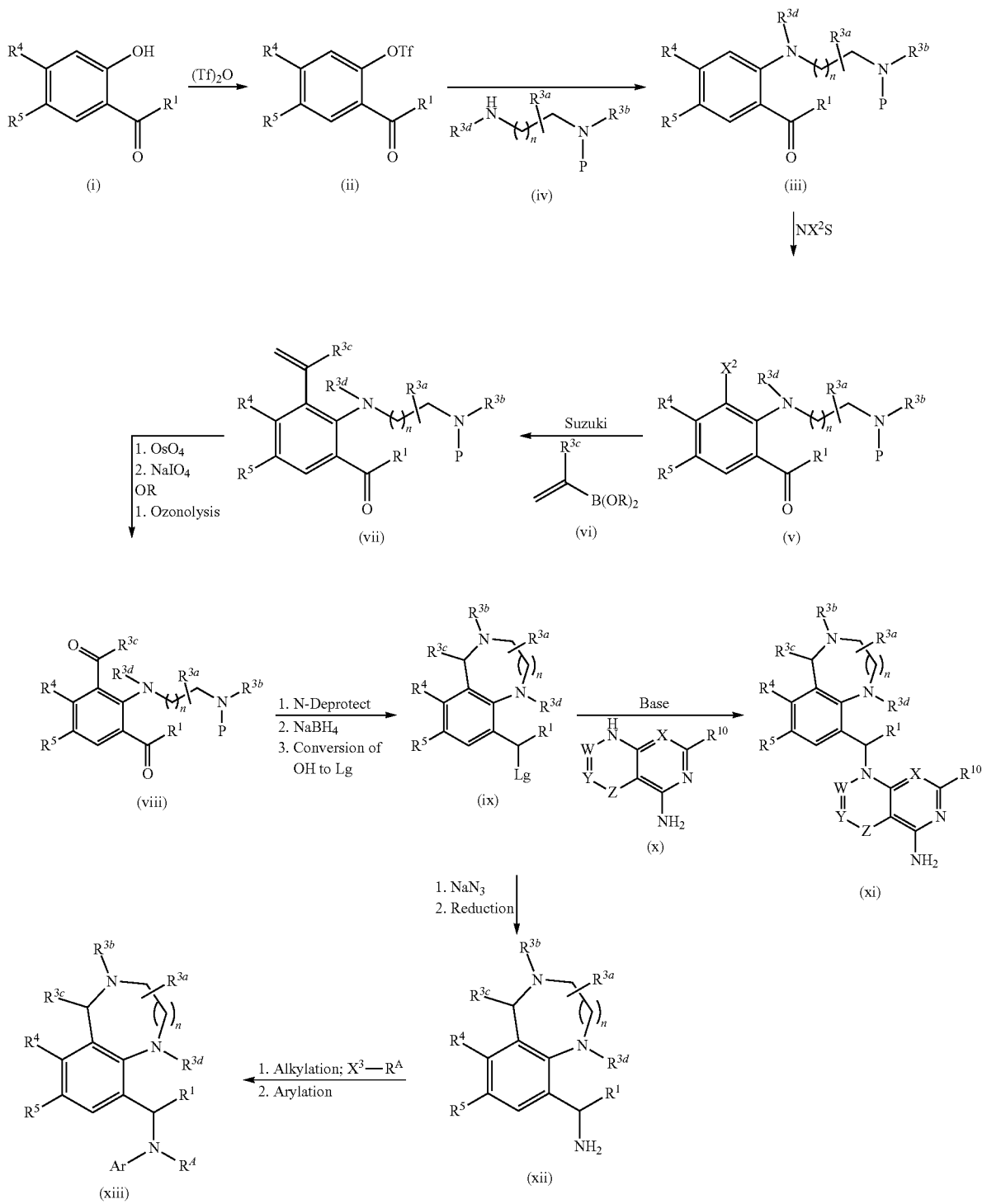

Compounds of Formula I can be formed as shown in Scheme V. Aldehyde (i) (compound viii where $R^{3c}$=H in Scheme IV) can be oxidized to the corresponding carboxylic acid and then N-deprotected to give an amine that can cyclize under standard peptide coupling conditions (e.g., HATU with DIEA) to provide an amide and then be reduced with a suitable reagent, such as NaBH$_4$, and the resulting alcohol can be converted to a intermediate (ii) bearing a leaving group, (e.g., Lg is chloride via reaction of the alcohol with SO$_2$Cl$_2$ or cyanuric chloride or mesylate via reaction with methanesulfonic anhydride). The intermediate compound (ii) can be converted to compounds of Formula I (iv and vi) by similar methods as shown for intermediates bearing leaving groups in Schemes I and II.

Scheme V

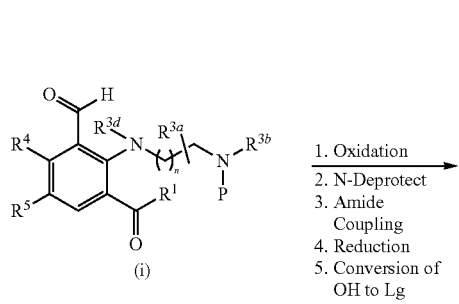
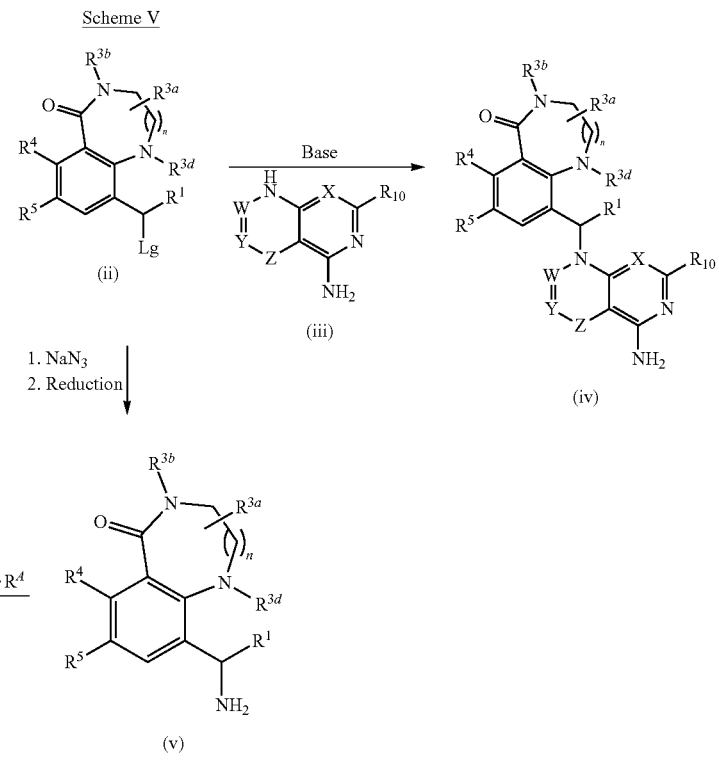

Compounds of Formula I can be formed as shown in Scheme VI. Phenol (i) can be converted to the corresponding triflate (ii) using triflic anhydride and base and then coupled to an amino-ester (e.g., $R^2$ is alkyl) (iv) by heating in base or under Buchwald conditions (e.g., in the presence of a palladium(0) catalyst, such as tetrakis(triphenylphosphine)palladium(0) and a base (e.g., an alkoxide base)) to afford ester (iii). Halogenation of ketone (iii) using $NX^2S$ (e.g., $NX^2S$=N-chlorosuccinamide, N-bromosuccinamide or N-iodosuccinamide) can give compound (v) where $X^2$=Cl, Br, or I. The halo group of (v) can be coupled to a vinyl boronic acid or vinyl boronic ester (vi) ($R^{3c}$-M, where M is a boronic acid, boronic ester or an appropriately substituted metal (e.g., $R^{3c}$-M is $R^{3c}$—B(OH)$_2$, $R^{3c}$—Sn(Bu)$_4$, or Zn—$R^{3c}$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a vinyl derivative (vii). Oxidation of the vinyl group of compound (vii) under standard conditions (e.g., $OsO_4$ and then $NaIO_4$ or ozone and then a reducing agent, such as triphenylphosphine or DMS, can provide compound (viii). Reductive amination with a suitable amine ($R^{3b}NH_2$) and appropriate reducing agent (e.g., $NaCHBH_3$) can give the corresponding amine product that can intramolecularly cyclize to form the amide and then be reduced with a suitable reagent, such as $NaBH_4$, and the resulting alcohol can be converted to a intermediate (ix) bearing a leaving group, (e.g., Lg is chloride via reaction with $SO_2Cl_2$ or cyanuric chloride or mesylate via reaction with methanesulfonic anhydride). Intermediate (ix) can be converted to compounds of Formula I (xi and xiii) by similar methods as described in Schemes I and II.

Compounds of Formula I can be formed as shown in Scheme VII. Phenol (i) can be converted to the corresponding triflate (ii) using triflic anhydride and base and then coupled to a primary amine ($R^{3d}NH_2$) by heating in base or under Buchwald conditions (e.g., in the presence of a palladium(0) catalyst, such as tetrakis(triphenylphosphine)palladium(0) and a base (e.g., an alkoxide base)), and then peptide coupling to an amino-acid (iv) can afford amide (iii). Halogenation of amide (iii) using $NX^2S$ (e.g., $NX^2S$=N-chlorosuccinamide, N-bromosuccinamide or N-iodosuccinamide) can give compound (v) where $X^2$=Cl, Br, or I. The halo group of (v) can be coupled to a vinyl boronic acid or vinyl boronic ester (vi) ($R^{3c}$-M, where M is a boronic acid, boronic ester or an appropriately substituted metal (e.g., $R^{3c}$-M is $R^{3c}$—B(OH)$_2$, $R^{3c}$—Sn(Bu)$_4$, or Zn—$R^{3c}$), under standard Suzuki conditions or standard Stille conditions (e.g., in the presence of a palladium(0) catalyst, such as tetrakis(triphenylphosphine) palladium(0) and a base (e.g., a bicarbonate or carbonate base) or standard Negishi conditions (e.g., in the presence of a palladium(0) catalyst, such as tetrakis(triphenylphosphine) palladium(0), to give a vinyl derivative (vii). Oxidation of the vinyl group of compound (vii) under standard conditions (e.g., $OsO_4$ and then $NaIO_4$ or ozone and then a reducing agent, such as triphenylphosphine or DMS, can provide compound (viii). Deprotection of the nitrogen protecting group can give the amine that can cyclize to form the imine and be reduced with a suitable reagent, such as $NaBH_4$, to give bicyclic alcohol which can be converted to a derivative (ix) bearing a leaving group, (e.g., Lg is chloride via reaction with $SO_2Cl_2$ or cyanuric chloride or mesylate via reaction with methanesulfonic anhydride). Intermediate (ix) can be converted to compounds of Formula I (xi and xiii) by similar methods as described in Schemes I, II and III.

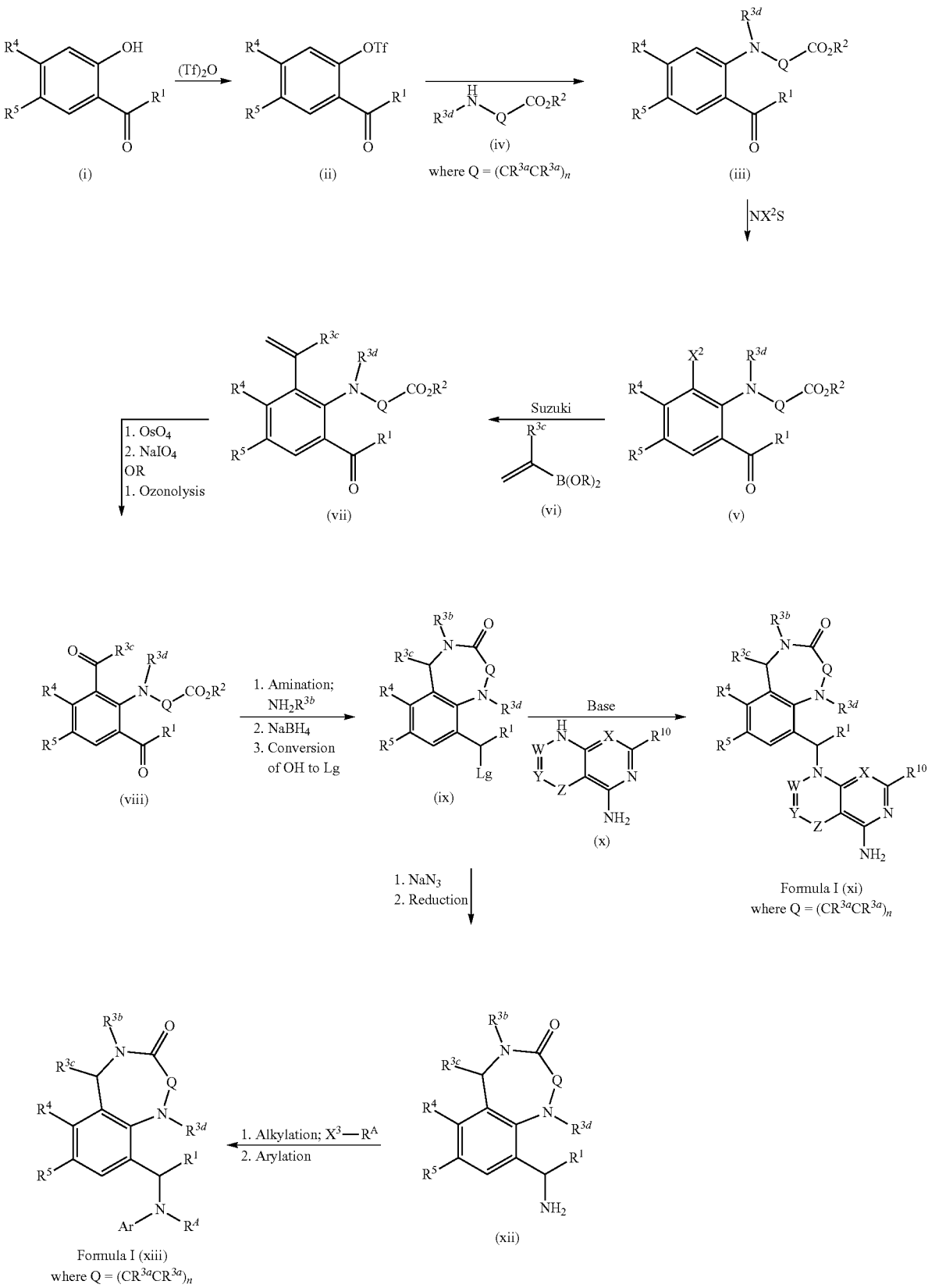

Scheme VII

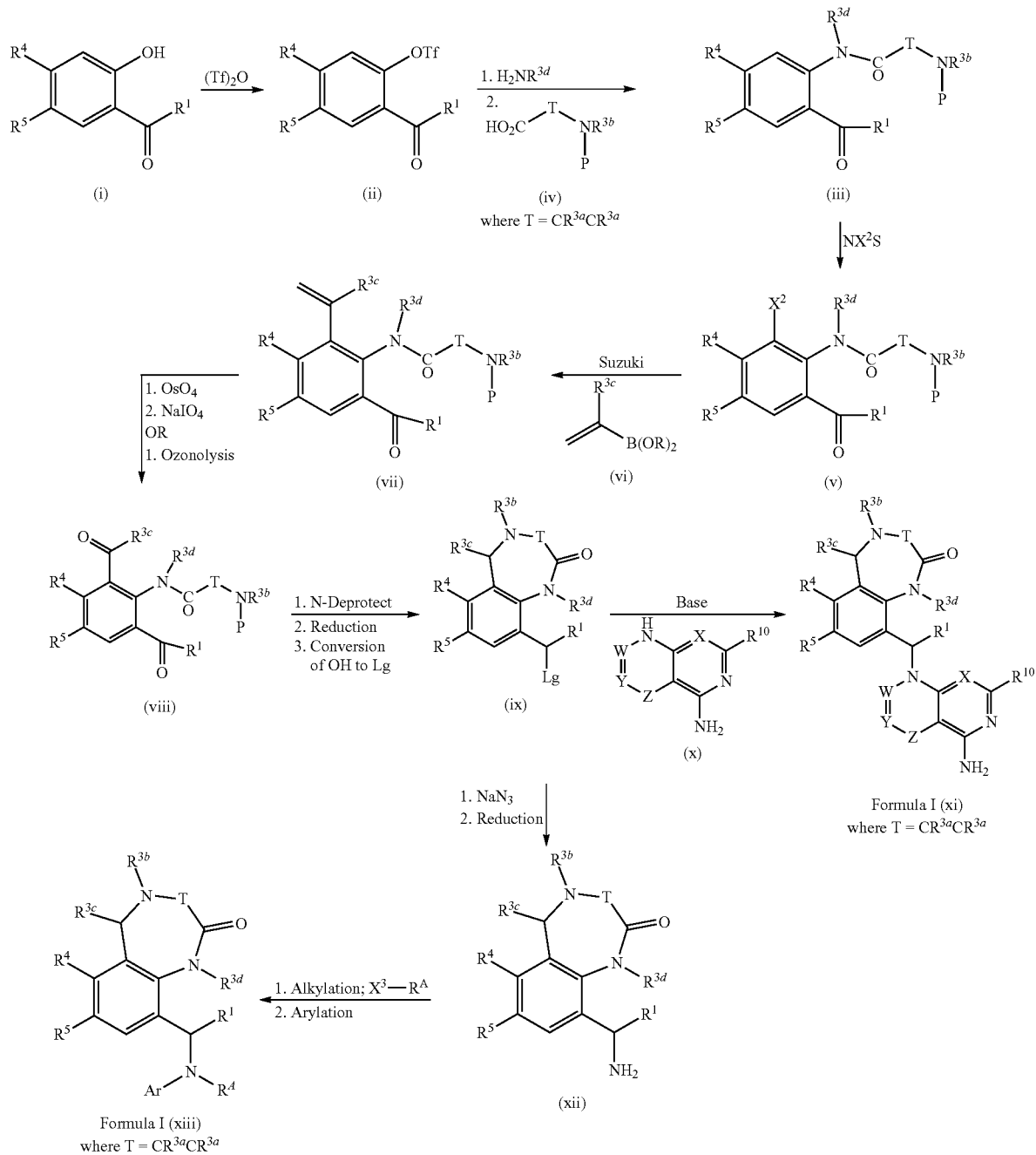

Compounds of Formula I can be formed as shown in Scheme VIII. Halogenation of ketone (i) using $NX^1S$ (e.g., $NX^1S$=N-chlorosuccinamide, N-bromosuccinamide or N-iodosuccinamide) can give compound (ii) where $X^1$=Cl, Br, or I. The phenol can be reacted with a halo-ester (iii) to give the ether (iv) using standard alkylating conditions (Base and R'-Lg, where Lg=leaving group (e.g., NaH and $BrCR^{3a}CO_2Me$). The halo group of (iv) can be coupled to a vinyl boronic acid or vinyl boronic ester (v) ($R^{3c}$-M, where M is a boronic acid, boronic ester or an appropriately substituted metal (e.g., $R^{3c}$-M is $R^{3c}$—$B(OH)_2$, $R^{3c}$—$Sn(Bu)_4$, or Zn—$R^{3c}$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a vinyl derivative (vi). Oxidation of the vinyl group of compound (vi) under standard conditions (e.g., $OsO_4$ and then $NaIO_4$ or ozone and then a reducing agent, such as triphenylphosphine or DMS, can provide compound (vii). Reductive amination with a suitable amine ($R^{3b}NH_2$) and appropriate reducing agent (e.g., $NaCNBH_3$) can give the corresponding amine product that can intramolecularly cyclize to form the amide and then be reduced with a suitable reagent, such as NaBH$_4$, and the resulting alcohol can be converted to a derivative (viii) bearing a leaving group, (e.g., Lg is chloride via reaction with SO$_2$Cl$_2$ or cyanuric chloride or mesylate via reaction with methanesulfonic anhydride). Intermediate (viii) can be converted to compounds of Formula I (x and xii) by similar methods as described in Schemes I and II.

lic acid and then N-deprotected to give an amine that can cyclize under standard peptide coupling conditions (e.g., HATU with DIEA) to provide an amide and then be reduced with a suitable reagent, such as NaBH$_4$, and the resulting alcohol can be converted to an intermediate (ii) bearing a leaving group, (e.g., Lg is chloride via reaction of the alcohol with SO$_2$Cl$_2$ or cyanuric chloride or mesylate via reaction with methanesulfonic anhydride). The intermediate com-

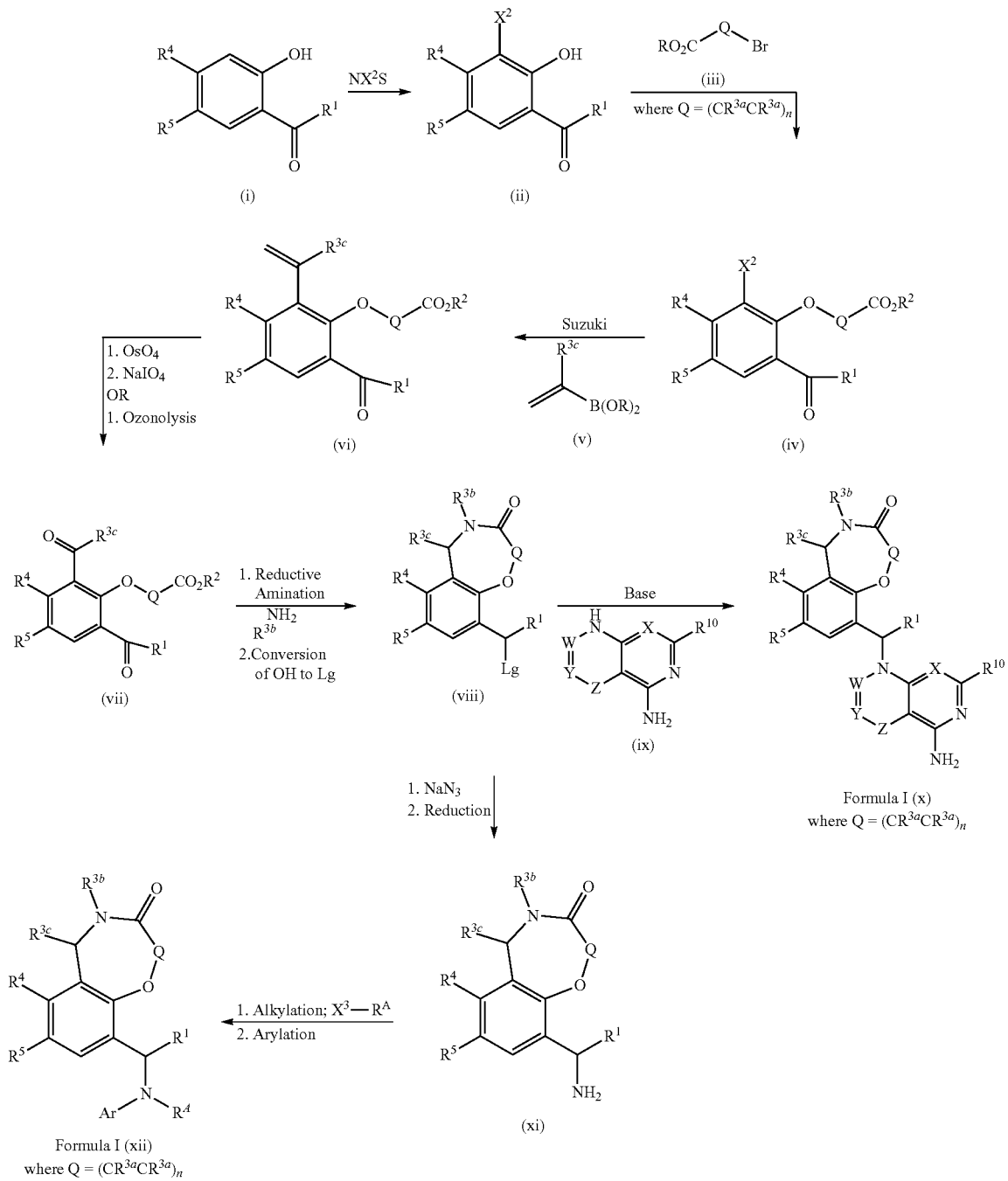

Scheme VIII

Compounds of Formula I can be formed as shown in Scheme IX. Aldehyde (i) (compound vii where R$^{3c}$=H in Scheme VIII) can be oxidized to the corresponding carboxypound (ii) can be converted to compounds of Formula I (iv and yl) by similar methods as shown for intermediates bearing leaving groups in Schemes I and II.

Scheme IX

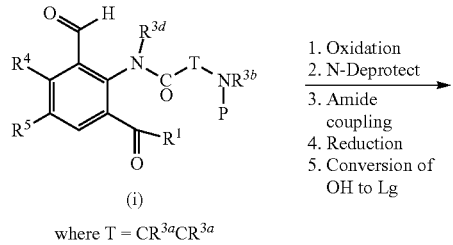

(i) where T = CR³ᵃCR³ᵃ

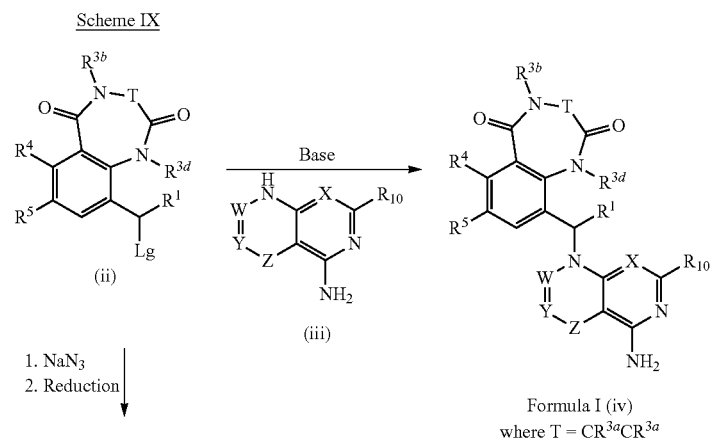

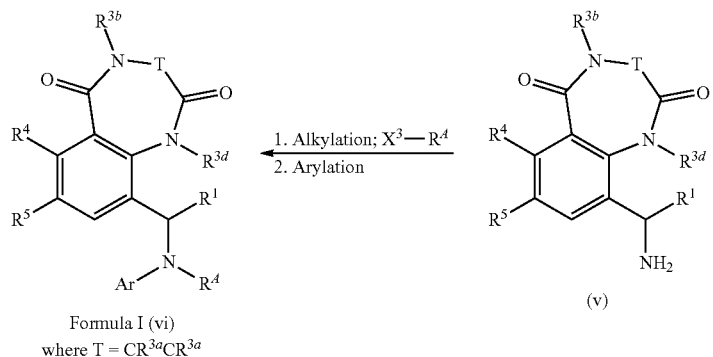

Compounds of Formula I can be formed as shown in Scheme X. Phenol (i) can be converted to the corresponding triflate (ii) using triflic anhydride and base and then coupled to a primary amine (e.g., $R^{3b}NH_2$) by heating in base or under Buchwald conditions (e.g., in the presence of a palladium(0) catalyst, such as tetrakis(triphenylphosphine)palladium(0) and a base (e.g., an alkoxide base)) and further protection (e.g., Boc or Cbz using $(Boc)_2O$ or Cbz-Cl, respectively) of the resulting amine can give compound (iii). Halogenation of compound (iii) using $NX^2S$ (e.g., $NX^2S$=N-chlorosuccinamide, N-bromosuccinamide or N-iodosuccinamide) can give compound (v) where $X^2$=Cl, Br, or I. The halo group of (v) can be coupled to a vinyl boronic acid or vinyl boronic ester (vi) ($R^{3c}$-M, where M is a boronic acid, boronic ester or an appropriately substituted metal (e.g., $R^{3c}$-M is $R^{3c}$—$B(OH)_2$, $R^{3c}$—$Sn(Bu)_4$, or Zn—$R^{3c}$), under standard Suzuki conditions or standard Stille conditions (e.g., in the presence of a palladium(0) catalyst, such as tetrakis(triphenylphosphine) palladium(0) and a base (e.g., a bicarbonate or carbonate base) or standard Negishi conditions (e.g., in the presence of a palladium(0) catalyst, such as tetrakis(triphenylphosphine) palladium(0), to give a vinyl derivative (vii). Oxidation of the vinyl group of compound (vii) under standard conditions (e.g., $OsO_4$ and then $NaIO_4$ or ozone and then a reducing agent, such as triphenylphosphine or DMS, can provide compound (viii). Reductive amination of carbonyl derivative (viii) with a suitable amine (iv) (e.g., $R^{3b}NH_2$) and appropriate reducing agent (e.g., $NaCHBH_3$) can give the corresponding amine product. Deprotection of the nitrogen protecting group can give a diamine that can be cyclized to form a urea (e.g., Q=CO by reaction with phosgene) or sulfamide (e.g., Q=$SO_2$ by reaction with $SO_2Cl_2$ or $NH_2SO_2NH_2$) and then reduction with a suitable reagent, such as $NaBH_4$, can give an alcohol which can be further converted to an intermediate (ix) bearing a leaving group, (e.g., Lg is chloride via reaction with $SO_2Cl_2$ or cyanuric chloride or mesylate via reaction with methanesulfonic anhydride). The intermediate compound (ix) can be converted to compounds of Formula I (xi and xiii) by similar methods as shown for intermediates bearing leaving groups in Schemes I and II.

Scheme X

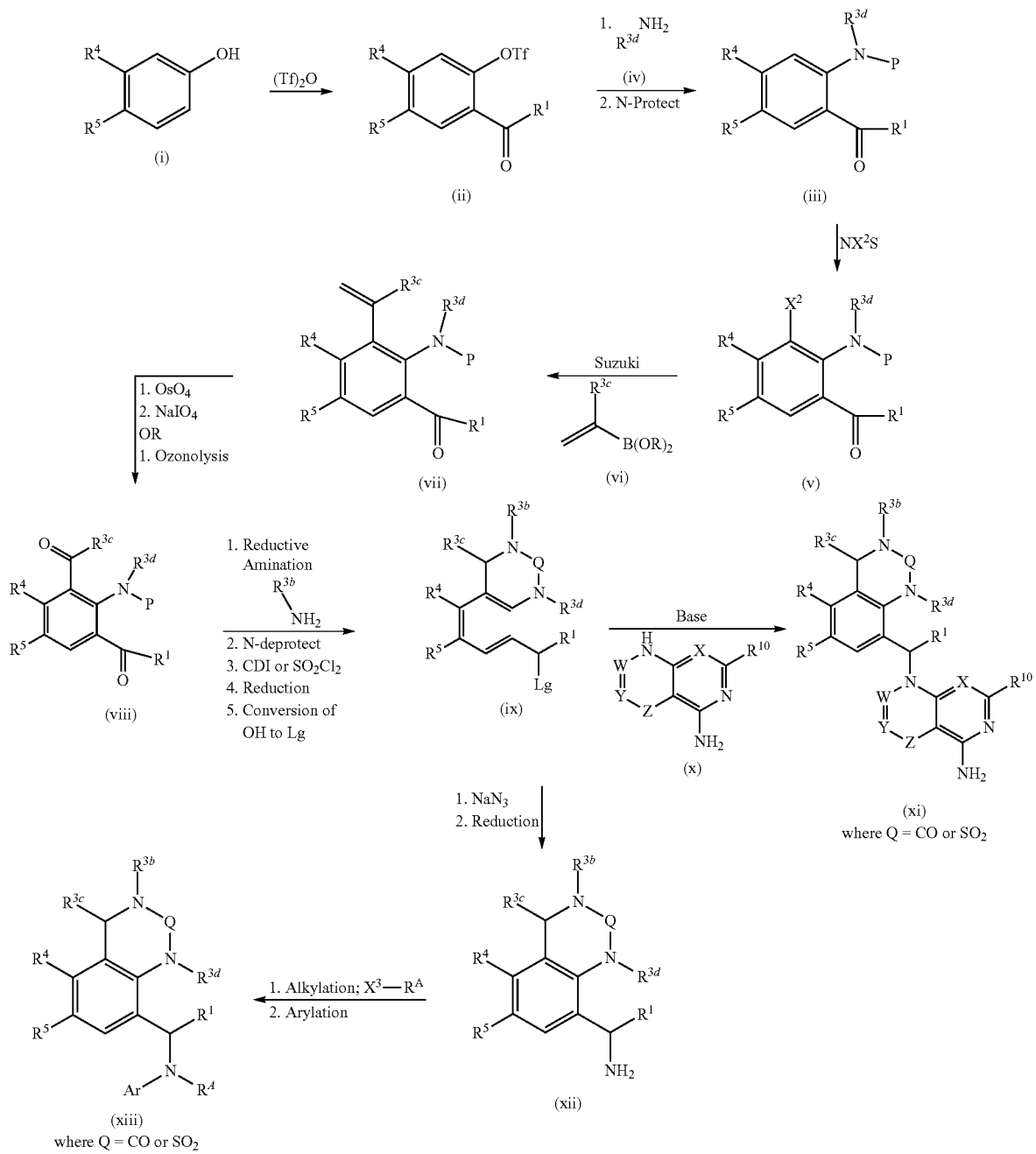

Compounds of Formula I can be formed as shown in Scheme XI. Phenol (i) can reacted with a suitable reagent (e.g., $H_2SO_4$) to form a sulfate which can be chlorinated using standard conditions (e.g., $SOCl_2$) to afford a sulfonylchloride (ii). Reaction of the sulfonylchloride with an amine (iv) can give a sulfonamide (iii). When the amine (iv) contains a second amino group ($U=NPR^{2d}$) the sulfonamide (ii) can be reacted with triflic anhydride to give a triflate and then the amine deprotected and cyclized by heating in the presence of base or under Buchwald conditions (e.g., in the presence of a palladium(0) catalyst, such as tetrakis(triphenylphosphine) palladium(0) and a base (e.g., an alkoxide base)) to give the bicyclic compound (vi). The carbonyl of compound (vi) can be reduced with a suitable reagent, such as $NaBH_4$, to give an alcohol which can be further converted to an intermediate (vii) bearing a leaving group, (e.g., Lg is chloride via reaction with $SO_2Cl_2$ or cyanuric chloride or mesylate via reaction with methanesulfonic anhydride). The intermediate compound (vii) can be converted to compounds of Formula I by similar methods as shown for intermediates bearing leaving groups in Schemes I and II. Alternatively, when the amine (iv) contains an alcohol group (U=OH) the sulfonamide (viii) can be intramolecularly cyclized to an ether (ix) using standard Mitsunobu conditions (e.g., DEAD, $Ph_3P$). The ketone of compound (ix) can be reduced with a suitable reagent, such as NaBH$_4$, to give an alcohol which can be further converted to an intermediate (x) bearing a leaving group, (e.g., Lg is chloride via reaction with SO$_2$Cl$_2$ or cyanuric chloride or mesylate via reaction with methanesulfonic anhydride). The intermediate compound (x) can be converted to compounds of Formula I by similar methods as shown for intermediates bearing leaving groups in Schemes I and II.

Scheme XI

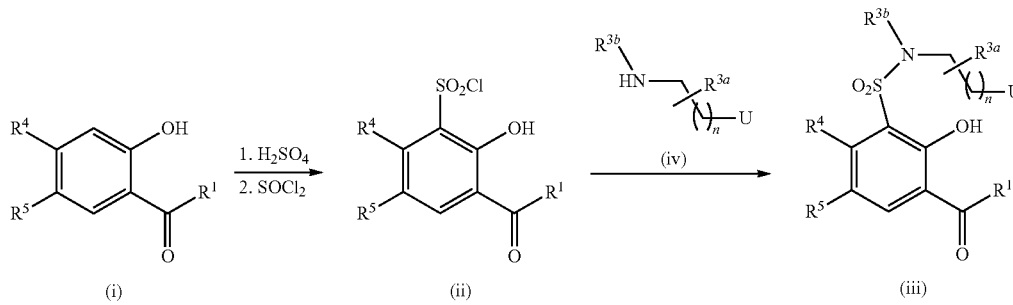

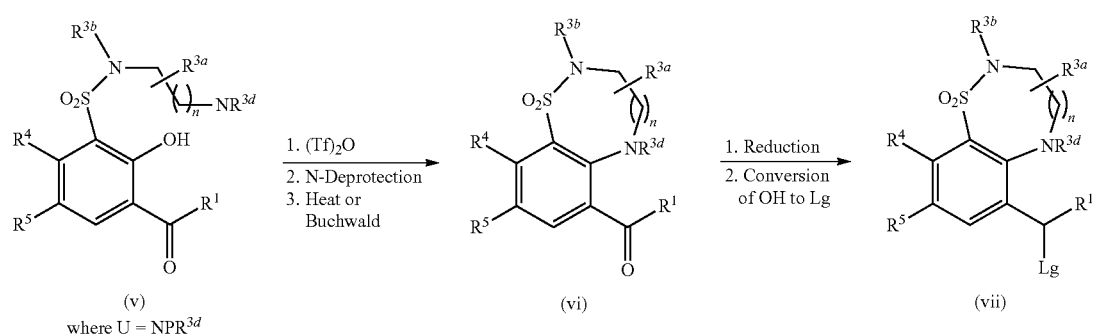

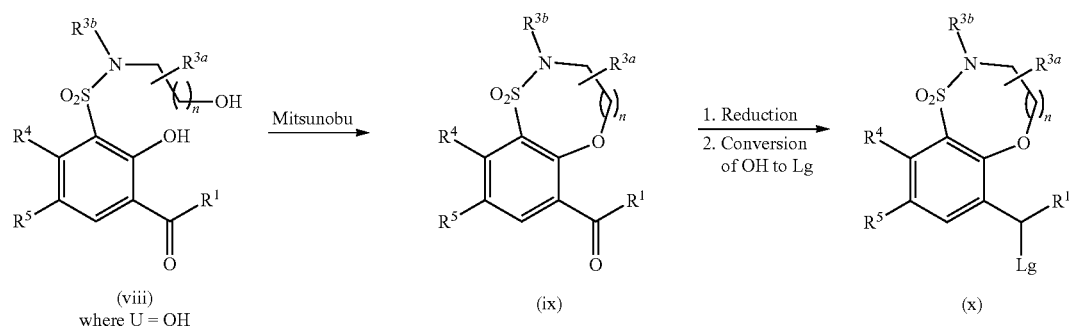

Compounds of Formula I can be formed as shown in Scheme XII. Carbonyl derivative (i) can be reductively aminated with an amine (e.g., $NH_2R^{3b}$ in the presence of NaCNBH$_3$) and then reacted with a sulfonylchloride (e.g., $ClSO_2QCl$, where $Q=(CR^{3a}R^{3a})_n$) to give the corresponding sulfonamide (ii). Deprotection of the nitrogen and subsequent cyclization followed by reduction of the carbonyl with a suitable reagent, such as NaBH$_4$, can give an alcohol which can be further converted to an intermediate (iii) bearing a leaving group, (e.g., Lg is chloride via reaction with $SO_2Cl_2$ or cyanuric chloride or mesylate via reaction with methanesulfonic anhydride). The intermediate compound (iii) can be converted to compounds of Formula I by similar methods as shown for intermediates bearing leaving groups in Schemes I and II. Alternatively, the amine of compound (i) can be deprotected and reacted with a sulfonylchloride (e.g., $ClSO_2QCl$, where $Q=(CR^{3a}R^{3a})_n$) to give the corresponding sulfonamide (iv). Reductive amination of the sulfonamide (iv) with an amine (e.g., $NH_2R^{3b}$ in the presence of a reducing agent, such as NaCNBH$_3$) followed by intramolecular cyclization and subsequent reduction with a suitable reagent, such as NaBH$_4$, to give an alcohol which can be further converted to an intermediate (v) bearing a leaving group, (e.g., Lg is chloride via reaction with $SO_2Cl_2$ or cyanuric chloride or mesylate via reaction with methanesulfonic anhydride). The intermediate compound (v) can be converted to compounds of Formula I by similar methods as shown for intermediates bearing leaving groups in Schemes I and II.

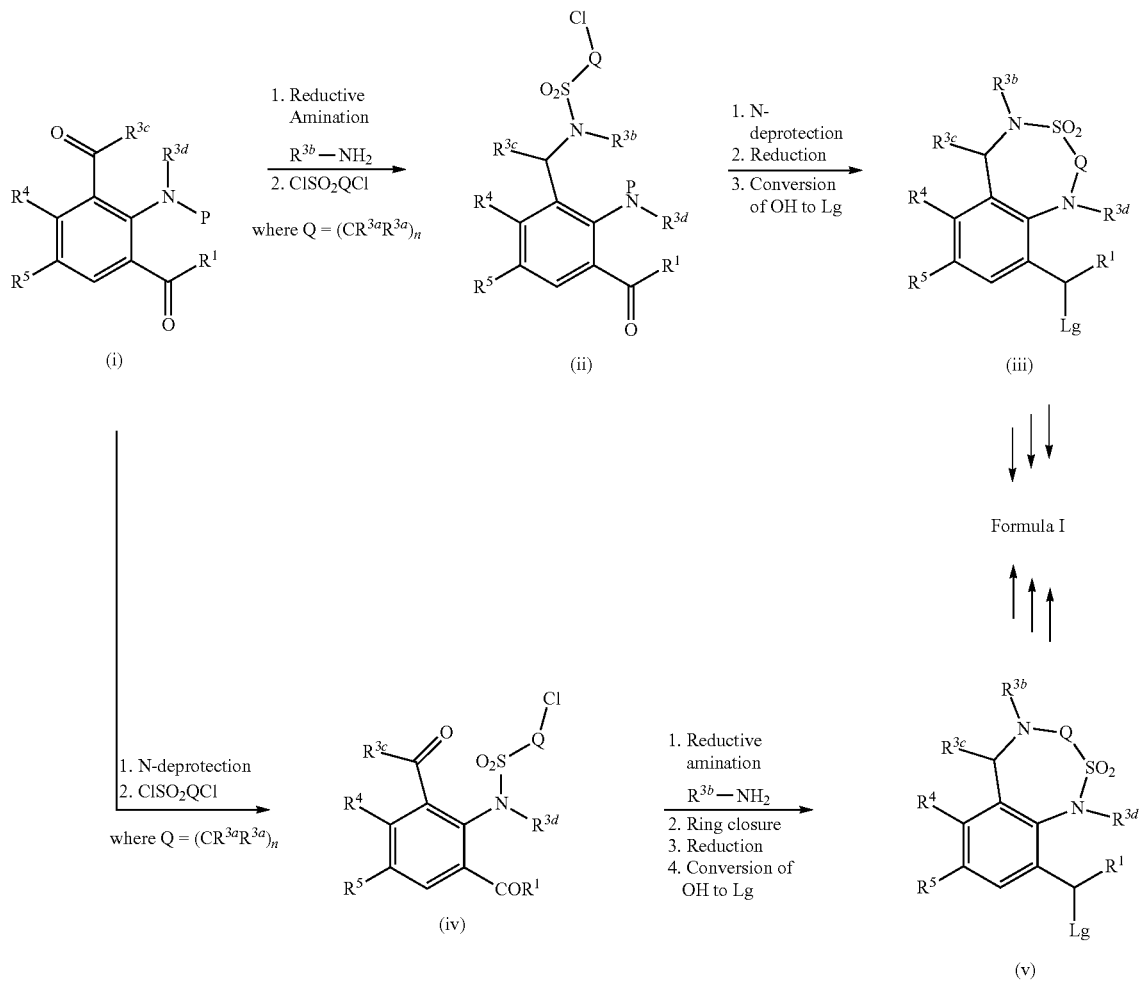

Scheme XII

Compound of Formula I can be synthesized from an acid chloride compound (i) as illustrated in Scheme XIII. Condensation of an acid chloride (i) with malononitrile in the presence of a base, such as sodium hydride, can give a dicyanoenol intermediate, which can be O-methylated with an appropriate reagent, such as dimethyl sulfate in the presence of an appropriate base, such as sodium bicarbonate, to yield an enol ether (ii). Reaction of enol ether (ii) with hydrazine dihydrochloride in the presence of a suitable base, such as triethylamine, can give a pyrazole compound (iii). Pyrazole compound (iii) can then be reacted with formamide to give pyrazolopyrimidine (iv). Finally, compound (iv) can be reacted with appropriate compound bearing a leaving group (v) under basic conditions to give a compound of Formula I (vi).

Scheme XIII

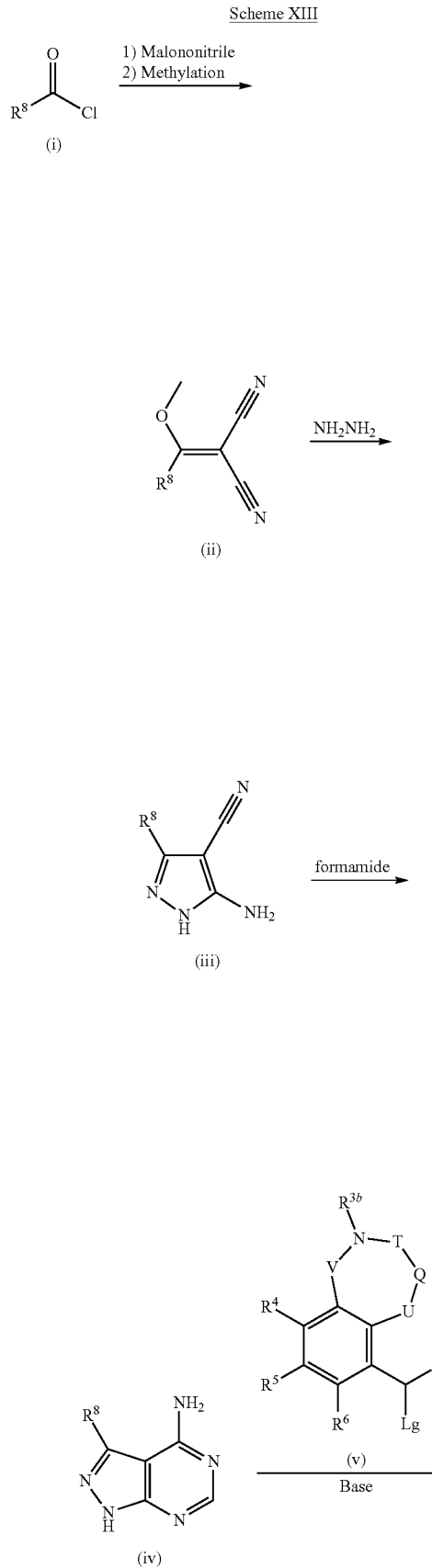

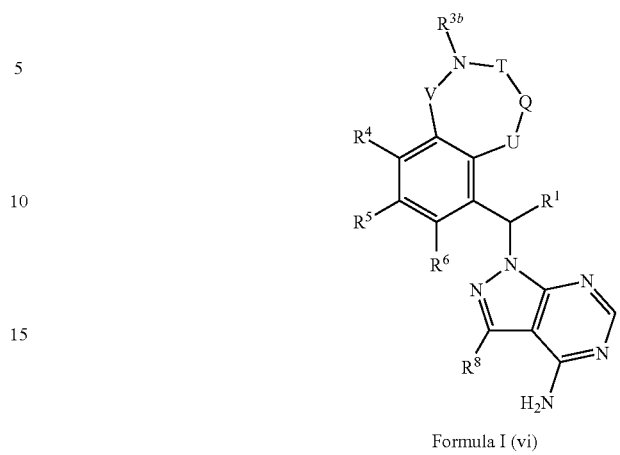

Formula I (vi)

Compounds of Formula I can also be formed as shown in Scheme XIV. The compound (i) can be reacted with a halo-substituted heterocycle (ii) (e.g., 3-iodo-1H-pyrazolo[3,4-d]pyrimidin-4-amine or 4-amino-6-iodopyrido[2,3-d]pyrimidin-5(8H)-one) under basic conditions (e.g., NaH or CsCO$_3$ or K$_2$CO$_3$) to give compound (iii) where X$^2$=Cl, Br, or I. The halo group of (iii) can be coupled to R$^3$-M, where M is a boronic acid, boronic ester or an appropriately substituted metal (e.g., R$^8$-M is R$^8$—B(OH)$_2$, R$^8$—Sn(Bu)$_4$, or Zn—R$^8$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, R$^8$-M can be a cyclic amine (where M is H and attached to the amine nitrogen) with coupling to compound (iii) being performed by heating in base or under Buchwald conditions (e.g., in the presence of a palladium(0) catalyst, such as tetrakis(triphenylphosphine)palladium(0) and a base (e.g., an alkoxide base)) to afford compounds of Formula I (iv).

Scheme XIV

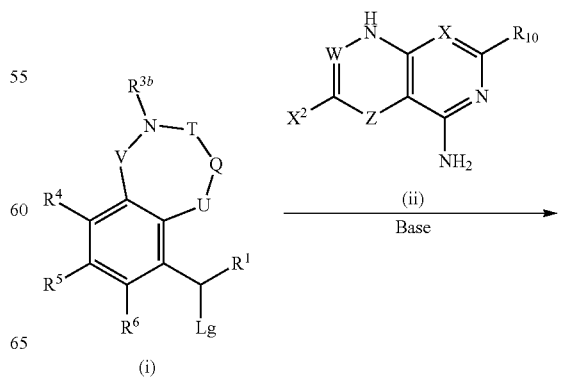

-continued

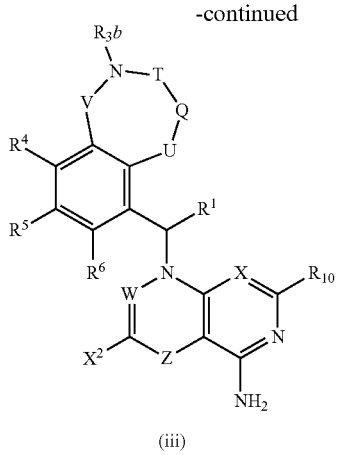

(iii)

Suzuki, Stille, Negishi or Buchwald →

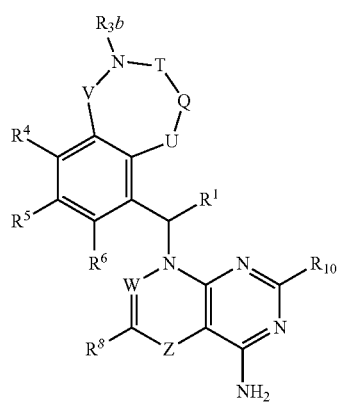

Formula I (iv)

Compounds of Formula I can be synthesized from commercially available 4-aminopyrido[2,3-d]pyrimidine-5(8H)-one (i) as shown in Scheme XV. Halogenation of compound (i) with suitable reagents, such as N-halo succinamide ($NX^2S$, where $X^2$=Cl, Br or I) can give the corresponding halo compound (ii). Reaction of the halo derivative (ii) with a compound (iii) bearing a leaving group in the presence of a suitable base (e.g. diisopropylethylamine) can give compound (iv). The halo compound (iv) can be coupled to $R^{8a}$-M, where M is a boronic acid, boronic ester or an appropriately substituted metal (e.g., $R^{8a}$-M is $R^{8a}$—B(OH)$_2$, $R^{8a}$—Sn (Bu)$_4$, or Zn—$R^{8a}$), under standard Suzuki conditions or standard Stille conditions (e.g., in the presence of a palladium (0) catalyst, such as tetrakis(triphenylphosphine)palladium (0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, $R^{8a}$-M can be a cyclic amine (where M is H and attached to the amine nitrogen) with coupling to compound (iii) being performed by heating in base or under Buchwald conditions (e.g., in the presence of a palladium(0) catalyst, such as tetrakis(triphenylphosphine)palladium(0) and a base (e.g., an alkoxide base)) to afford compounds of Formula I (v).

Scheme XV

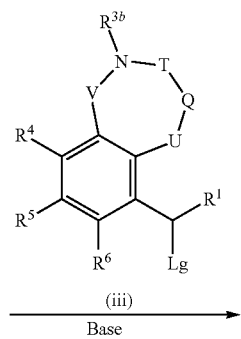

$NX^2S$ ⎡ L = H (i)
         ⎣ L = $X^2$ (ii)

(iii) / Base →

(iv) Suzuki, Stille, Negishi, Buchwald →

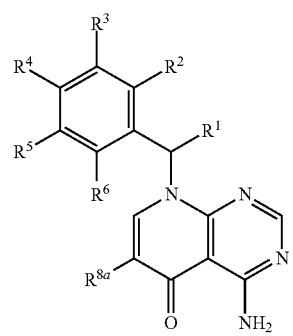

Formula I (v)

Compounds of Formula I can also be formed as shown in Scheme XVI. The compound (i) can be reacted with a halo-substituted heterocycle (ii) (e.g., 6-chloro-9H-purine) under basic conditions (e.g., NaH or $CsCO_3$ or $K_2CO_3$) to give a compound of Formula I (ii).

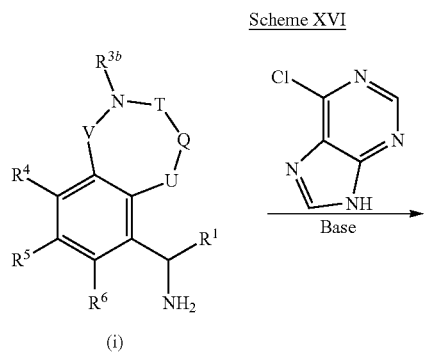

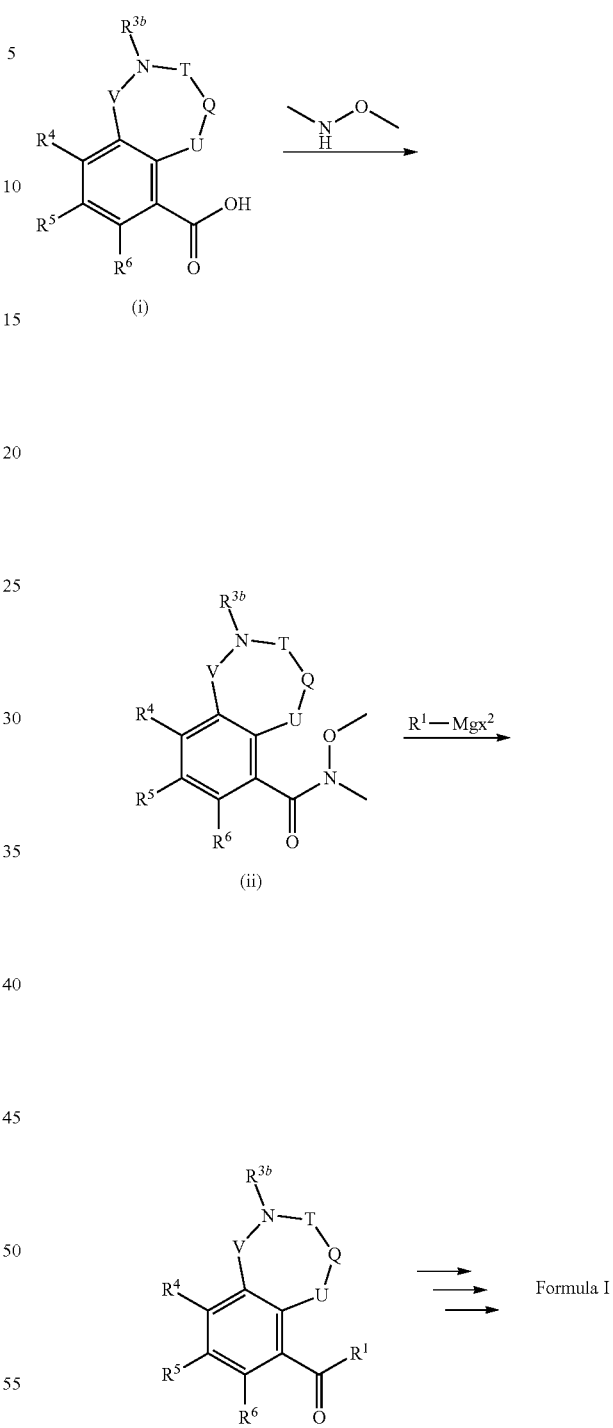

Ketones which can be used in the processes of Scheme I, II and III, can also be formed as shown in Scheme XVII. The carboxylic acid (i) can be activated with a coupling agent (e.g. HBTU or HATU) and then reacted with N,O-dimethylhydroxylamine to give a N-methoxy-N-methylcarboxamide. Reaction of compound (ii) with a Grignard reagent of formula $R^1$-$MgX^2$ ($X^2$=halo) can give ketone (iii). The ketone (iii) can be transformed using similar methods as shown in Scheme I, II and III to afford compounds of Formula I.

Compounds of Formula I can also be formed as shown in Scheme XVIII. The compound (i) can be reacted with a halo-substituted heterocycle (ii) (e.g., 4-chloropyrido[3,2-d]pyrimidine [Anichem, cat #: N10204] and 7-chlorothiazolo[5,4-d]pyrimidine) [Combi-Blocks, cat #: QA2711] under basic conditions (e.g., NaH or $CsCO_3$ or $K_2CO_3$) to give a compound of Formula I (ii).

Scheme XVIII

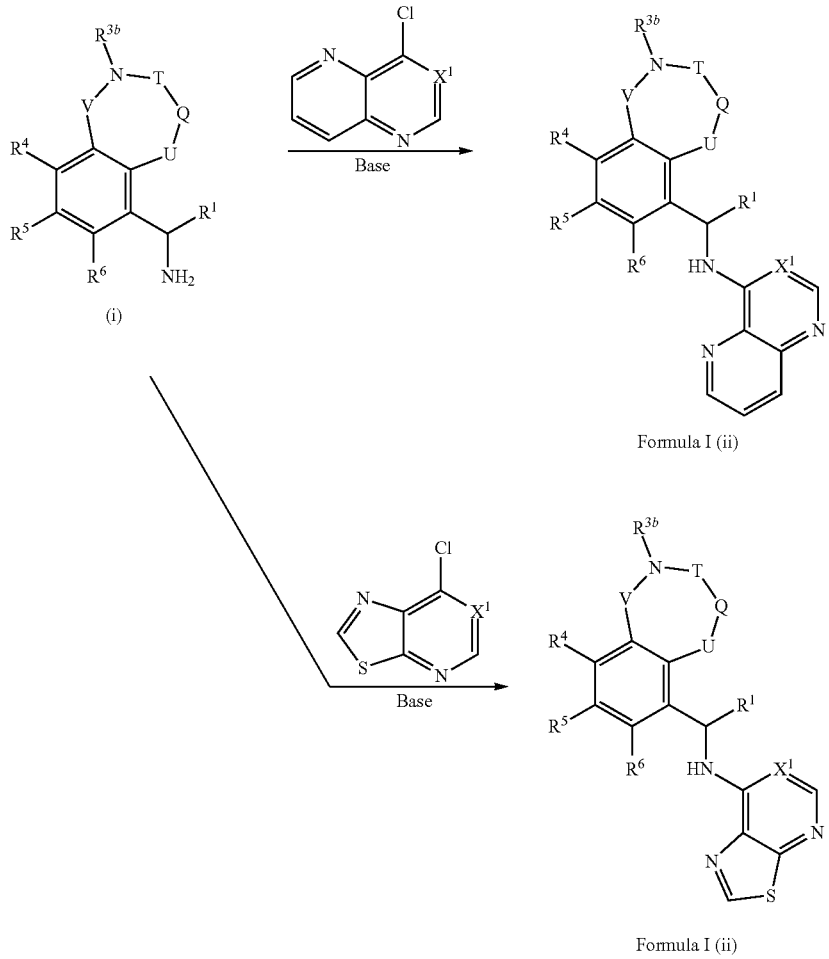

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

Further examples of PI3K-associated diseases include idiopathic thrombocytopenic purpura (ITP), autoimmune hemolytic anemia (AIHA), vasculitis, systemic lupus erythematosus, lupus nephritis, pemphigus, membranous nephropathy, chronic lymphocytic leukemia (CLL), Non-Hodgkin lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, or germinal center B cell (GCB) diffuse large B cell lymphoma.

In some embodiments, the ITP is relapsed ITP. In some embodiments, the ITP is refractory ITP.

In some embodiments, the method is a method of treating autoimmune hemolytic anemia (AIHA).

In some embodiments, the method is a method of treating vasculitis. In some embodiments, the vasculitis is Behçet's disease, Cogan's syndrome, giant cell arteritis, polymyalgia rheumatica (PMR), Takayasu's arteritis, Buerger's disease (thromboangiitis obliterans), central nervous system vasculitis, Kawasaki disease, polyarteritis nodosa, Churg-Strauss syndrome, mixed cryoglobulinemia vasculitis (essential or hepatitis C virus (HCV)-induced), Henoch-Schönlein purpura (HSP), hypersensitivity vasculitis, microscopic polyangiitis, Wegener's granulomatosis, or anti-neutrophil cytoplasm antibody associated (ANCA) systemic vasculitis (AASV). In some embodiments, the method is a method of treating nephritis.

In some embodiments, the method of treating non-Hodgkin lymphoma (NHL) is relapsed or refractory NHL or recucurrent follicular NHL.

In some embodiments, the present application provides a method of treating an aggressive lymphoma (e.g., germinal center B cell-like (GCB) or activated B cell-like (ABC)) in a patient, comprising administering a therapeutic amount of any of the compounds described herein to said patient, or a pharmaceutically acceptable salt thereof.

In some embodiments, the present application provides a method of treating acute myeloid leukemia in a patient, comprising administering a therapeutic amount of any of the compounds described herein to said patient, or a pharmaceutically acceptable salt thereof.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, bendamustine (Treanda), ofatumumab, and GS-1101 (also known as CAL-101).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib).

Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PI3K labeling and competition assays, compounds that incorporate $^{3}$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^{3}$H, $^{14}$C, $^{125}$I, $^{35}$S and $^{82}$Br. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. Salt stoichiometry which is indicated in any of the products below is meant only to indicate a probable stoichiometry, and should not be construed to exclude the possible formation of salts in other stoichiometries.

Example 1 tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate

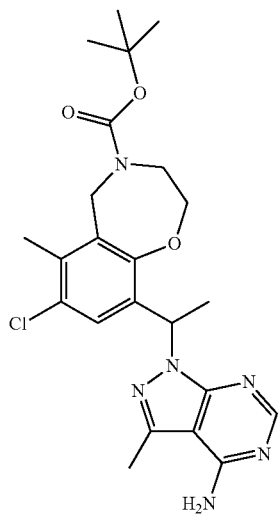 [SMILES: Cc1c(Cl)cc(C(C)n2nc(C)c3c(N)ncnc32)c2c1CN(C(=O)OC(C)(C)C)CCO2]

Step 1. tert-Butyl [2-(6-acetyl-2-bromo-4-chloro-3-methylphenoxy)ethyl]carbamate

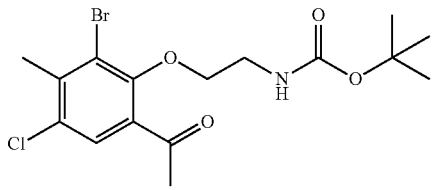 [SMILES: CC(=O)c1cc(Cl)c(C)c(Br)c1OCCNC(=O)OC(C)(C)C]

A suspension of 1-(3-bromo-5-chloro-2-hydroxy-4-methylphenyl)ethanone (8.0 g, 30 mmol) in methylene chloride (304 mL) was heated with a heat gun to dissolve the solids and cooled to 0° C. To the mixture was added triphenylphosphine (11 g, 43 mmol) and tert-butyl (2-hydroxyethyl)carbamate (9.4 mL, 61 mmol). Diisopropyl azodicarboxylate (8.4 mL, 43 mmol) was added dropwise. The mixture was stirred for 23 hours at room temperature. The reaction mixture was poured into water and extracted with methylene chloride. The organic layer was separated, washed with brine, dried with sodium sulfate, filtered, and concentrated. The oil was dissolved in methylene chloride and was purified on silica using ethyl acetate in hexanes (0-25%) to give the desired compound (7.3 g, 59%). LCMS calculated for $C_{16}H_{21}BrClNO_4Na$ (M+Na)$^+$: m/z=428.0, 430.0; found: 428.0, 430.0.

Step 2. tert-Butyl [2-(6-acetyl-4-chloro-3-methyl-2-vinylphenoxy)ethyl]carbamate

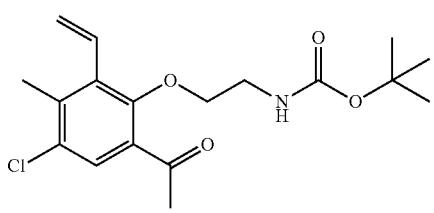 [SMILES: C=Cc1c(C)c(Cl)cc(C(C)=O)c1OCCNC(=O)OC(C)(C)C]

A mixture of tert-butyl [2-(6-acetyl-2-bromo-4-chloro-3-methylphenoxy)ethyl]carbamate (6.5 g, 16 mmol), 4,4,5,5-tetramethyl-2-vinyl-1,3,2-dioxaborolane (3.3 mL, 19 mmol), [1,1'-bis(diphenylphosphino)ferrocene]-dichloropalladium (II), complex with dichloromethane (1:1) (600 mg, 0.8 mmol) and potassium carbonate (6.6 g, 48 mmol) in 1,4-dioxane (100 mL), and water (50 mL) was heated at 80° C. for 3 hours and 50° C. overnight. The reaction mixture was cooled to room temperature and extracted with ethyl acetate (3×10 mL). The organic layers were combined and washed with brine, dried over magnesium sulfate, filtered and concentrated under reduced pressure. The residue was purified on a silica gel with ethyl acetate in hexanes (0-25%) to afford the desired compound (4.1 g, 72%). LCMS calculated for $C_{18}H_{24}ClNO_4Na$ (M+Na)$^+$: m/z=376.1; found: 376.0.

Step 3. tert-Butyl [2-(6-acetyl-4-chloro-2-formyl-3-methylphenoxy)ethyl]carbamate

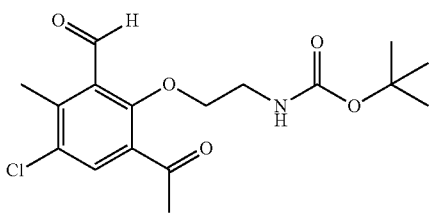 [SMILES: CC(=O)c1cc(Cl)c(C)c(C=O)c1OCCNC(=O)OC(C)(C)C]

tert-Butyl [2-(6-acetyl-4-chloro-3-methyl-2-vinylphenoxy)ethyl]carbamate (4.1 g, 12 mmol) was dissolved in tetrahydrofuran (300 mL) and 0.157 M osmium tetraoxide in water (10 mL) was added followed by a solution of sodium metaperiodate (7.4 g, 35 mmol) in water (20 mL). The reaction was stirred at 60° C. for 2 hours. Additional 0.157 M osmium tetraoxide in water (10 mL) and a solution of sodium metaperiodate (7.4 g, 35 mmol) in water (20 mL) were added and the mixture was heated at 60° C. for 2 more hours. The mixture was poured into ethyl acetate and washed with water, brine, dried over sodium sulfate, filtered and evaporated. Purification on silica gel using ethyl acetate in hexanes (0-12%) gave the desired compound (3.0 g, 73%) (note: elutes as 2 separate peaks in both normal and reversed phase chromatography). LCMS calculated for $C_{17}H_{22}ClNO_5Na$ (M+Na)$^+$: m/z=378.1; found: 378.0.

Step 4. 1-(7-Chloro-6-methyl-2,3-dihydro-1,4-benzoxazepin-9-yl)ethanone

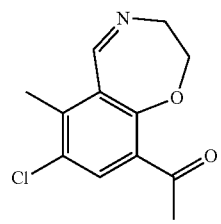 [SMILES: CC(=O)c1cc(Cl)c(C)c2c1OCCN=C2]

tert-Butyl [2-(6-acetyl-4-chloro-2-formyl-3-methylphenoxy)ethyl]carbamate (270 mg, 0.76 mmol) was stirred in 4.0 M hydrogen chloride in dioxane (5.0 mL) at room temperature for 1 hour and evaporated. Tetrahydrofuran was added and the mixture was evaporated to give the desired compound (180 mg, 100%). LCMS calculated for $C_{12}H_{13}ClNO_2$ (M+H)$^+$: m/z=238.1; found: 238.0.

Step 5. 1-(7-Chloro-6-methyl-2,3,4,5-tetrahydro-1,4-benzoxazepin-9-yl)ethanol

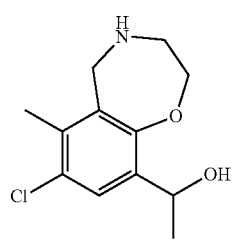 [SMILES: Cc1c(Cl)cc(C(C)O)c2c1CNCCO2]

1-(7-Chloro-6-methyl-2,3-dihydro-1,4-benzoxazepin-9-yl)ethanone (630 mg, 2.6 mmol) was stirred in methanol (20 mL) and cooled to 0° C. Sodium tetrahydroborate (150 mg, 4.0 mmol) was added. The mixture was stirred for 1 hour at room temperature and evaporated. The mixture was extracted with ethyl acetate, washed with saturated sodium bicarbonate, brine, dried over sodium sulfate, filtered and evaporated gave the desired compound (580 mg, 90%). LCMS calculated for $C_{12}H_{17}ClNO_2$ (M+H)$^+$: m/z=242.1; found: 242.0.

Step 6. tert-Butyl 7-chloro-9-(1-hydroxyethyl)-6-methyl-2,3-dihydro-1,4-benzoxazepine-4(5H)-carboxylate

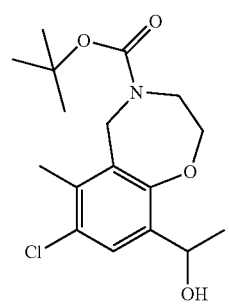 [SMILES: Cc1c(Cl)cc(C(C)O)c2c1CN(C(=O)OC(C)(C)C)CCO2]

1-(7-Chloro-6-methyl-2,3,4,5-tetrahydro-1,4-benzoxazepin-9-yl)ethanol (250 mg, 1.0 mmol) and di-tert-butyldicarbonate (220 mg, 1.0 mmol) were stirred in tetrahydrofuran (12 mL) and N,N-diisopropylethylamine (1.3 mL, 7.2 mmol) was added. The mixture was stirred at room temperature for 1 hour. The mixture was diluted with saturated bicarbonate and extracted with ethyl acetate. The extracts were washed with brine, dried over sodium sulfate, filtered and evaporated to give the crude. Purification on silica gel using ethyl acetate in hexanes 0-35% gave the desired compound (89%). LCMS calculated for $C_{17}H_{24}ClNO_4Na$ (M+Na)$^+$: m/z=364.1; found: 364.0.

Step 7. tert-Butyl 7-chloro-9-(1-chloroethyl)-6-methyl-2,3-dihydro-1,4-benzoxazepine-4(5H)-carboxylate

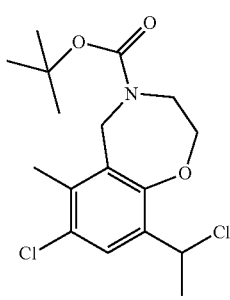 [SMILES: Cc1c(Cl)cc(C(C)Cl)c2c1CN(C(=O)OC(C)(C)C)CCO2]

A mixture of tert-butyl 7-chloro-9-(1-hydroxyethyl)-6-methyl-2,3-dihydro-1,4-benzoxazepine-4(5H)-carboxylate (280 mg, 0.82 mmol) and N,N-dimethylformamide (30 μL) in methylene chloride (6 mL) was stirred and thionyl chloride (120 μL, 1.7 mmol) was added dropwise. The mixture was stirred at room temperature for 20 minutes. The mixture was diluted with methylene chloride, washed with saturated sodium bicarbonate, water, brine, dried over sodium sulfate, filtered and concentrated to give the desired product (295 mg, 100%).

81

Step 8. tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate

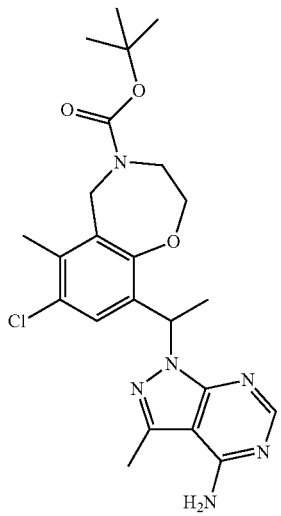 [SMILES: Cc1c(Cl)cc(C(C)n2nc(C)c3c(N)ncnc32)c2c1CN(C(=O)OC(C)(C)C)CCO2]

Cesium carbonate (500 mg, 2 mmol) was added to a mixture of 3-methyl-1H-pyrazolo[3,4-d]pyrimidin-4-amine (150 mg, 0.98 mmol) in N,N-dimethylformamide (30 mL) and stirred for 10 minutes. To this was added tert-butyl 7-chloro-9-(1-chloroethyl)-6-methyl-2,3-dihydro-1,4-benzoxazepine-4(5H)-carboxylate (290 mg, 0.82 mmol) in N,N-dimethylformamide (1 mL) and the reaction was stirred at 80° C. for 1 hour. The mixture was diluted with ethyl acetate and washed with water and brine. The extracts were dried over sodium sulfate, filtered and evaporated. The crude was dissolved in methylene chloride and filtered to remove insoluble material (unwanted regioisomer). Purification on silica gel using ethyl acetate in hexanes (0-100%) followed by methanol in ethyl acetate (0-15%) gave the desired compound (240 mg, 62%). LCMS calculated for $C_{23}H_{30}ClN_6O_3(M+H)^+$: m/z=473.2; found: 473.2. $^1$H NMR (300 MHz, CD$_3$OD): δ 8.14 (s, 1 H), 7.29 (m, 1 H), 6.32 (m, 1 H), 4.70 (m, 1 H), 4.40 (m, 1 H), 3.83 (m, 2 H), 3.57 (m, 2 H), 2.58 (s, 3 H), 2.48 (m, 3 H), 1.78 (m, 3 H), 1.39 (, 9H).

Example 2

1-[1-(7-Chloro-6-methyl-2,3,4,5-tetrahydro-1,4-benzoxazepin-9-yl)ethyl]-3-methyl-1H-pyrazolo[3,4-d]pyrimidin-4-amine bis(trifluoroacetate)

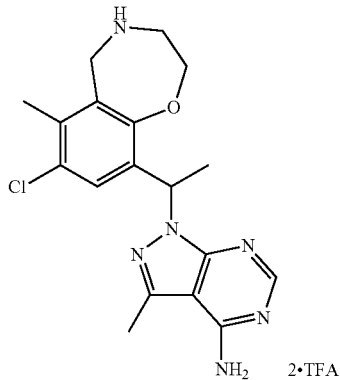 [SMILES: Cc1c(Cl)cc(C(C)n2nc(C)c3c(N)ncnc32)c2c1CNCCO2]

82 tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) was stirred in 4 N HCl in dioxane (1 mL), and then the solvent was evaporated. Purification by preparative LCMS (pH 2) gave the desired compound (1.8 mg, 7%). LCMS calculated for $C_{18}H_{22}ClN_6O$ (M+H)$^+$: m/z=373.2; found: 373.1.

Example 3 tert-Butyl 3-[9-[1-(4-amino-3-methyl-1H-pyrazolo[3,4-d]pyrimidin-1-yl)ethyl]-7-chloro-6-methyl-2,3-dihydro-1,4-benzoxazepin-4(5H)-yl]azetidine-1-carboxylate

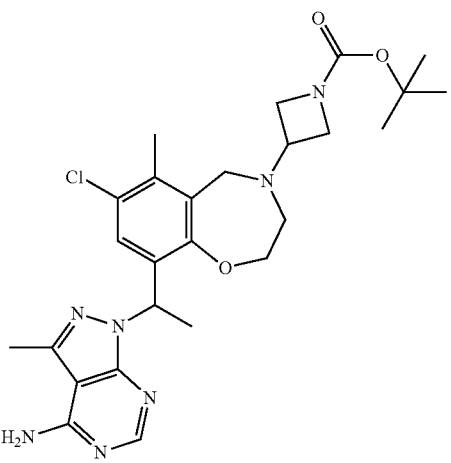 [SMILES: Cc1c(Cl)cc(C(C)n2nc(C)c3c(N)ncnc32)c2c1CN(C1CN(C(=O)OC(C)(C)C)C1)CCO2]

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (100 mg, 0.2 mmol) was treated with 4 N HCl in dioxane (1 mL), and then the solvent was evaporated. The residue was stirred in methanol (5 mL) and tert-butyl 3-oxoazetidine-1-carboxylate (140 mg, 0.84 mmol) was added. Sodium cyanoborohydride (120 mg, 1.9 mmol) was added and the mixture was warmed to 60° C. for 1.5 hours. Purification by preparative LCMS (pH 10) gave the desired compound (3.3 mg, 10%). LCMS calculated for $C_{26}H_{35}ClN_7O_3$ (M+H)$^+$: m/z=528.2; found: 528.3. $^1$H NMR (300 MHz, CD$_3$OD): δ 8.14 (s, 1 H), 7.33 (s, 1 H), 6.33 (m, 1 H), 4.00 (m, 2 H), 3.82 (m, 1 H), 3.74 (m, 2 H), 3.63 (m, 3 H), 3.41 (m, 1 H), 2.76 (m, 2 H), 2.58 (s, 3 H), 2.37 (s, 3 H), 1.79 (m, 3 H), 1.42 (s, 9H).

Example 4

1-{1-[4-(1-Acetylazetidin-3-yl)-7-chloro-6-methyl-2,3,4,5-tetrahydro-1,4-benzoxazepin-9-yl]ethyl}-3-methyl-1H-pyrazolo[3,4-d]pyrimidin-4-amine

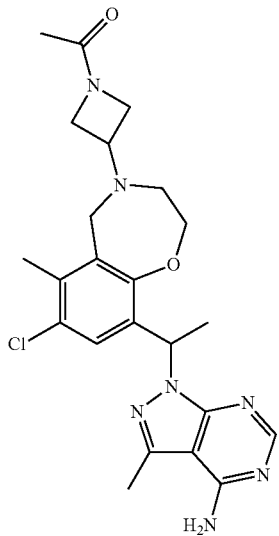 [SMILES: CC(=O)N1CC(N2CCOc3c(C(C)n4nc(C)c5c(N)ncnc54)cc(Cl)c(C)c3C2)C1]

tert-Butyl 3-[9-[1-(4-amino-3-methyl-1H-pyrazolo[3,4-d]pyrimidin-1-yl)ethyl]-7-chloro-6-methyl-2,3-dihydro-1,4-benzoxazepin-4(5H)-yl]azetidine-1-carboxylate (15 mg, 0.035 mmol) was treated with 4 N HCl in dioxane (1 mL), and then the solvent was evaporated. The residue was stirred in N,N-dimethylformamide (0.5 mL) with N,N-diisopropylethylamine (10 µL, 0.06 mmol) and acetic anhydride (20 µL, 0.2 mmol) was added. The mixture was stirred for 5 minutes and diluted with methanol. Purification by preparative LCMS (pH 10) gave the desired compound (2.2 mg, 13%). LCMS calculated for $C_{23}H_{29}ClN_7O_2$ (M+H)$^+$: m/z=470.2; found: 470.2. $^1$H NMR (300 MHz, CD$_3$OD): δ 8.14 (s, 1 H), 7.33 (s, 1 H), 6.33 (m, 1 H), 4.27 (m, 1 H), 4.02 (m, 2 H), 3.80 (m, 1 H), 3.72 (m, 1 H), 3.69 (m, 3 H), 3.48 (m, 1 H), 2.79 (m, 2 H), 2.58 (s, 3 H), 2.38 (s, 3 H), 1.82 (m, 3 H), 1.77 (m, 3 H).

Example 5

1-[1-(7-Chloro-4-cyclobutyl-6-methyl-2,3,4,5-tetrahydro-1,4-benzoxazepin-9-yl)ethyl]-3-methyl-1H-pyrazolo[3,4-d]pyrimidin-4-amine bis(trifluoroacetate)

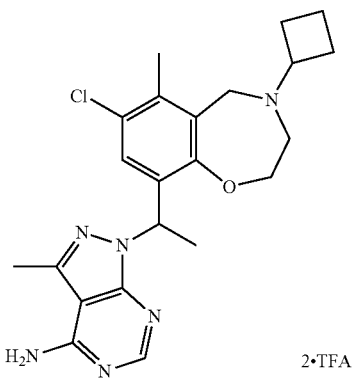 [SMILES: Cc1c(Cl)cc(C(C)n2nc(C)c3c(N)ncnc32)c2c1CN(C1CCC1)CCO2]

The desired compound was prepared according to the procedure of Example 3, using cyclobutanone instead of tert-butyl 3-oxoazetidine-1-carboxylate as the starting material in 50% yield. LCMS calculated for $C_{22}H_{28}ClN_6O$ (M+H)$^+$: m/z=427.2; found: 427.0. $^1$H NMR (300 MHz, CD$_3$OD): δ 8.31 (s, 1 H), 7.61 (s, 1 H), 6.47 (m, 1 H), 4.37 (s, 2 H), 3.89 (m, 1 H), 3.48 (m, 2 H), 2.64 (s, 3 H), 2.45 (m, 4 H), 2.28 (m, 1 H), 1.86 (m, 3 H).

Example 6

1-[1-(7-Chloro-4-cyclopentyl-6-methyl-2,3,4,5-tetrahydro-1,4-benzoxazepin-9-yl)ethyl]-3-methyl-1H-pyrazolo[3,4-d]pyrimidin-4-amine bis(trifluoroacetate)

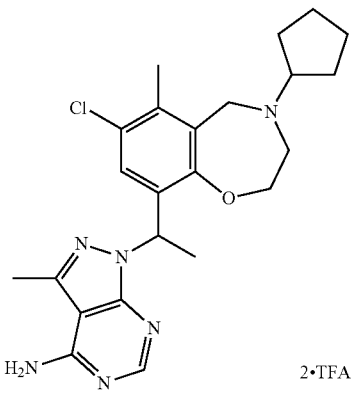 [SMILES: Cc1c(Cl)cc(C(C)n2nc(C)c3c(N)ncnc32)c2c1CN(C1CCCC1)CCO2]

The desired compound was prepared according to the procedure of Example 3, using cyclopentanone instead of tert-butyl 3-oxoazetidine-1-carboxylate as the starting material in 50% yield. LCMS calculated for $C_{23}H_{30}ClN_6O$ (M+H)$^+$: m/z=441.2; found: 441.0. $^1$H NMR (300 MHz, CD$_3$OD): δ 8.31 (s, 1 H), 7.60 (s, 1 H), 6.47 (m, 1 H), 4.52 (br s, 2 H), 3.79 (m, 1 H), 3.62 (m, 2 H), 2.63 (s, 3 H), 2.47 (s, 3 H), 2.03 (m, 3 H), 1.81 (m, 10 H).

Example 7

1-[1-(7-Chloro-4-cyclohexyl-6-methyl-2,3,4,5-tetrahydro-1,4-benzoxazepin-9-yl)ethyl]-3-methyl-1H-pyrazolo[3,4-d]pyrimidin-4-amine bis(trifluoroacetate)

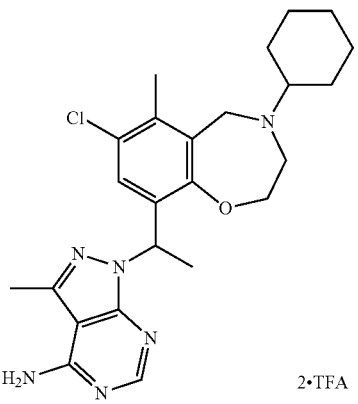 [SMILES: Cc1c(Cl)cc(C(C)n2nc(C)c3c(N)ncnc32)c2c1CN(C1CCCCC1)CCO2]

The desired compound was prepared according to the procedure of Example 3, using cyclohexanone instead of tert-butyl 3-oxoazetidine-1-carboxylate as the starting material in 20% yield. LCMS calculated for $C_{24}H_{32}ClN_6O$ (M+H)$^+$: m/z=455.2; found: 455.2. $^1$H NMR (300 MHz, CD$_3$OD): δ 8.30 (s, 1 H), 7.59 (s, 1 H), 6.48 (m, 1 H), 4.60 (m, 2 H), 4.48 (m, 2 H), 3.75 (m, 1 H), 3.47 (m, 2 H), 2.63 (s, 3 H), 2.48 (s, 3 H), 2.18 (m, 2 H), 2.03 (m, 2 H), 1.85 (m, 3 H), 1.73 (m, 3 H), 1.47 (m, 2 H), 1.29 (m, 1 H).

Example 8

1-{1-[7-Chloro-4-(4-methoxycyclohexyl)-6-methyl-2,3,4,5-tetrahydro-1,4-benzoxazepin-9-yl]ethyl}-3-methyl-1H-pyrazolo[3,4-d]pyrimidin-4-amine bis(trifluoroacetate)

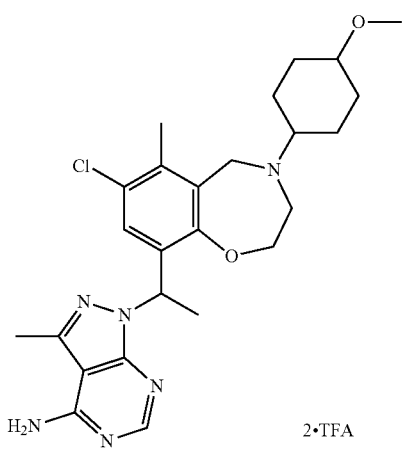

2·TFA

The desired compound was prepared according to the procedure of Example 3, using 4-methoxycyclohexanone instead of tert-butyl 3-oxoazetidine-1-carboxylate as the starting material in 10% yield. LCMS calculated for $C_{25}H_{34}ClN_6O_2$ (M+H)$^+$: m/z=485.2; found: 485.3. $^1$H NMR (300 MHz, CD$_3$OD): δ 8.51 (s, 1 H), 7.56 (s, 1 H), 6.48 (m, 1 H), 4.60 (m, 2 H), 4.48 (m, 2 H), 3.75 (m, 1 H), 3.47 (m, 2 H), 3.30 (m, 4 H), 2.62 (s, 3 H), 2.48 (s, 3 H), 2.20 (m, 2 H), 1.85 (m, 6 H), 1.60 (m, 2 H), 1.29 (m, 1 H).

Example 9

1-[1-(7-Chloro-4,6-dimethyl-2,3,4,5-tetrahydro-1,4-benzoxazepin-9-yl)ethyl]-3-methyl-1H-pyrazolo[3,4-d]pyrimidin-4-amine bis(trifluoroacetate)

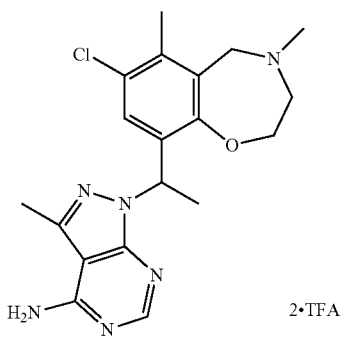

2·TFA tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in 3.0 M formaldehyde in water (0.5 mL, 2 mmol) and formic acid (0.5 mL, 10 mmol) was added. The mixture was heated to 90° C. for 10 minutes. Purification by preparative LCMS (pH 2) gave the desired compound (3.0 mg, 20%). LCMS calculated for $C_{19}H_{24}ClN_6O$ (M+H)$^+$: m/z=387.2; found: 387.1. $^1$H NMR (300 MHz, CD$_3$OD): δ 8.30 (s, 1 H), 7.60 (s, 1 H), 6.47 (m, 1 H), 4.55 (m, 2 H), 4.25 (m, 1 H), 3.60 (m, 3 H), 3.03 (s, 3 H), 2.64 (s, 3 H), 2.47 (s, 3 H), 1.85 (m, 3 H).

Example 10

1-[1-(7-Chloro-4-isopropyl-6-methyl-2,3,4,5-tetrahydro-1,4-benzoxazepin-9-yl)ethyl]-3-methyl-1H-pyrazolo[3,4-d]pyrimidin-4-amine bis(trifluoroacetate)

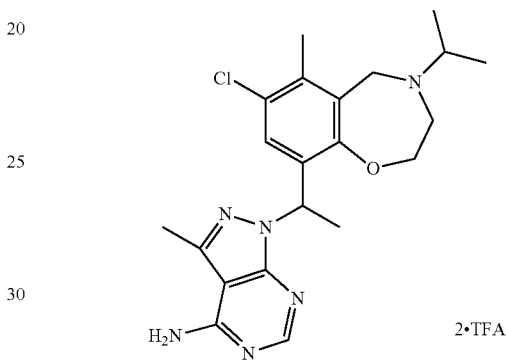

2·TFA tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (15 mg, 0.032 mmol) (treated with 4 N HCl in dioxane, and then the solvent was evaporated) was stirred in acetone (1.0 mL, 14 mmol) and sodium cyanoborohydride (6.0 mg, 0.095 mmol) was added. The mixture was stirred overnight. Purification by preparative LCMS (pH 2) gave the desired compound (7.0 mg, 34%). LCMS calculated for $C_{21}H_{28}ClN_6O$ (M+H)$^+$: m/z=415.2; found: 415.1. $^1$H NMR (300 MHz, CD$_3$OD): δ 8.31 (s, 1 H), 7.59 (s, 1 H), 6.47 (br s, 1 H), 4.49 (m, 4 H), 3.80 (m, 2 H), 3.50 (m, 1 H), 2.64 (s, 3 H), 2.48 (s, 3 H), 1.86 (m, 3 H), 1.46 (m, 6 H).

Example 11

[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]acetonitrile bis(trifluoroacetate)

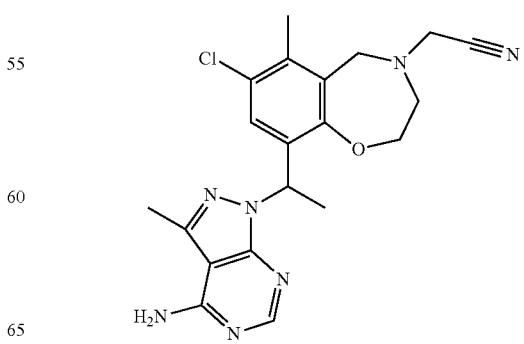

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in N-methylpyrrolidinone (1.0 mL) and N,N-diisopropylethylamine (0.0082 g, 0.063 mmol) was added. Bromoacetonitrile (5.1 mg, 0.042 mmol) was added and the mixture was warmed to 80° C. for 1 hour. Purification by preparative LCMS (pH 2) gave the desired compound (4.9 mg, 40%). LCMS calculated for $C_{20}H_{23}ClN_7O$ (M+H)$^+$: m/z=412.2; found: 412.1. $^1$H NMR (300 MHz, CD$_3$OD): δ 8.30 (s, 1 H), 7.38 (s, 1 H), 6.46 (m, 1 H), 4.03 (m, 1 H), 3.91 (s, 2 H), 3.81 (m, 3 H), 3.05 (m, 2 H), 2.65 (s, 3 H), 2.41 (s, 3 H), 1.83 (m, 3 H).

Example 12

3-[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]-3-oxopropanenitrile trifluoroacetate

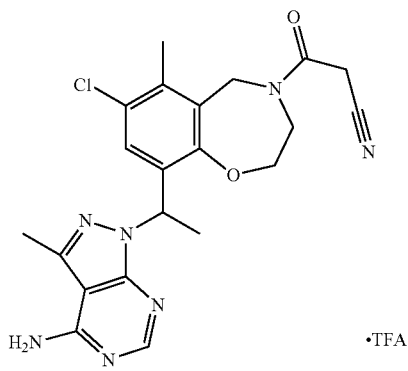 [SMILES: Cc1c(Cl)cc(C(C)n2nc(C)c3c(N)ncnc32)c2c1CN(C(=O)CC#N)CCO2]

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in N-methylpyrrolidinone (1.0 mL) and N,N-diisopropylethylamine (0.0082 g, 0.063 mmol) was added. 3-[(2,5-Dioxopyrrolidin-1-yl)oxy]-3-oxopropanenitrile (0.008 g, 0.042 mmol) was added and the mixture was warmed to 80° C. for 1 hour. Purification by preparative LCMS (pH 2) gave the desired compound (1.8 mg, 20%). LCMS calculated for $C_{21}H_{23}ClN_7O_2$ (M+H)$^+$: m/z=440.2; found: 440.3. $^1$H NMR (300 MHz, CD$_3$OD): δ 8.28 (s, 1 H), 7.38 (s, 1 H), 6.45 (m, 1 H), 4.88 (m, 1 H), 4.54 (m, 1 H), 3.82 (m, 5 H), 2.65 (s, 3 H), 2.56 (s, 3 H), 1.83 (m, 3 H).

Example 13

1-{1-[7-Chloro-6-methyl-4-(methylsulfonyl)-2,3,4,5-tetrahydro-1,4-benzoxazepin-9-yl]ethyl}-3-methyl-1H-pyrazolo[3,4-d]pyrimidin-4-amine trifluoroacetate

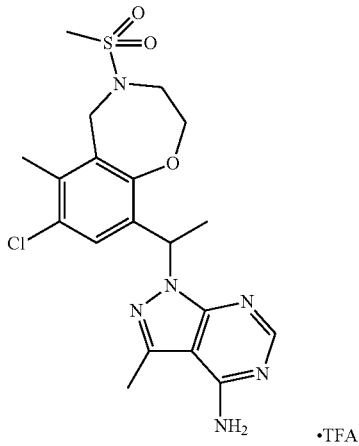 [SMILES: Cc1c(Cl)cc(C(C)n2nc(C)c3c(N)ncnc32)c2c1CN(S(C)(=O)=O)CCO2]

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in tetrahydrofuran (0.5 mL) with N,N-diisopropylethylamine (18 μL, 0.10 mmol) and methanesulfonyl chloride (1.6 μL, 0.021 mmol) was added. The mixture was stirred at room temperature for 20 minutes. Purification by preparative LCMS (pH 2) gave the desired compound (6.3 mg, 53%). LCMS calculated for $C_{19}H_{24}ClN_6O_3S$ (M+H)$^+$: m/z=451.1; found: 451.0. $^1$H NMR (300 MHz, CD$_3$OD): δ 8.29 (s, 1 H), 7.41 (s, 1 H), 6.47 (m, 1 H), 4.62 (m, 1 H), 4.43 (m, 1 H), 4.12 (m, 1 H), 3.74 (m, 3 H), 2.81 (s, 3 H), 2.65 (s, 3 H), 2.44 (s, 3 H), 1.83 (m, 3 H).

Example 14

1-{1-[7-Chloro-6-methyl-4-(phenylsulfonyl)-2,3,4,5-tetrahydro-1,4-benzoxazepin-9-yl]ethyl}-3-methyl-1H-pyrazolo[3,4-d]pyrimidin-4-amine trifluoroacetate

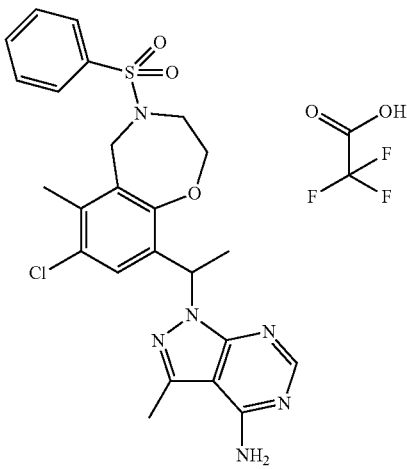 [SMILES: Cc1c(Cl)cc(C(C)n2nc(C)c3c(N)ncnc32)c2c1CN(S(=O)(=O)c1ccccc1)CCO2 ; O=C(O)C(F)(F)F]

The desired compound was prepared according to the procedure of Example 13, using benzenesulfonyl chloride instead of methanesulfonyl chloride in 53% yield. LCMS calculated for $C_{24}H_{26}ClN_6O_3S$ (M+H)+: m/z=513.1; found: 513.0. 1H NMR (300 MHz, CD3OD): δ 8.26 (s, 1 H), 7.70 (m, 2 H), 7.49 (m, 4 H), 6.36 (m, 1 H), 4.60 (m, 1 H), 4.33 (m, 1 H), 3.97 (m, 1 H), 3.62 (m, 3 H), 2.65 (s, 3 H), 2.51 (s, 3 H), 1.77 (m, 3 H).

Example 15

9-[1-(4-Amino-3-methyl-1H-pyrazolo[3,4-d]pyrimidin-1-yl)ethyl]-7-chloro-6-methyl-N-(2-methylphenyl)-2,3-dihydro-1,4-benzoxazepine-4(5H)-carboxamide trifluoroacetate

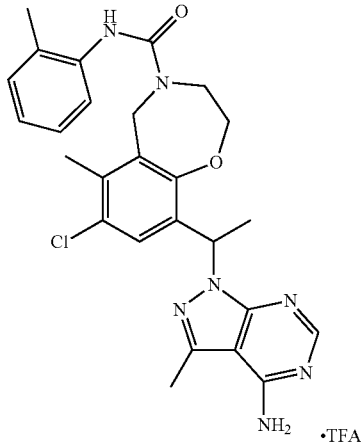 [SMILES: Cc1ccccc1NC(=O)N1CCOc2c(C(C)n3nc(C)c4c(N)ncnc43)cc(Cl)c(C)c2C1]

The desired compound was prepared according to the procedure of Example 13, using 1-isocyanato-2-methylbenzene instead of methanesulfonyl chloride in 27% yield. LCMS calculated for $C_{26}H_{29}ClN_7O_2$ (M+H)+: m/z=506.2; found: 506.0. 1H NMR (300 MHz, CD3OD): δ 8.29 (s, 1 H), 7.36 (s, 1 H), 7.08 (m, 4 H), 6.49 (m, 1 H), 4.80 (m, 1 H), 4.60 (m, 1 H), 4.12 (m, 1 H), 3.88 (m, 3 H), 2.65 (s, 3 H), 2.47 (s, 3 H), 1.95 (s, 3 H), 1.84 (m, 3 H).

Example 16

1-[1-(4-Benzoyl-7-chloro-6-methyl-2,3,4,5-tetrahydro-1,4-benzoxazepin-9-yl)ethyl]-3-methyl-1H-pyrazolo[3,4-d]pyrimidin-4-amine trifluoroacetate

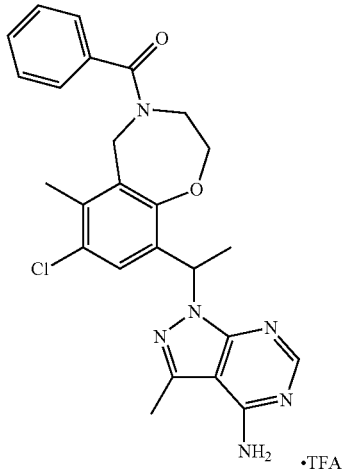 [SMILES: Cc1c(Cl)cc(C(C)n2nc(C)c3c(N)ncnc32)c2c1CN(C(=O)c1ccccc1)CCO2]

The desired compound was prepared according to the procedure of Example 13, using benzoyl chloride instead of methanesulfonyl chloride, Purification by preparative LCMS (pH 2) gave the desired compound (2.1 mg, 17%). LCMS calculated for $C_{25}H_{26}ClN_6O_2$(M+H): m/z=477.2; found: 477.0. 1H NMR (300 MHz, CD3OD): δ 8.27 (s, 1 H), 7.42 (s, 6 H), 6.46 (m, 1 H), 4.89 (m, 1 H), 4.79 (m, 1 H), 4.00 (m, 1 H), 3.77 (m, 3 H), 2.64 (m, 6 H), 1.83 (m, 3 H).

Example 17

1-(1-{7-Chloro-4-[(3,5-dimethylisoxazol-4-yl)sulfonyl]-6-methyl-2,3,4,5-tetrahydro-1,4-benzoxazepin-9-yl}ethyl)-3-methyl-1H-pyrazolo[3,4-d]pyrimidin-4-amine trifluoroacetate

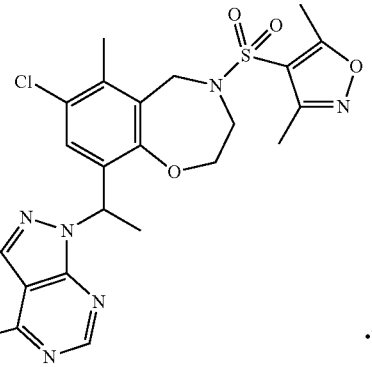

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in methylene chloride (1.0 mL) with N,N-diisopropylethylamine (11 μL, 0.063 mmol) and 3,5-dimethylisoxazole-4-sulfonyl chloride (8.3 mg, 0.042 mmol) was added. The mixture was stirred at room temperature for 20 minutes. Purification by preparative LCMS (pH 2) gave the desired compound (3.1 mg, 20%). LCMS calculated for $C_{23}H_{27}ClN_7O_4S$ (M+H)+: m/z=532.1; found: 532.2. 1H NMR (300 MHz, CD3OD): δ 8.29 (s, 1 H), 7.42 (s, 1 H), 6.38 (m, 1 H), 4.70 (m, 1 H), 4.52 (m, 1 H), 4.12 (m, 1 H), 3.83 (m, 1 H), 3.66 (m, 2 H), 2.65 (s, 3 H), 2.50 (s, 3 H), 2.37 (s, 3 H), 2.24 (s, 3 H), 1.80 (m, 3 H).

Example 18

1-{1-[7-Chloro-4-(cyclopropylsulfonyl)-6-methyl-2,3,4,5-tetrahydro-1,4-benzoxazepin-9-yl]ethyl}-3-methyl-1H-pyrazolo[3,4-d]pyrimidin-4-amine trifluoroacetate

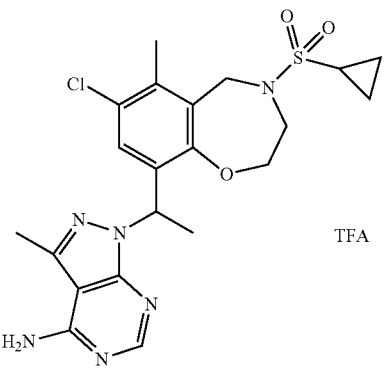 [SMILES: Cc1c(Cl)cc(C(C)n2nc(C)c3c(N)ncnc32)c2c1CN(S(=O)(=O)C1CC1)CCO2]

The desired compound was prepared according to the procedure of Example 17, using cyclopropanesulfonyl chloride instead of methanesulfonyl chloride in 20% yield. LCMS calculated for $C_{21}H_{26}ClN_6O_3S$ (M+H)$^+$: m/z=477.1; found: 477.1. $^1$H NMR (300 MHz, CD$_3$OD): δ 8.29 (s, 1 H), 7.40 (s, 1 H), 6.46 (m, 1 H), 4.68 (m, 1 H), 4.49 (m, 1 H), 4.10 (m, 1 H), 3.80 (m, 1 H), 3.71 (m, 2 H), 2.64 (s, 3 H), 2.45 (s, 3 H), 2.28 (m, 1 H), 1.83 (m, 3 H), 0.93 (m, 4 H).

Example 19

1-[1-(4-Acetyl-7-chloro-6-methyl-2,3,4,5-tetrahydro-1,4-benzoxazepin-9-yl)ethyl]-3-methyl-1H-pyrazolo[3,4-d]pyrimidin-4-amine trifluoroacetate

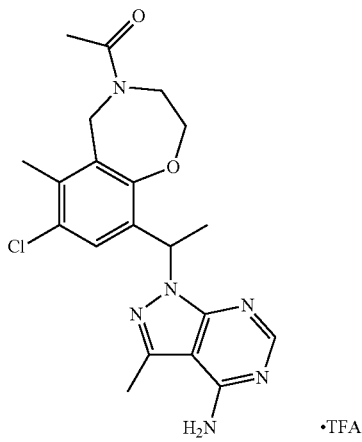 [SMILES: CC(=O)N1CCOc2c(C(C)n3nc(C)c4c(N)ncnc43)cc(Cl)c(C)c2C1]

The desired compound was prepared according to the procedure of Example 1, steps 5-8 using acetic anhydride instead of di-tert-butyldicarbonate in 10% yield. LCMS calculated for $C_{20}H_{24}ClN_6O_2$(M+H)$^+$: m/z=415.2; found: 415.0. $^1$H NMR (300 MHz, CDCl$_3$): δ 8.19 (s, 1 H), 7.43 (s, 1 H), 6.44 (m, 1 H), 4.78 (m, 1 H), 4.58 (m, 1 H), 4.04 (m, 1 H), 3.86 (m, 3 H), 2.67 (s, 3 H), 2.58 (s, 3 H), 2.10 (s, 3 H), 1.84 (m, 3 H).

Example 20

1-[1-(7-Chloro-6-methyl-4-propionyl-2,3,4,5-tetrahydro-1,4-benzoxazepin-9-yl)ethyl]-3-methyl-1H-pyrazolo[3,4-d]pyrimidin-4-amine trifluoroacetate

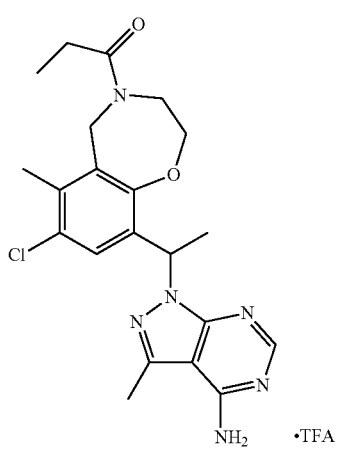 [SMILES: CCC(=O)N1CCOc2c(C(C)n3nc(C)c4c(N)ncnc43)cc(Cl)c(C)c2C1]

The desired compound was prepared according to the procedure of Example 1, steps 5-8 using propanoyl chloride instead of di-tert-butyldicarbonate in 10% yield. LCMS calculated for $C_{21}H_{26}ClN_6O_2$(M+H)$^+$: m/z=429.2; found: 429.0. $^1$H NMR (300 MHz, CD$_3$OD): δ 8.28 (s, 1 H), 7.35 (s, 1 H), 6.49 (m, 1 H), 4.78 (m, 1 H), 4.59 (m, 1 H), 4.10 (m, 1 H), 3.80 (m, 3 H), 2.64 (s, 3 H), 2.56 (s, 3 H), 2.28 (m, 2 H), 1.82 (m, 3 H), 1.03 (m, 3 H).

Example 21

1-{1-[7-Chloro-4-(methoxyacetyl)-6-methyl-2,3,4,5-tetrahydro-1,4-benzoxazepin-9-yl]ethyl}-3-methyl-1H-pyrazolo[3,4-d]pyrimidin-4-amine trifluoroacetate

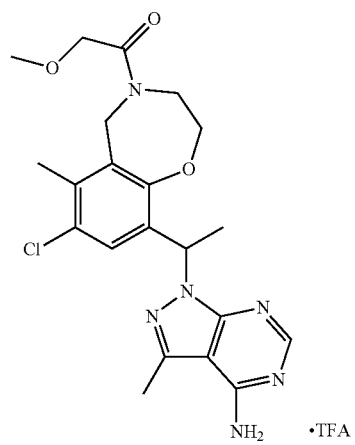 [SMILES: COCC(=O)N1CCOc2c(C(C)n3nc(C)c4c(N)ncnc43)cc(Cl)c(C)c2C1]

The desired compound was prepared according to the procedure of Example 1, steps 5-8 using methoxyacetyl chloride instead of di-tert-butyldicarbonate in 10% yield. LCMS calculated for $C_{21}H_{26}ClN_6O_3$(M+H)$^+$: m/z=445.2; found: 445.0. $^1$H NMR (300 MHz, CD$_3$OD): δ 8.30 (s, 1 H), 7.34 (s, 1 H), 6.49 (m, 1 H), 4.78 (m, 1 H), 4.59 (m, 1 H), 4.10 (m, 4 H), 3.77 (m, 3 H), 3.30 (m, 2 H), 2.65 (s, 3 H), 2.57 (s, 3 H), 1.82 (m, 3 H).

Example 22

1-[1-(7-Chloro-4-isobutyryl-6-methyl-2,3,4,5-tetrahydro-1,4-benzoxazepin-9-yl)ethyl]-3-methyl-1H-pyrazolo[3,4-d]pyrimidin-4-amine trifluoroacetate

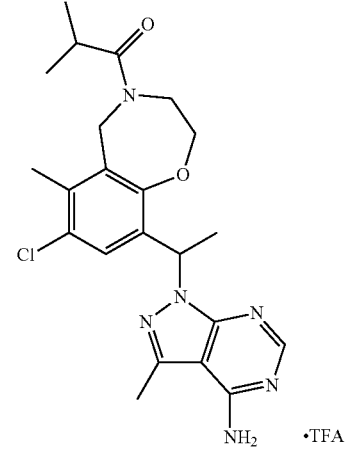 [SMILES: Cc1c(Cl)cc(C(C)n2nc(C)c3c(N)ncnc32)c2c1CN(C(=O)C(C)C)CCO2]

The desired compound was prepared according to the procedure of Example 1, steps 5-8 using isobutyryl chloride instead of di-tert-butyldicarbonate, 23%. LCMS calculated for $C_{22}H_{28}ClN_6O_2(M+H)^+$: m/z=443.2; found: 443.0. $^1$H NMR (300 MHz, CD$_3$OD): δ 8.28 (s, 1 H), 7.34 (s, 1 H), 6.45 (m, 1 H), 4.75 (m, 1 H), 4.55 (m, 1 H), 4.10 (m, 1 H), 3.80 (m, 3 H), 2.80 (m, 1 H), 2.63 (s, 3 H), 2.56 (s, 3 H), 1.82 (m, 3 H), 1.00 (m, 6 H).

Example 23

2-[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]-1,3-thiazole-5-carbonitrile trifluoroacetate

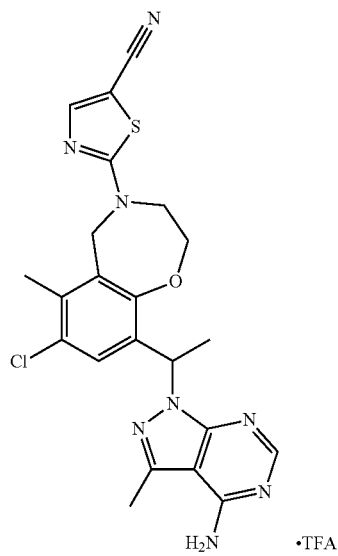 [SMILES: Cc1c(Cl)cc(C(C)n2nc(C)c3c(N)ncnc32)c2c1CN(c1ncc(C#N)s1)CCO2]

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate (10 mg, 0.02 mmol) (treated with 4 N HCl in dioxane, and then the solvent was evaporated) was stirred in NMP and 2-chloro-1,3-thiazole-5-carbonitrile (10 mg, 0.07 mmol) was added. The mixture was heated to 130° C. for 1 hour. Purification by preparative LCMS (pH 10) gave the desired compound (3.2 mg, 30%). LCMS calculated for $C_{22}H_{22}ClN_8OS$ (M+H)$^+$: m/z=481.1; found: 481.1. $^1$H NMR (300 MHz, CD$_3$OD): δ 8.14 (s, 1 H), 7.74 (s, 1 H), 7.31 (s, 1 H), 6.31 (m, 1 H), 4.99 (m, 1 H), 4.78 (m, 1 H), 3.98 (m, 3 H), 3.75 (m, 1 H), 2.58 (m, 6 H), 1.77 (m, 3 H).

Example 24

1-[1-(7-Chloro-6-methyl-4-pyrazin-2-yl-2,3,4,5-tetrahydro-1,4-benzoxazepin-9-yl)ethyl]-3-methyl-1H-pyrazolo[3,4-d]pyrimidin-4-amine bis(trifluoroacetate)

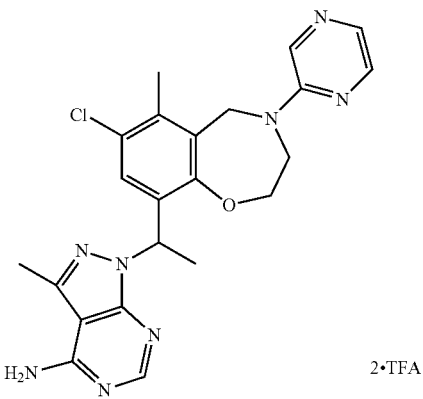 [SMILES: Cc1c(Cl)cc(C(C)n2nc(C)c3c(N)ncnc32)c2c1CN(c1cnccn1)CCO2]

The desired compound was prepared according to the procedure of Example 23, using 2-chloropyrazine instead of 2-chloro-1,3-thiazole-5-carbonitrile in 10% yield. LCMS calculated for $C_{22}H_{24}ClN_8O$ (M+H)$^+$: m/z=451.2; found: 451.1. $^1$H NMR (300 MHz, DMSO-d$_6$): δ 8.28 (s, 1 H), 8.23 (s, 1 H), 8.05 (s, 1 H), 7.76 (s, 1 H), 7.24 (s, 1 H), 6.31 (m, 1 H), 4.89 (m, 1 H), 4.75 (m, 1 H), 4.05 (m, 3 H), 3.75 (m, 1 H), 2.58 (m, 6 H), 1.68 (m, 3 H).

Example 25

9-[1-(4-Amino-3-methyl-1H-pyrazolo[3,4-d]pyrimidin-1-yl)ethyl]-7-chloro-6-methyl-3,4-dihydro-1,4-benzoxazepin-5(2H)-one trifluoroacetate

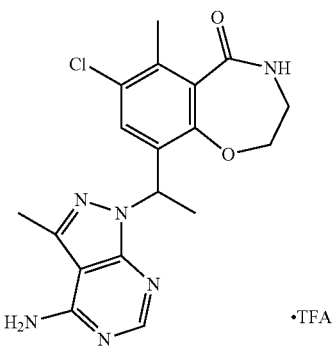 [SMILES: Cc1c(Cl)cc(C(C)n2nc(C)c3c(N)ncnc32)c2c1C(=O)NCCO2]

Step 1. 3-Acetyl-2-{2-[(tert-butoxycarbonyl)amino]ethoxy}-5-chloro-6-methylbenzoic acid

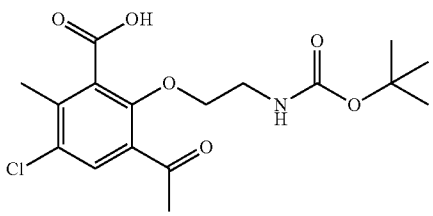 [SMILES: CC(=O)c1cc(Cl)c(C)c(C(=O)O)c1OCCNC(=O)OC(C)(C)C]

tert-Butyl [2-(6-acetyl-4-chloro-2-formyl-3-methylphenoxy)ethyl]carbamate (85 mg, 0.24 mmol) was stirred in methanol (7 mL) and 1.0 M sodium hydroxide in water (2.7 mL) and urea hydrogen peroxide addition compound (200 mg, 2 mmol) was added. Additional urea hydrogen peroxide addition compound (20 mg) and 1.0 M sodium hydroxide in water (0.5 mL) were added and the mixture was stirred for 3 more hours. 1 N HCl was added to pH 5 and the methanol was evaporated. The mixture was extracted with ethyl acetate, washed with brine, dried over sodium sulfate, filtered and evaporated to give the desired compound (75 mg, 84%). LCMS calculated for $C_{17}H_{22}ClNO_6Na$ $(M+Na)^+$: m/z=394.1; found: 393.9.

Step 2. 2-{2-[(tert-Butoxycarbonyl)amino]ethoxy}-5-chloro-3-(1-hydroxyethyl)-6-methylbenzoic acid

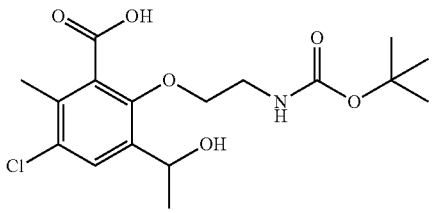 [SMILES: Cc1c(Cl)cc(C(C)O)c(OCCNC(=O)OC(C)(C)C)c1C(=O)O]

Sodium tetrahydroborate (6.1 mg, 0.16 mmol) was added to a mixture of 3-acetyl-2-{2-[(tert-butoxycarbonyl)amino]ethoxy}-5-chloro-6-methylbenzoic acid (40 mg, 0.1 mmol) in methanol (0.50 mL) at 0° C. and the reaction was stirred at room temperature for 1 hour. The solvent was removed and the residue was diluted with ethyl acetate, washed with saturated sodium bicarbonate, adjusted the pH to 5 with 1 N hydrogen chloride solution, washed with brine, dried over sodium sulfate, filtered and concentrated to give the desired compound (30 mg, 70%). LCMS calculated for $C_{17}H_{24}ClNO_6Na$ $(M+Na)^+$: m/z=396.1; found: 396.0.

Step 3. 7-Chloro-9-(1-hydroxyethyl)-6-methyl-3,4-dihydro-1,4-benzoxazepin-5(2H)-one

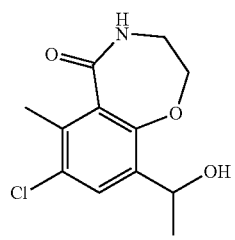 [SMILES: Cc1c(Cl)cc(C(C)O)c2c1C(=O)NCCO2]

2-{2-[(tert-Butoxycarbonyl)amino]ethoxy}-5-chloro-3-(1-hydroxyethyl)-6-methylbenzoic acid (27 mg, 0.072 mmol) was stirred in 4.0 M hydrogen chloride in 1,4-dioxane (3 mL) and evaporated. 1-Hydroxybenzotriazole hydrate (13 mg, 0.087 mmol), N,N-diisopropylethylamine (63 µL, 0.36 mmol) and N,N-dimethylformamide (2.0 mL) were added and the mixture was stirred for ten minutes. Benzotriazol-1-yloxytris(dimethylamino)-phosphonium hexafluorophosphate (38 mg, 0.087 mmol) was added and the mixture was stirred at 30° C. overnight. The mixture was diluted with ethyl acetate, washed with brine, dried over sodium sulfate, filtered and evaporated to give the desired product (14 mg, 76%). LCMS calculated for $C_{12}H_{15}ClNO_3$ $(M+H)^+$: m/z=256.1; found: 256.0.

Step 4. 7-Chloro-9-(1-chloroethyl)-6-methyl-3,4-dihydro-1,4-benzoxazepin-5(2H)-one

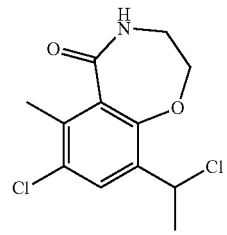 [SMILES: Cc1c(Cl)cc(C(C)Cl)c2c1C(=O)NCCO2]

A mixture of cyanuric chloride (15 mg, 0.079 mmol), 7-chloro-9-(1-hydroxyethyl)-6-methyl-3,4-dihydro-1,4-benzoxazepin-5(2H)-one (14 mg, 0.053 mmol) and N,N-dimethylformamide (20 µL) in methylene chloride (0.4 mL) was stirred at room temperature overnight. The mixture was diluted with methylene chloride, washed with saturated sodium bicarbonate, water, brine, dried over sodium sulfate, filtered and concentrated to give the desired compound (10 mg, 70%).

Step 5. 9-[1-(4-Amino-3-methyl-1H-pyrazolo[3,4-d]pyrimidin-1-yl)ethyl]-7-chloro-6-methyl-3,4-dihydro-1,4-benzoxazepin-5(2H)-one trifluoroacetate

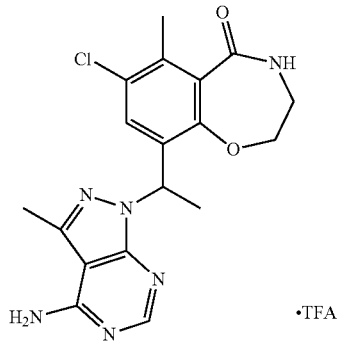

A mix of 7-chloro-9-(1-chloroethyl)-6-methyl-3,4-dihydro-1,4-benzoxazepin-5(2H)-one (10 mg, 0.04 mmol), 3-methyl-1H-pyrazolo[3,4-d]pyrimidin-4-amine (6.5 mg, 0.044 mmol), cesium carbonate (18 mg, 0.055 mmol) and potassium iodide (0.60 mg, 0.0036 mmol) in N,N-dimethylformamide (0.12 mL) was heated at 140° C. for 1 hour. The mix was diluted with ethyl acetate, washed with water, concentrated and purified by preparative LCMS (pH 2) to give the desired compound (2.7 mg, 10%). LCMS calculated for $C_{18}H_{20}ClN_6O_2(M+H)^+$: m/z=387.1; found: 387.0. $^1$H NMR (300 MHz, CD$_3$OD): δ 8.26 (s, 1 H), 7.61 (s, 1 H), 6.48 (m, 1 H), 4.25 (m, 4 H), 2.65 (s, 3 H), 2.37 (s, 3 H), 1.85 (m, 3 H).

Examples 26 and 27 tert-Butyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate

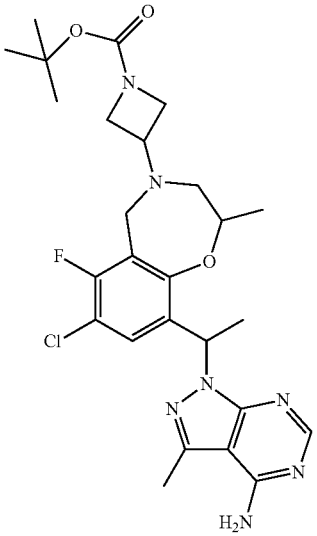 [SMILES: Cc1nn(C(C)c2cc(Cl)c(F)c3c2OC(C)CN(C2CN(C(=O)OC(C)(C)C)C2)C3)c2ncnc(N)c12]

Step 1.
1-(5-Chloro-4-fluoro-2-hydroxyphenyl)ethanone

To 4-chloro-3-fluorophenol (from Aldrich, 20 g, 100 mmol) was added acetyl chloride (14.1 mL, 199 mmol) under N$_2$ with stirring. The resulting mixture turned into a clear solution at room temperature quickly and it was heated at 60° C. for 2 hours. To the resultant mixture was added aluminum trichloride (25.0 g, 187 mmol) in portions and the reaction mixture was heated at 180° C. for 30 minutes. The solids slowly dissolved at high temperature. The reaction mixture was then cooled to room temperature while the flask was swirled carefully in order for the solid to form a thin layer inside the flask and then slowly quenched with 1.0 N HCl (300 mL) while cooling in an ice-bath and stirred overnight. The yellow precipitate was washed with water and dried under vacuum to give the desired product as a yellow solid (23.8 g), which was directly used in the next step without further purification.

Step 2. 1-(5-Chloro-4-fluoro-2-hydroxy-3-iodophenyl)ethanone

A solution of 1-(5-chloro-4-fluoro-2-hydroxyphenyl)ethanone (23.8 g, 126 mmol) in acetic acid (100 mL) was treated with N-iodosuccinimide (34.1 g, 151 mmol) and stirred at 70° C. for 2 hr. The reaction mixture was concentrated, diluted with EtOAc and quenched with sat. NaHCO$_3$ solution until the bubbling stopped. The organic layers were separated, washed with water, dried over MgSO$_4$ and stripped to give the desired product which was used in the next step without further purification.

Step 3. tert-Butyl 9-[1-(4-amino-3-methyl-1H-pyrazolo[3,4-d]pyrimidin-1-yl)ethyl]-7-chloro-6-fluoro-2-methyl-2,3-dihydro-1,4-benzoxazepine-4(5H)-carboxylate The title compound was prepared by methods analogous to Example 1, steps 1-8, but using 1-(5-chloro-4-fluoro-2-hydroxy-3-iodophenyl)ethanone and tert-butyl [(2R)-2-hydroxypropyl]carbamate (Alfa Aesar #H27296) in Step 1. Purification by preparative LCMS (pH 10) gave the desired compound (75 mg, 38%). LCMS calculated for $C_{23}H_{29}ClFN_6O_3$ (M+H)$^+$: m/z=491.2; found: 491.2.

Step 4. tert-Butyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate tert-Butyl 9-[1-(4-amino-3-methyl-1H-pyrazolo[3,4-d]pyrimidin-1-yl)ethyl]-7-chloro-6-fluoro-2-methyl-2,3-dihydro-1,4-benzoxazepine-4(5H)-carboxylate (75 mg, 0.15 mmol) was stirred in 4 N HCl in dioxane (5 mL) and evaporated. The residue was stirred in methanol (4 mL) and tert-butyl 3-oxoazetidine-1-carboxylate (110 mg, 0.61 mmol) was added. Sodium cyanoborohydride (86 mg, 1.4 mmol) was added and the mixture was warmed to 60° C. overnight and evaporated. Water was added and the mixture was extracted with ethyl acetate. The extracts were washed with brine, dried over sodium sulfate, filtered and concentrated. The reactions were purified by prep HPLC on C-18 column eluting water:acetonitrile gradient buffered pH 10 to give two diastereomers (peak #1 and 2): Peak #1 (Example 26): LCMS calculated for $C_{26}H_{34}ClFN_7O_3$ (M+H)$^+$: m/z=546.2; found: 546.2 $^1$H NMR (300 MHz, CD$_3$OD): δ 8.14 (s, 1 H), 7.38 (m, 1 H), 6.32 (m, 1 H), 4.11 (m, 1 H), 3.95 (m, 2 H), 3.78 (m, 2 H), 3.50 (m, 2 H), 2.92 (m, 2 H), 2.65 (m, 1 H), 2.60 (s, 3 H), 1.80 (m, 3 H), 1.42 (s, 9 H), 1.38 (m, 3 H). Peak #2 (Example 27): LCMS calculated for $C_{26}H_{34}ClFN_7O_3$ (M+H)$^+$: m/z=546.2; Found: 546.2.

Examples 28 and 29

1-{1-[4-(1-Acetylazetidin-3-yl)-7-chloro-6-fluoro-2-methyl-2,3,4,5-tetrahydro-1,4-benzoxazepin-9-yl]ethyl}-3-methyl-1H-pyrazolo[3,4-d]pyrimidin-4-amine

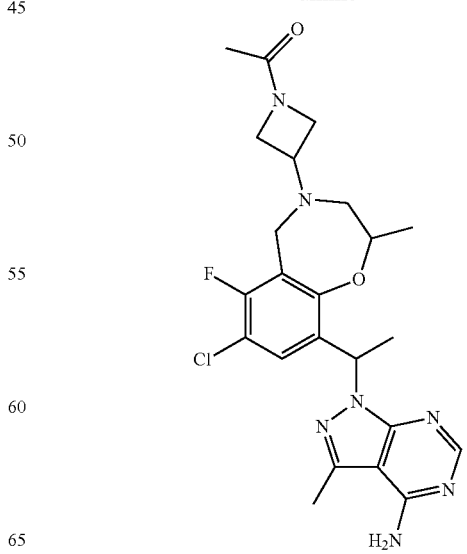

tert-Butyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate (6 mg, 0.01 mmol) (Example 26, step 4, peak 1) was stirred in 4 N HCl in dioxane for 30 minutes and evaporated to give the hydrochloride salt. The salt was stirred in N,N-dimethylformamide (0.2 mL) with N,N-diisopropylethylamine (6 µL, 0.03 mmol) and acetic anhydride (6 µL, 0.07 mmol) was added. The mixture was stirred for 5 minutes and diluted with methanol (5 mL). Purification by preparative LCMS (pH 10) gave the desired compound 3.3 mg (Example 28): LCMS calculated for $C_{23}H_{28}ClFN_7O_2$ (M+H)$^+$: m/z=488.2; found: 488.2 $^1$H NMR (300 MHz, CD$_3$OD): δ 8.14 (s, 1 H), 7.38 (m, 1 H), 6.32 (m, 1 H), 4.20 (m, 2 H), 4.00 (m, 2 H), 3.80 (m, 1 H), 3.50 (m, 2 H), 2.98 (m, 2 H), 2.67 (m, 1 H), 2.59 (s, 3 H), 1.85 (s, 3 H), 1.80 (m, 3 H), 1.39 (m, 3 H).

Utilizing the same procedure starting with the material of Example 27 (step 4, peak 2) produced 1.3 mg of product (Example 29): LCMS calculated for $C_{23}H_{28}ClFN_7O_2$ (M+H)$^+$: m/z=488.2; found: 488.2 $^1$H NMR (300 MHz, CD$_3$OD): δ 8.14 (s, 1 H), 7.38 (m, 1 H), 6.32 (m, 1 H), 4.20 (m, 1 H), 4.00 (m, 3 H), 3.79 (m, 1 H), 3.60 (m, 1 H), 3.48 (m, 1 H), 2.95 (m, 2 H), 2.71 (m, 1 H), 2.60 (s, 3 H), 1.85 (s, 3 H), 1.77 (m, 3 H), 1.31 (m, 3 H).

Examples 30, 31, 32, and 33

1-{1-[4-(1-Acetylazetidin-3-yl)-7-chloro-6-fluoro-2-methyl-2,3,4,5-tetrahydro-1,4-benzoxazepin-9-yl]ethyl}-3-methyl-1H-pyrazolo[3,4-d]pyrimidin-4-amine

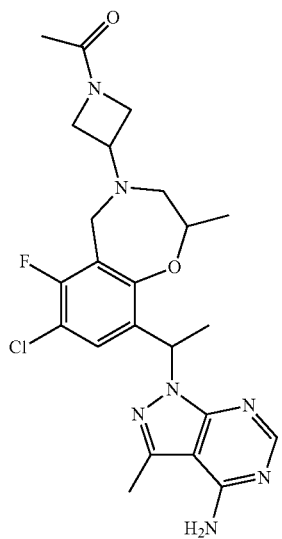 [SMILES: CC(=O)N1CC(N2Cc3c(F)c(Cl)cc(C(C)n4nc(C)c5c(N)ncnc54)c3OC(C)C2)C1]

The diasteromers from Example 28 were separated into the respective two enantiomers by chiral prep HPLC using a ChiralPAK IA column 5 µm, 20×250 mm eluting 30% ethanol in hexanes at 18 mL/min, with 20 mg/mL loading to give two peaks: Peak #1 (Example 30), retention time 7.76 min.: LCMS calculated for $C_{23}H_{28}ClFN_7O_2$ (M+H)$^+$: m/z=488.2; found: 488.2; Peak #2 (Example 31), retention time 10.23 min: LCMS calculated for $C_{23}H_{28}ClFN_7O_2$ (M+H)$^+$: m/z=488.2; found: 488.2

The diasteromers from Example 29 were separated into the respective two enantiomers by chiral prep HPLC using a ChiralPAK AD column 5 µm, 20×250 mm eluting 20% ethanol in hexanes at 16 mL/min, with 20 mg/mL loading to give two peaks: Peak #1 (Example 32), retention time 7.63 min.: LCMS calculated for $C_{23}H_{28}ClFN_7O_2$ (M+H)$^+$: m/z=488.2; found: 488.2; Peak #2 (Example 33), retention time 11.36 min.: LCMS calculated for $C_{23}H_{28}ClFN_7O_2$ (M+H)$^+$: m/z=488.2; found: 488.2.

Example 34

1-{1-[4-(1-Acetylazetidin-3-yl)-7-chloro-6-fluoro-2,3,4,5-tetrahydro-1,4-benzoxazepin-9-yl]ethyl}-3-methyl-1H-pyrazolo[3,4-d]pyrimidin-4-amine

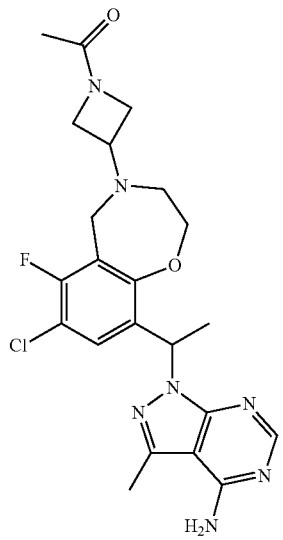 [SMILES: CC(=O)N1CC(N2CCOc3c(C(C)n4nc(C)c5c(N)ncnc54)cc(Cl)c(F)c3C2)C1]

Step 1. tert-Butyl 9-[1-(4-amino-3-methyl-1H-pyrazolo[3,4-d]pyrimidin-1-yl)ethyl]-7-chloro-6-fluoro-2,3-dihydro-1,4-benzoxazepine-4(5H)-carboxylate The title compound was prepared by methods analogous to Example 1, steps 1-8, but using 1-(5-chloro-4-fluoro-2-hydroxy-3-iodophenyl)ethanone (from Examples 26-27, step 2) in step 1.

Step 2. tert-Butyl 3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]azetidine-1-carboxylate The title compound was prepared by methods analogous to Example 26, step 2, but using tert-butyl 9-[1-(4-amino-3-methyl-1H-pyrazolo[3,4-d]pyrimidin-1-yl)ethyl]-7-chloro-6-fluoro-2,3-dihydro-1,4-benzoxazepine-4(5H)-carboxylate.

Step 3. 1-{1-[4-(1-acetylazetidin-3-yl)-7-chloro-6-fluoro-2,3,4,5-tetrahydro-1,4-benzoxazepin-9-yl]ethyl}-3-methyl-1H-pyrazolo[3,4-d]pyrimidin-4-amine tert-Butyl 3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]azetidine-1-carboxylate (14 mg, 0.026 mmol) was stirred in 4 N HCl in dioxane for 30 minutes and evaporated to give the hydrochloride salt. The salt was stirred in N,N-dimethylformamide (0.4 mL) with N,N-diisopropylethylamine (10 µL, 0.08 mmol) and acetic anhydride (10 µL, 0.2 mmol) was added. The mixture was stirred for 5 minutes and diluted with methanol. Purification by preparative LCMS (pH 10) gave the desired compound (Example 34). LCMS calculated for $C_{22}H_{26}ClN_7O_2$ $(M+H)^+$: m/z=474.2; found: 474.2.

Examples 35 and 36

1-{1-[(3S)-7-Chloro-6-fluoro-3-methyl-4-(methylsulfonyl)-2,3,4,5-tetrahydro-1,4-benzoxazepin-9-yl]ethyl}-3-methyl-1H-pyrazolo[3,4-d]pyrimidin-4-amine

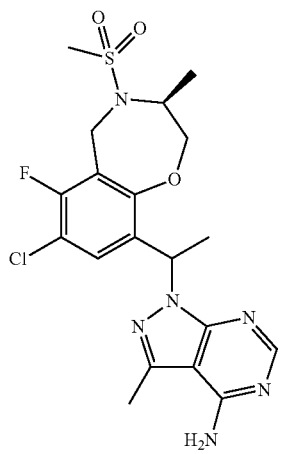 [SMILES: Cc1nn(C(C)c2cc(Cl)c(F)c3c2OC[C@H](C)N(S(C)(=O)=O)C3)c2ncnc(N)c12]

Step 1. tert-Butyl (3S)-9-[1-(4-amino-3-methyl-1H-pyrazolo[3,4-d]pyrimidin-1-yl)ethyl]-7-chloro-6-fluoro-3-methyl-2,3-dihydro-1,4-benzoxazepine-4(5H)-carboxylate The title compound was prepared by methods analogous to Example 1, steps 1-8, but using 1-(5-chloro-4-fluoro-2-hydroxy-3-iodophenyl)ethanone (from Examples 26-27, step 2) and tert-butyl [(1S)-2-hydroxy-1-methylethyl]carbamate [Ald. #469513] in Step 1. LCMS calculated for $C_{23}H_{29}ClFN_6O_3(M+H)^+$: m/z=491.2; found: 491.2.

Step 2. 1-{1-[(3S)-7-chloro-6-fluoro-3-methyl-4-(methylsulfonyl)-2,3,4,5-tetrahydro-1,4-benzoxazepin-9-yl]ethyl}-3-methyl-1H-pyrazolo[3,4-d]pyrimidin-4-amine tert-Butyl (3S)-9-[1-(4-amino-3-methyl-1H-pyrazolo[3,4-d]pyrimidin-1-yl)ethyl]-7-chloro-6-fluoro-3-methyl-2,3-dihydro-1,4-benzoxazepine-4(5H)-carboxylate (13 mg, 0.026 mmol) was stirred in methylene chloride (100 µL, 2 mmol) with N,N-diisopropylethylamine (14 µL, 0.079 mmol) and cooled to 0° C. Methanesulfonyl chloride (2.6 µL, 0.034 mmol) was added, and the mixture was stirred at 0° C. for 1 hr. The mixture was evaporated and diluted with methanol. The reactions were purified by prep HPLC on C-18 column eluting water:acetonitrile gradient buffered pH 10 to give two enantiomers: Peak #1 (Example 35): LCMS calculated for $C_{19}H_{23}ClFN_6O_3S$ $(M+H)^+$: m/z=469.1; found: 469.1; Peak #2 (Example 36): LCMS calculated for $C_{19}H_{23}ClFN_6O_3S$ $(M+H)^+$: m/z=469.1; found: 469.1.

Examples 37, 38, 39, and 40

1-{1-[7-Chloro-6-fluoro-2-methyl-4-(methylsulfonyl)-2,3,4,5-tetrahydro-1,4-benzoxazepin-9-yl]ethyl}-3-methyl-1H-pyrazolo[3,4-d]pyrimidin-4-amine

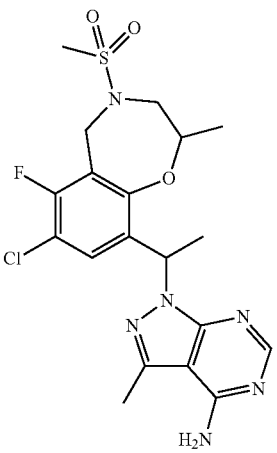 [SMILES: Cc1nn(C(C)c2cc(Cl)c(F)c3c2OC(C)CN(S(C)(=O)=O)C3)c2ncnc(N)c12]

The title compound was prepared by methods analogous to Example 36, but using tert-butyl 9-[1-(4-amino-3-methyl-1H-pyrazolo[3,4-d]pyrimidin-1-yl)ethyl]-7-chloro-6-fluoro-2-methyl-2,3-dihydro-1,4-benzoxazepine-4(5H)-carboxylate in step 2. The reactions were purified by prep HPLC on C-18 column eluting water:acetonitrile gradient buffered pH 10 to give two diastereomers: Peak #1, which was separated into the respective two enantiomers by chiral prep HPLC using a Phenomenex Lux Cellulose C-4 column 5 µm, 21.2×250 mm eluting 45% ethanol in hexanes at 18 mL/min, with 4 mg/mL loading to give two peaks: Peak #1A (Example 37), retention time 9.80 min: LCMS calculated for $C_{19}H_{23}ClFN_6O_3S$ $(M+H)^+$: m/z=469.1; found: 469.1; $^1H$ NMR (300 MHz, DMSO): δ 8.11 (s, 1 H), 7.35 (m, 1 H), 6.24 (m, 1 H), 4.75 (m, 1 H), 4.21 (m, 2 H), 3.78 (m, 1 H), 3.39 (m, 1 H), 2.87 (s, 3 H), 2.55 (s, 3 H), 1.68 (m, 3 H), 1.39 (m, 3 H); Peak #1B (Example 38), retention time 11.75 min: LCMS calculated for $C_{19}H_{23}ClFN_6O_3S$ $(M+H)^+$: m/z=469.1; found: 469.1.

The second diasteromer peak (Peak #2) was separated into the respective two enantiomers by chiral prep HPLC using a Phenomenex Lux Cellulose C-1 column 5 µm, 21.2×250 mm eluting 20% ethanol in hexanes at 18 mL/min, with 7 mg/mL loading to give two peaks: Peak #2A (Example 39), retention time 12.78 min: LCMS calculated for $C_{19}H_{23}ClFN_6O_3S$ $(M+H)^+$: m/z=469.1; found: 469.1; Peak #2B (Example 40), retention time 15.47 min: LCMS calculated for $C_{19}H_{23}ClFN_6O_3S$ $(M+H)^+$: m/z=469.1; found: 469.1.

Examples 41 and 42

3-[9-[1-(4-Amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]cyclobutanecarboxylic acid trifluoroacetate

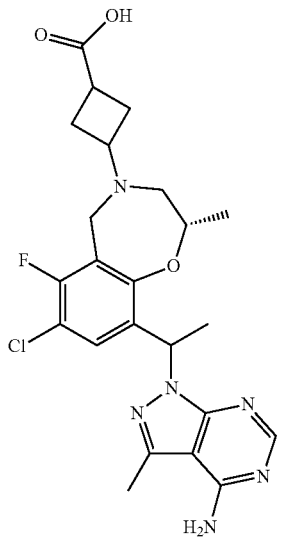 [SMILES: Cc1nn(C(C)c2cc(Cl)c(F)c3c2O[C@@H](C)CN(C2CC(C(=O)O)C2)C3)c2ncnc(N)c12]

The title compound was prepared by methods analogous to Example 26, but using 3-oxocyclobutanecarboxylic acid in step 2. The reactions were purified by prep HPLC on C-18 column eluting water:acetonitrile gradient buffered pH 2 to give two diastereomers: Peak #1 (Example 41): LCMS calculated for $C_{23}H_{27}ClFN_6O_3 (M+H)^+$: m/z=489.2; found: 489.2; Peak #2 (Example 42): LCMS calculated for $C_{23}H_{27}ClFN_6O_3 (M+H)^+$: m/z=489.2; found: 489.2. $^1$H NMR (300 MHz, DMSO-$d_6$): δ 8.11 (s, 1 H), 7.60 (m, 1 H), 6.28 (m, 1 H), 4.22 (m, 3 H), 4.00 (m, 2 H), 3.38 (m, 2 H), 2.80 (m, 2 H), 2.55 (s, 3 H), 2.22 (m, 2 H), 1.72 (m, 3 H), 1.40 (m, 3 H).

Examples 43 and 44

3-[(2S)-9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutanecarboxamide

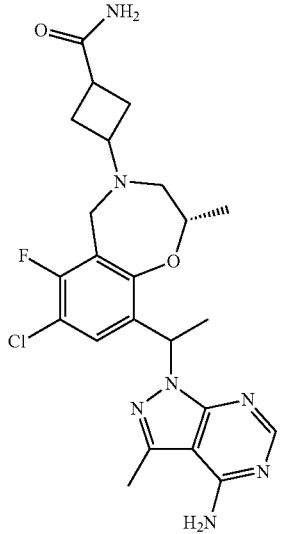 [SMILES: Cc1nn(C(C)c2cc(Cl)c(F)c3c2O[C@@H](C)CN(C2CC(C(N)=O)C2)C3)c2ncnc(N)c12]

N,N-Diisopropylethylamine (78 µl, 0.45 mmol) was added to a mixture of 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]cyclobutanecarboxylic acid trifluoroacetate (44 mg, 0.09 mmol) and N,N,N',N'-tetramethyl-O-(7-azabenzotriazol-1-yl)uronium hexafluorophosphate (34 mg, 0.09 mmol) in N,N-dimethylformamide (2 mL) at room temperature. A solution of ammonia in ethanol (2.0 M, 130 µl) was added and the reaction was stirred at room temperature for 1.5 hrs. The reactions were purified by prep HPLC on C-18 column eluting water:acetonitrile gradient buffered pH 10 to give two diastereomers: Peak #1 (Example 43): LCMS calculated for $C_{23}H_{28}ClFN_7O_2$ $(M+H)^+$: m/z=488.2; found: 488.2; Peak #2 (Example 44): LCMS calculated for $C_{23}H_{28}ClFN_7O_2$ $(M+H)^+$: m/z=488.2; found: 488.2.

Example 45

1-{1-[8-Chloro-7-fluoro-5-(methylsulfonyl)-3,4,5,6-tetrahydro-2H-1,5-benzoxazocin-10-yl]ethyl}-3-methyl-1H-pyrazolo[3,4-d]pyrimidin-4-amine

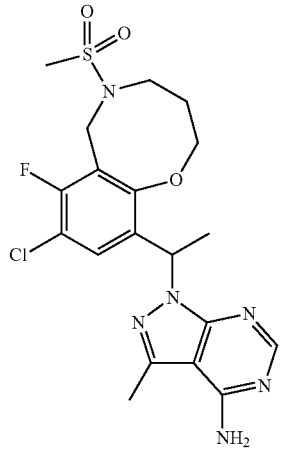 [SMILES: Cc1nn(C(C)c2cc(Cl)c(F)c3c2OCCCN(S(C)(=O)=O)C3)c2ncnc(N)c12]

Step 1. tert-butyl 10-[1-(4-amino-3-methyl-1H-pyrazolo[3,4-d]pyrimidin-1-yl)ethyl]-8-chloro-7-fluoro-3,4-dihydro-2H-1,5-benzoxazocine-5(6H)-carboxylate The title compound was prepared by methods analogous to Example 1, steps 1-8, but using 1-(5-chloro-4-fluoro-2-hydroxy-3-iodophenyl)ethanone (from Examples 26-27, step 2) and tert-butyl (3-hydroxypropyl)carbamate [Aldrich #416444] in Step 1. LCMS calculated for $C_{23}H_{29}ClFN_6O_3$ $(M+H)^+$: m/z=491.2; found: 491.2.

Step 2. 1-{1-[8-Chloro-7-fluoro-5-(methylsulfonyl)-3,4,5,6-tetrahydro-2H-1,5-benzoxazocin-10-yl]ethyl}-3-methyl-1H-pyrazolo[3,4-d]pyrimidin-4-amine tert-Butyl 10-[1-(4-amino-3-methyl-1H-pyrazolo[3,4-d]pyrimidin-1-yl)ethyl]-8-chloro-7-fluoro-3,4-dihydro-2H-1, 5-benzoxazocine-5(6H)-carboxylate (8 mg, 0.02 mmol) was stirred in methylene chloride (80 μL, 1 mmol) with N,N-diisopropylethylamine (8.5 μL, 0.049 mmol) and cooled to 0° C. Methanesulfonyl chloride (1.6 μL, 0.021 mmol) was added and the mixture was stirred at 0° C. for 1 hr. The mixture was evaporated and diluted with methanol and purified by preparative LCMS (pH 10) to give Example 45. LCMS calculated for $C_{19}H_{23}ClFN_6O_3S$ $(M+H)^+$: m/z=469.1; found: 469.1. $^1H$ NMR (300 MHz, $CD_3OD$): δ 8.14 (s, 1 H), 7.65 (m, 1 H), 6.36 (m, 1 H), 4.58 (m, 2 H), 4.21 (m, 2 H), 3.52 (m, 2 H), 2.87 (s, 3 H), 2.60 (s, 3 H), 1.91 (m, 2 H), 1.80 (m, 3 H).

Example 46

4-(1-Acetylazetidin-3-yl)-9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile

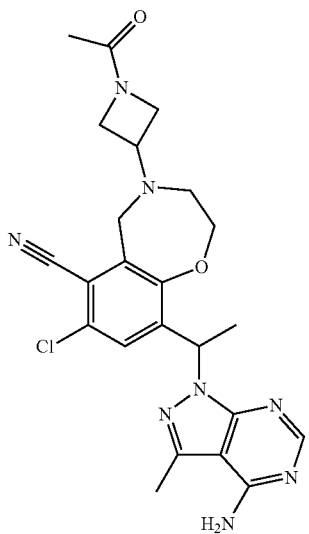 [SMILES: CC(=O)N1CC(N2CCOc3c(C(C)n4nc(C)c5c(N)ncnc54)cc(Cl)c(C#N)c3C2)C1]

Step 1.
1-(4-bromo-5-chloro-2-hydroxyphenyl)ethanone

The 2-bromo-1-chloro-4-methoxybenzene (25.0 g, 113 mmol) [Oakwood cat#035670] was dissolved in carbon disulfide (250 mL), and the acetyl chloride (12 mL, 170 mmol) and aluminum trichloride (37.6 g, 282 mmol) were added. The reaction was heated to reflux and monitored by LC/MS. After heating for 1 h, the reaction became two layers. The reaction allowed to cool to room temperature and poured over ice. The slurry was extracted with ethyl acetate 3×, the combined organic layer was washed with brine, dried over magnesium sulfate and concentrated to give 1-(4-bromo-5-chloro-2-hydroxyphenyl)ethanone as a solid (28.0 g, 99%). $^1H$ NMR (300 MHz, $CDCl_3$) δ 12.12 (s, 1H), 7.78 (s, 1H), 7.31 (s, 1H), 2.62 (s, 3H).

Step 2. 4-acetyl-2-chloro-5-hydroxybenzonitrile 1-(4-bromo-5-chloro-2-hydroxyphenyl)ethanone (6.2 g, 25 mmol) was combined with zinc cyanide (4.4 g, 37 mmol) in N,N-dimethylformamide (40 mL) degassed with nitrogen and tris(dibenzylideneacetone)dipalladium(0) (0.38 g, 0.42 mmol) and (9,9-dimethyl-9H-xanthene-4,5-diyl)bis(diphenylphosphine) (0.57 g, 0.99 mmol) were added. The reaction was degassed with nitrogen and heated to 120° C. and monitored by LC/MS. After heating for 2 hrs, the reaction was allowed to cool to room temperature, diluted with ethyl acetate, and filtered to remove the solids. The organic layer was washed with water, brine, dried over magnesium sulfate and concentrated in vacuo to give the crude product. The product was purified by FCC on silica gel eluting hexane:ethyl acetate gradient to give 4-acetyl-2-chloro-5-hydroxybenzonitrile as a yellow crystalline solid (3.5 g, 72%).

Step 3.
4-acetyl-6-chloro-3-hydroxy-2-iodobenzonitrile

The 4-acetyl-2-chloro-5-hydroxybenzonitrile (4.9 g, 25 mmol) was dissolved in acetic acid (61.2 mL), and the N-iodosuccinimide (6.8 g, 30 mmol) was added. The reaction was heated to 80° C. and, after heating for 18 hrs, the reaction was concentrated in vacuo to remove the acetic acid. The residue was taken up in ethyl acetate, washed with sodium bicarbonate water, brine, dried over magnesium sulfate and concentrated to give a dark oil. The crude product was purified by FCC on silica gel eluting hexane:ethyl acetate gradient to give 4-acetyl-6-chloro-3-hydroxy-2-iodobenzonitrile as a yellow solid (5.3 g, 66%).

Step 4. tert-butyl [2-(6-acetyl-4-chloro-3-cyano-2-iodophenoxy)ethyl]carbamate

Diethyl azodicarboxylate (2.3 mL, 14 mmol) was added slowly to a solution of triphenylphosphine (3.79 g, 14.5 mmol) and tert-butyl (2-hydroxyethyl)carbamate (2.3 g, 14 mmol) in tetrahydrofuran (93 mL) and cooled in an ice bath. After stirring for 15 minutes, the 4-acetyl-6-chloro-3-hydroxy-2-iodobenzonitrile (3.1 g, 9.6 mmol) was added. The reaction was allowed to warm to room temperature and stirred overnight. The reaction was diluted with ethyl acetate and washed with water, 1 N HCl, and brine, then dried over magnesium sulfate and concentrated to give a dark oil. The product was purified by FCC on silica gel eluting hexane:ethyl acetate gradient to give tert-butyl [2-(6-acetyl-4-chloro-3-cyano-2-iodophenoxy)ethyl]carbamate as a tan solid (3.2 g, 71%). LCMS calculated for $C_{16}H_{18}ClIN_2O_4Na$ $(M+Na)^+$: m/z=487.1; found: 486.9.

Step 5. tert-butyl [2-(6-acetyl-4-chloro-3-cyano-2-vinylphenoxy)ethyl]carbamate

A mixture of tert-butyl [2-(6-acetyl-4-chloro-3-cyano-2-iodophenoxy)ethyl]carbamate (3.3 g, 7.1 mmol), 4,4,5,5-tetramethyl-2-vinyl-1,3,2-dioxaborolane (1.81 mL, 10.6 mmol), [1,1'-bis(diphenylphosphino)ferrocene]dichloropalladium(II) complex with dichloromethane (1:1) (0.3 g, 0.4 mmol) and potassium carbonate (2.9 g, 21 mmol) in 1,4-dioxane (40 mL) and water (20 mL) was degassed with nitrogen. The resulting mixture was heated at 80° C. for 1 h. The mixture was poured into water and extracted with ethyl acetate. The extracts were washed with brine, dried over magnesium sulfate, filtered and concentrated. The product was purified by FCC on silica gel using ethyl acetate in hexane (0-40%) to give the desired compound tert-butyl [2-(6-acetyl-4-chloro-3-cyano-2-vinylphenoxy)ethyl]carbamate as a crystalline solid (2.2 g, 85%). LCMS calculated for $C_{18}H_{21}ClN_2O_4Na$ (M+Na)$^+$: m/z=387.1; found: 387.0.

Step 6. tert-butyl {2-[4-chloro-3-cyano-6-(1-hydroxyethyl)-2-vinylphenoxy]ethyl}carbamate Tert-butyl [2-(6-acetyl-4-chloro-3-cyano-2-vinylphenoxy)ethyl]carbamate (1.6 g, 4.4 mmol) was dissolved in methanol (40 mL) cooled in an ice bath and the sodium tetrahydroborate (0.16 g, 4.4 mmol) was added. The reaction was stirred for 1 h and water was added to quench residual hydride and the reaction was concentrated to remove the methanol. The aqueous was diluted with ethyl acetate washed with brine, dried over magnesium sulfate and concentrated to give tert-butyl {2-[4-chloro-3-cyano-6-(1-hydroxyethyl)-2-vinylphenoxy]ethyl}carbamate as a glass (1.6 g, 100%). LCMS calculated for $C_{18}H_{23}ClN_2O_4Na$ (M+Na)$^+$: m/z=389.1; found: 389.1.

Step 7. tert-butyl {2-[4-chloro-3-cyano-2-formyl-6-(1-hydroxyethyl)phenoxy]ethyl}carbamate Tert-butyl {2-[4-chloro-3-cyano-6-(1-hydroxyethyl)-2-vinylphenoxy]ethyl}carbamate (1.6 g, 4.4 mmol) was dissolved in methylene chloride (1.2 mL) cooled in a dry ice acetone bath and ozone/oxygen was bubbled through the solution until a persistent blue color remained. The reaction was purged with oxygen and nitrogen to remove excess ozone and dimethyl sulfide (0.80 mL, 11 mmol) was added to reduce the ozonide. After stirring for 1 h, the reaction was complete. This was concentrated in vacuo to give a residue give tert-butyl {2-[4-chloro-3-cyano-2-formyl-6-(1-hydroxyethyl)phenoxy]ethyl}carbamate. LCMS calculated for $C_{17}H_{21}ClN_2O_5Na$ (M+Na)$^+$: m/z=391.1; found: 391.1.

Step 8. 7-chloro-9-(1-hydroxyethyl)-2,3-dihydro-1,4-benzoxazepine-6-carbonitrile The crude tert-butyl {2-[4-chloro-3-cyano-2-formyl-6-(1-hydroxyethyl)phenoxy]ethyl}carbamate was dissolved in 1,4-dioxane (16 mL) and was added to an ice cooled 4.0 M hydrogen chloride in dioxane (40 mL) solution. After stirring for 1 h, the reaction was concentrated in vacuo to give 7-chloro-9-(1-hydroxyethyl)-2,3-dihydro-1,4-benzoxazepine-6-carbonitrile as an oil. LCMS calculated for $C_{12}H_{12}ClN_2O_2$(M+H)$^+$: m/z=251.1; found: 251.0. $^1$H NMR (300 MHz, DMSO-d$_6$) δ 8.55 (t, J=2.0 Hz, 1H), 7.75 (s, 1H), 5.53 (d, J=4.6 Hz, 1H), 5.05-4.82 (m, 1H), 4.53-4.24 (m, 2H), 4.20-4.04 (m, 2H), 1.26 (d, J=6.4 Hz, 3H).

Step 9. 7-chloro-9-(1-hydroxyethyl)-2,3,4,5-tetrahydro-1,4-benzoxazepine-6-carbonitrile The crude 7-chloro-9-(1-hydroxyethyl)-2,3-dihydro-1,4-benzoxazepine-6-carbonitrile was taken up in ethanol (30 mL) cooled in an ice bath and the sodium tetrahydroborate (0.16 g, 4.4 mmol) was added. The reaction was allowed to stir for 1 h, and water was added to quench the remaining hydride and the reaction was concentrated to remove most of the ethanol. The residue was dissolved with ethyl acetate, washed with brine, dried over magnesium sulfate, and concentrated to give 7-chloro-9-(1-hydroxyethyl)-2,3,4,5-tetrahydro-1,4-benzoxazepine-6-carbonitrile as an oil (0.45 g, 41%). LCMS calculated for $C_{12}H_{14}ClN_2O_2$(M+H)$^+$: m/z=253.1; found: 253.0.

Step 10. tert-butyl 7-chloro-6-cyano-9-(1-hydroxyethyl)-2,3-dihydro-1,4-benzoxazepine-4(5H)-carboxylate 7-Chloro-9-(1-hydroxyethyl)-2,3,4,5-tetrahydro-1,4-benzoxazepine-6-carbonitrile (0.140 g, 0.554 mmol) was dissolved in methylene chloride (5.0 mL, 78 mmol) and N,N-diisopropylethylamine (0.29 mL, 1.7 mmol) at room temperature, and the di-tert-butyldicarbonate (0.24 g, 1.1 mmol) was added. The reaction was stirred at room temperature for 1 hr and then diluted with ethyl acetate and washed with 1 N HCl, brine, dried over magnesium sulfate, and concentrated to give a yellow oil. The product was purified by FCC on silica gel eluting a hexane:ethyl acetate gradient to give tert-butyl 7-chloro-6-cyano-9-(1-hydroxyethyl)-2,3-dihydro-1,4-benzoxazepine-4(5H)-carboxylate as an oil (0.12 g, 61%). LCMS calculated for $C_{17}H_{21}ClN_2O_4Na$ (M+Na)$^+$: m/z=375.1; found: 375.0.

Step 11. tert-butyl 7-chloro-9-(1-chloroethyl)-6-cyano-2,3-dihydro-1,4-benzoxazepine-4(5H)-carboxylate The tert-butyl 7-chloro-6-cyano-9-(1-hydroxyethyl)-2,3-dihydro-1,4-benzoxazepine-4(5H)-carboxylate (0.090 g, 0.26 mmol) was dissolved in methylene chloride (3 mL) and N,N-dimethylformamide (0.020 mL) and cooled in an ice bath. The thionyl chloride (0.037 mL, 0.51 mmol) was added slowly, and the reaction was stirred for 1 h and then diluted with methylene chloride (30 mL). The reaction mixture was cooled in an ice bath, and water saturated sodium bicarbonate was added. The organic layer was washed with water, brine, dried over magnesium sulfate, and concentrated to give tert-butyl 7-chloro-9-(1-chloroethyl)-6-cyano-2,3-dihydro-1,4-benzoxazepine-4(5H)-carboxylate as an oil. LCMS calculated for $C_{17}H_{20}Cl_2N_2O_3Na$ (M+Na)$^+$: m/z=393.1; found: 393.0.

Step 12. tert-butyl 9-[1-(4-amino-3-methyl-1H-pyrazolo[3,4-d]pyrimidin-1-yl)ethyl]-7-chloro-6-cyano-2,3-dihydro-1,4-benzoxazepine-4(5H)-carboxylate The crude tert-butyl 7-chloro-9-(1-chloroethyl)-6-cyano-2,3-dihydro-1,4-benzoxazepine-4(5H)-carboxylate (0.090 g, 0.26 mmol) was dissolved in N,N-dimethylformamide (3 mL), and 3-methyl-1H-pyrazolo[3,4-d]pyrimidin-4-amine (0.076 g, 0.51 mmol) and cesium carbonate (0.17 g, 0.51 mmol) were added. The reaction was heated to 90° C. for 18 hrs and then allowed to cool to room temperature. The reaction was diluted with ethyl acetate and then decanted from the solids. The organic layer was washed with water, brine, dried over magnesium sulfate, and concentrated to give tert-butyl 9-[1-(4-amino-3-methyl-1H-pyrazolo[3,4-d]pyrimidin-1-yl)ethyl]-7-chloro-6-cyano-2,3-dihydro-1,4-benzoxazepine-4(5H)-carboxylate as an oil. LCMS calculated for $C_{23}H_{27}ClN_7O_3$ (M+H)$^+$: m/z=484.1; found: 484.1.

Step 13. 9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile bishydrochloride The crude tert-butyl 9-[1-(4-amino-3-methyl-1H-pyrazolo[3,4-d]pyrimidin-1-yl)ethyl]-7-chloro-6-cyano-2,3-dihydro-1,4-benzoxazepine-4(5H)-carboxylate was dissolved in 4.0 M hydrogen chloride in dioxane (4.0 mL) at room temperature and was stirred for 1 h. The reaction was concentrated in vacuo to give 9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile bishydrochloride as an off white solid (0.065 g, 66%). LCMS calculated for $C_{18}H_{19}ClN_7O$ (M+H)$^+$: m/z=384.1; found: 384.2.

Step 14. tert-butyl 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]azetidine-1-carboxylate 9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile bishydrochloride (0.030 g, 0.078 mmol) was dissolved in methanol (3.0 mL), and the tert-butyl 3-oxoazetidine-1-carboxylate (0.027 g, 0.16 mmol) and then sodium cyanoborohydride (0.0098 g, 0.16 mmol) were added. The reaction was heated to 60° C. for 3 hrs and then allowed to cool to room temperature. The reaction was diluted with ethyl acetate and washed with brine. The organic layer dried over magnesium sulfate and concentrated to give the crude product as an amber oil. The oil was purified by prep HPLC on a C-18 column eluting water:acetonitrile gradient at pH 10 to give tert-butyl 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]azetidine-1-carboxylate (0.015 g, 35%). LCMS calculated for $C_{26}H_{32}ClN_8O_3$ (M+H)$^+$: m/z=539.2; found: 539.2.

Step 15. 9-[1-(4-amino-3-methyl-1H-pyrazolo[3,4-d]pyrimidin-1-yl)ethyl]-4-azetidin-3-yl-7-chloro-2,3,4,5-tetrahydro-1,4-benzoxazepine-6-carbonitrile trishydrochloride Tert-butyl 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]azetidine-1-carboxylate (0.015 g, 0.0278 mmol) was dissolved in 4.0 M hydrogen chloride in dioxane (3.0 mL, 12 mmol) at room temperature and stirred for 1 hr and then concentrated in vacuo to give 9-[1-(4-amino-3-methyl-1H-pyrazolo[3,4-d]pyrimidin-1-yl)ethyl]-4-azetidin-3-yl-7-chloro-2,3,4,5-tetrahydro-1,4-benzoxazepine-6-carbonitrile trishydrochloride as a semi-solid. LCMS calculated for $C_{21}H_{24}ClN_8O$ (M+H)$^+$: m/z=439.1; found: 439.1.

Step 16. 4-(1-acetylazetidin-3-yl)-9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile The crude 9-[1-(4-amino-3-methyl-1H-pyrazolo[3,4-d]pyrimidin-1-yl)ethyl]-4-azetidin-3-yl-7-chloro-2,3,4,5-tetrahydro-1,4-benzoxazepine-6-carbonitrile trishydrochloride (0.015 g, 0.0278 mmol) was dissolved in N,N-dimethylformamide (2 mL) and cooled in an ice bath, and then N,N-diisopropylethylamine (0.0142 g, 0.112 mmol) and acetic anhydride (0.0032 mL, 0.033 mmol) were added. After stirring for 1 h, the product was purified without work up, by prep HPLC on a C-18 column eluting water:acetonitrile gradient buffered pH 10 to give 4-(1-acetylazetidin-3-yl)-9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile as a white amorphous solid (0.004 g, 33%). LCMS calculated for $C_{23}H_{26}ClN_8O_2$ (M+H)$^+$: m/z=481.2; found: 481.2.

Example 47

9-[1-(4-amino-3-methyl-1H-pyrazolo[3,4-d]pyrimidin-1-yl)ethyl]-7-chloro-4-[1-(2-hydroxyethyl)azetidin-3-yl]-2,3,4,5-tetrahydro-1,4-benzoxazepine-6-carbonitrile

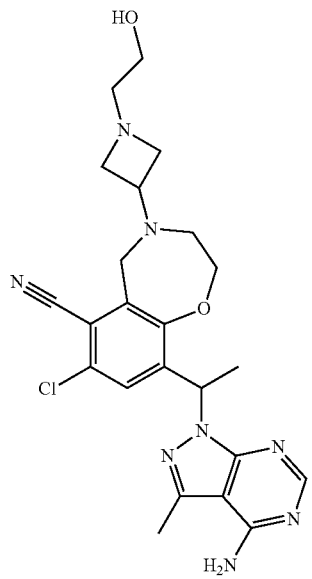 [SMILES: Cc1nn(C(C)c2cc(Cl)c(C#N)c3c2OCCN(C2CN(CCO)C2)C3)c2ncnc(N)c12]

9-[1-(4-Amino-3-methyl-1H-pyrazolo[3,4-d]pyrimidin-1-yl)ethyl]-4-azetidin-3-yl-7-chloro-2,3,4,5-tetrahydro-1,4-benzoxazepine-6-carbonitrile (0.015 g, 0.034 mmol) (from Example 46, Step 15) and 2-bromoethanol (0.0097 mL, 0.14 mmol) were combined in N,N-dimethylformamide (1 mL) with triethylamine (0.019 mL, 0.14 mmol) at room temperature. The reaction was heated to 85° C. and after heating for 2 hrs the reaction was concentrated in vacuo and the residue was purified by prep HPLC on a C-18 column eluting water:acetonitrile gradient buffered pH 10 to give the desired compound as a white amorphous solid (0.008 g, 50%). LCMS calculated for $C_{23}H_{28}ClN_8O_2$ (M+H)$^+$: m/z=483.2; found: 483.2.

Examples 48 and 49

4-(1-Acetylazetidin-3-yl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile

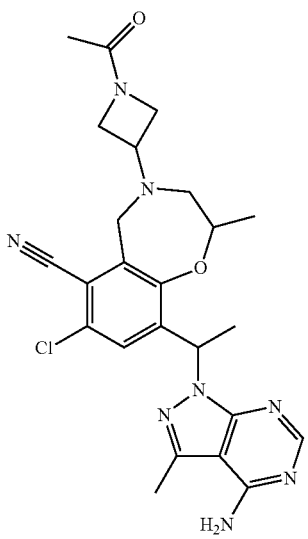 [SMILES: CC(=O)N1CC(N2Cc3c(C#N)c(Cl)cc(C(C)n4nc(C)c5c(N)ncnc54)c3OC(C)C2)C1]

Step 1. tert-butyl [2-(6-acetyl-4-chloro-3-cyano-2-iodophenoxy)propyl]carbamate

Using methods analogous to Example 46, but using tert-butyl (2-hydroxypropyl)carbamate in step 4, tert-butyl [2-(6-acetyl-4-chloro-3-cyano-2-iodophenoxy)propyl]carbamate was prepared as a pale yellow oil (1.3 g, 58%). LCMS calculated for $C_{17}H_{20}ClN_2O_4Na$ (M+Na)$^+$: m/z=501.0; found: 501.0.

Step 2. 4-(1-acetylazetidin-3-yl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile Using methods analogous to Example 46, but using the intermediate tert-butyl [2-(6-acetyl-4-chloro-3-cyano-2-iodophenoxy)propyl]carbamate, the desired compound was prepared as a mixture of diastereomers. The isomers were separated and purified by prep HPLC on a C-18 column eluting water:acetonitrile gradient buffered pH 10, to obtain: Peak #1 (Example 48): LCMS calculated for $C_{24}H_{28}ClN_8O_2$ (M+H)$^+$: m/z=495.1; found: 495.2. and Peak #2 (Example 49): LCMS calculated for $C_{24}H_{28}ClN_8O_2$ (M+H)$^+$: m/z=495.1; found: 495.2.

Examples 50 and 51

2-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidin-1-yl}acetamide

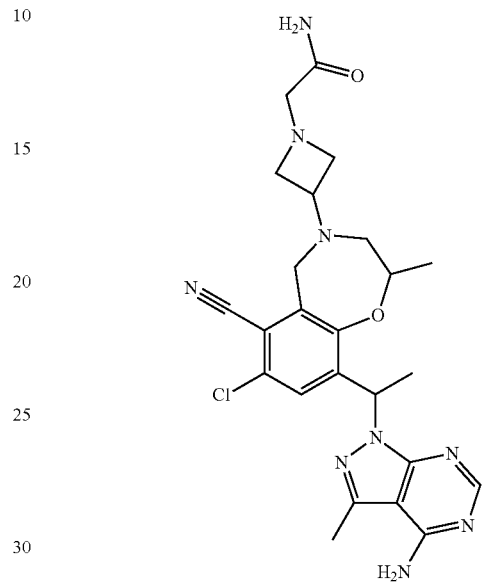

Step 1. 9-[1-(4-amino-3-methyl-1H-pyrazolo[3,4-d]pyrimidin-1-yl)ethyl]-4-azetidin-3-yl-7-chloro-2-methyl-2,3,4,5-tetrahydro-1,4-benzoxazepine-6-carbonitrile trishydrochloride Using methods analogous to Example 46, steps 1-15, but using tert-butyl (2-hydroxypropyl)carbamate in step 4, the 9-[1-(4-amino-3-methyl-1H-pyrazolo[3,4-d]pyrimidin-1-yl)ethyl]-4-azetidin-3-yl-7-chloro-2-methyl-2,3,4,5-tetrahydro-1,4-benzoxazepine-6-carbonitrile trishydrochloride was prepared as a solid. LCMS calculated for $C_{22}H_{26}ClN_8O$ (M+H)$^+$: m/z=453.2; found: 453.2.

Step 2. 2-{3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidin-1-yl}acetamide 2-Bromoacetamide (0.01 g, 0.09 mmol) was added to a mixture of 9-[1-(4-amino-3-methyl-1H-pyrazolo[3,4-d]pyrimidin-1-yl)ethyl]-4-azetidin-3-yl-7-chloro-2-methyl-2,3,4,5-tetrahydro-1,4-benzoxazepine-6-carbonitrile trishydrochloride (20 mg, 0.04 mmol) and triethylamine (20 μL, 0.18 mmol) in N,N-dimethylformamide (2 mL) and then heated to 80° C. for 2 h. The reaction was allowed to cool and was purified without work up by prep HPLC on a C-18 column eluting water:acetonitrile gradient buffered pH 10 to give the title compounds as two separated diastereomers: Peak #1 (Example 50): LCMS calculated for $C_{24}H_{29}ClN_9O_2$ (M+H)$^+$: m/z=510.2; found: 510.2; Peak #2 (Example 51): LCMS calculated for $C_{24}H_{29}ClN_9O_2$ (M+H)$^+$: m/z=510.2; found: 510.2.

Examples 52 and 53

2-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidin-1-yl}acetamide

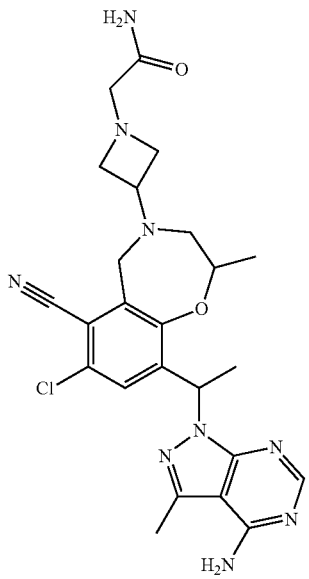 [SMILES: Cc1nn(C(C)c2cc(Cl)c(C#N)c3c2OC(C)CN(C2CN(CC(N)=O)C2)C3)c2ncnc(N)c12]

Peak #2 (from Example 51) was separated into the respective enantiomers by chiral prep HPLC using a Phenomenex Lux Cellulose C-4 column 5 μm, 21.2×250 mm eluting with 60% ethanol in hexanes at 18 mL/min, with 5 mg/mL loading to give two peaks: Peak #1 (Example 52), retention time 9.48 min: LCMS calculated for $C_{24}H_{29}ClN_9O_2$ (M+H)$^+$: m/z=510.2; found: 510.2; Peak #2 (Example 53), retention time 12.42 min: LCMS calculated for $C_{24}H_{29}ClN_9O_2$ (M+H)$^+$: m/z=510.2; found: 510.2.

Examples 54 and 55

9-[1-(4-Amino-3-methyl-1H-pyrazolo[3,4-d]pyrimidin-1-yl)ethyl]-7-chloro-4-[1-(2-hydroxy-2-methylpropyl)azetidin-3-yl]-2-methyl-2,3,4,5-tetrahydro-1,4-benzoxazepine-6-carbonitrile

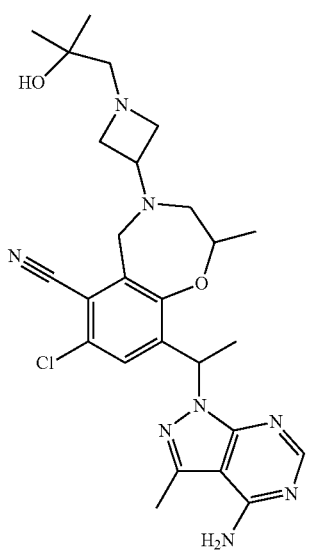 [SMILES: Cc1nn(C(C)c2cc(Cl)c(C#N)c3c2OC(C)CN(C2CN(CC(C)(C)O)C2)C3)c2ncnc(N)c12]

9-[1-(4-Amino-3-methyl-1H-pyrazolo[3,4-d]pyrimidin-1-yl)ethyl]-4-azetidin-3-yl-7-chloro-2-methyl-2,3,4,5-tetrahydro-1,4-benzoxazepine-6-carbonitrile trishydrochloride (0.015 g, 0.034 mmol) was dissolved in N,N-dimethylformamide (1.0 mL) and triethylamine (0.025 mL, 0.18 mmol), and 2,2-dimethyloxirane (0.050 g) was added. The reaction was heated to 85° C. stirred for 4 h. The reaction was concentrated in vacuo, and the product was purified without workup by prep HPLC on a C-18 column eluting water:acetonitrile gradient buffered pH 10 to give the title compound as two diastereomers: Peak #1 (Example 54) (0.002 g, 13%): LCMS calculated for $C_{26}H_{34}ClN_8O_2$ (M+H)$^+$: m/z=525.2; found: 525.2; Peak #2 (Example 55) (0.002 g 13%): LCMS calculated for $C_{26}H_{34}ClN_8O_2$ (M+H)$^+$: m/z=525.2; found: 525.2.

Examples 56 and 57

(2S)-9-[1-(4-Amino-3-methyl-1H-pyrazolo[3,4-d]pyrimidin-1-yl)ethyl]-7-chloro-4-[1-(2-hydroxyethyl)azetidin-3-yl]-2-methyl-2,3,4,5-tetrahydro-1,4-benzoxazepine-6-carbonitrile

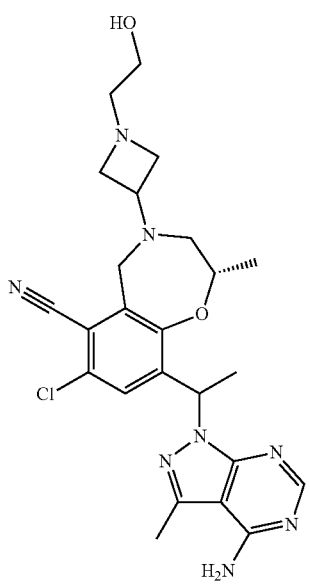 [SMILES: Cc1nn(C(C)c2cc(Cl)c(C#N)c3c2O[C@@H](C)CN(C2CN(CCO)C2)C3)c2ncnc(N)c12]

Using methods analogous to Example 47, but using tert-butyl [(2R)-2-hydroxypropyl]carbamate (from Example 46, step 4), the desired products were prepared as a mixture of single diastereomers. The reaction products were purified by prep HPLC on a C-18 column eluting water:acetonitrile gradient buffered pH 10 to give two diastereomers: Peak #1 (Example 56), as a white amorphous solid: LCMS calculated for $C_{24}H_{30}ClN_8O_2$ (M+H)$^+$: m/z=497.2; Found: 497.2; Peak #2 (Example 57), as a white amorphous solid: LCMS calculated for $C_{24}H_{30}ClN_8O_2$ (M+H)$^+$: m/z=497.2; found: 497.2.

Example 58

9-[1-(4-Amino-3-methyl-1H-pyrazolo[3,4-d]pyrimidin-1-yl)ethyl]-7-chloro-4-(2-hydroxyethyl)-2,3,4,5-tetrahydro-1,4-benzoxazepine-6-carbonitrile

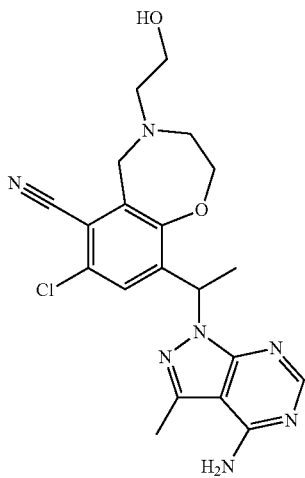 [SMILES: Cc1nn(C(C)c2cc(Cl)c(C#N)c3c2OCCN(CCO)C3)c2ncnc(N)c12]

2-Bromoethanol (4.7 μL, 0.066 mmol) was added to a mixture of 9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile bishydrochloride (15 mg, 0.039 mmol) (from Example 46, step 13) and triethylamine (10 μL, 0.09 mmol) in N,N-dimethylformamide (2 mL). The reaction was heated at 80° C. for 3 h and then allowed to cool. The product was purified without workup by prep HPLC on a C-18 column eluting water:acetonitrile gradient buffered pH 10 to give the desired compound as white amorphous solid (0.08 g, 50%). LCMS calculated for $C_{20}H_{23}ClN_7O_2$ (M+H)+: m/z=428.1; found: 428.2.

Examples 59 and 60

9-[1-(4-Amino-3-methyl-1H-pyrazolo[3,4-d]pyrimidin-1-yl)ethyl]-7-chloro-2-methyl-4-(pyridin-3-ylmethyl)-2,3,4,5-tetrahydro-1,4-benzoxazepine-6-carbonitrile

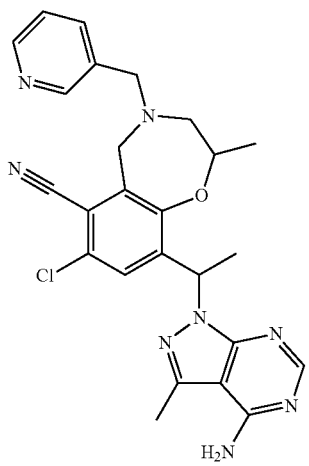 [SMILES: Cc1nn(C(C)c2cc(Cl)c(C#N)c3c2OC(C)CN(Cc2cccnc2)C3)c2ncnc(N)c12]

Step 1. 9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile bishydrochloride Using methods analogous to Example 46, steps 1-13, but using tert-butyl (2-hydroxypropyl)carbamate in step 4, the 9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile bishydrochloride was prepared as a mixture of diastereomers. LCMS calculated for $C_{19}H_{21}ClN_7O$ (M+H)+: m/z=398.1; found: 398.2.

Step 2. 9-[1-(4-amino-3-methyl-1H-pyrazolo[3,4-d]pyrimidin-1-yl)ethyl]-7-chloro-2-methyl-4-(pyridin-3-ylmethyl)-2,3,4,5-tetrahydro-1,4-benzoxazepine-6-carbonitrile 9-[1-(4-Amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile bishydrochloride (0.020 g, 0.05 mmol) was taken up in N,N-dimethylformamide (2.0 mL) and triethylamine (0.034 mL, 0.24 mmol), and the 3-(bromomethyl)pyridine hydrobromide was added. The reaction was heated to 85° C. for 2 h and was allowed to cool. The product was purified by prep HPLC on C-18 column eluting water:acetonitrile gradient buffered pH 10 to give two diastereomers: Peak #1 (Example 59): LCMS calculated for $C_{25}H_{26}ClN_8O$ (M+H)+: m/z=489.2; found: 489.2; Peak #2 (Example 60): LCMS calculated for $C_{25}H_{26}ClN_8O$ (M+H)+: m/z=489.2; found: 489.2.

Examples 61, 62, 63, and 64

9-[1-(4-Amino-3-methyl-1H-pyrazolo[3,4-d]pyrimidin-1-yl)ethyl]-7-chloro-4-(2-hydroxyethyl)-2-methyl-2,3,4,5-tetrahydro-1,4-benzoxazepine-6-carbonitrile

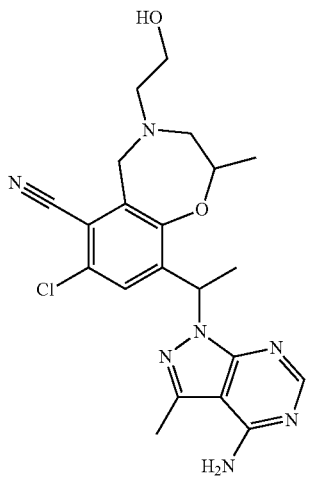 [SMILES: Cc1nn(C(C)c2cc(Cl)c(C#N)c3c2OC(C)CN(CCO)C3)c2ncnc(N)c12]

Using methods analogous to Example 59, but using 2-bromoethanol in step 2, a mixture of diastereomers of the desired compound was prepared. The isomers were separated into the respective four enantiomers by chiral prep HPLC using a Phenomenex Lux Cellulose C-4 column 5 µm, 21.2×250 mm eluting 20% ethanol in hexanes at 22 mL/min, with 7 mg/mL loading to give four peaks retention time: Peak #1 (Example 61), retention time 15.47 min: LCMS calculated for $C_{21}H_{25}ClN_7O_2$ (M+H)$^+$: m/z=442.2; found: 442.1; Peak #2 (Example 62), retention time 18.18 min: LCMS calculated for $C_{21}H_{25}ClN_7O_2$ (M+H)$^+$: m/z=442.2; found: 442.1; Peak #3 (Example 63), retention time 26.86 min: LCMS calculated for $C_{21}H_{25}ClN_7O_2$ (M+H)$^+$: m/z=442.2; found: 442.1; Peak #4 (Example 64), retention time 29.28 min: LCMS calculated for $C_{21}H_{25}ClN_7O_2$ (M+H)$^+$: m/z=442.2; found: 442.1.

Examples 65 and 66

9-[1-(4-Amino-3-methyl-1H-pyrazolo[3,4-d]pyrimidin-1-yl)ethyl]-7-chloro-4-(2-hydroxy-2-methylpropyl)-2-methyl-2,3,4,5-tetrahydro-1,4-benzoxazepine-6-carbonitrile

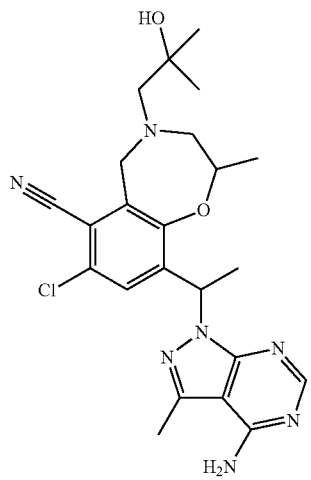 [SMILES: Cc1nn(C(C)c2cc(Cl)c(C#N)c3c2OC(C)CN(CC(C)(C)O)C3)c2ncnc(N)c12]

Oxirane, 2,2-dimethyl-(5.5 µL, 0.066 mmol) was added to a mixture of 9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile bishydrochloride (16 mg, 0.039 mmol) and triethylamine (10 µL, 0.09 mmol) in N,N-dimethylformamide (2 mL). The reaction was heated at 80° C. for 3 hrs and was allowed to cool to room temperature. The reaction was purified without workup by prep HPLC on C-18 column eluting water:acetonitrile gradient buffered pH 10 to give two diastereomers: Peak #1 (Example 65): LCMS calculated for $C_{23}H_{29}ClN_7O_2$ (M+H)$^+$: m/z=470.2; found: 470.2; Peak #2 (Example 66): LCMS calculated for $C_{23}H_{29}ClN_7O_2$ (M+H)$^+$: m/z=470.2; found: 470.2.

Examples 67 and 68

N-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}acetamide

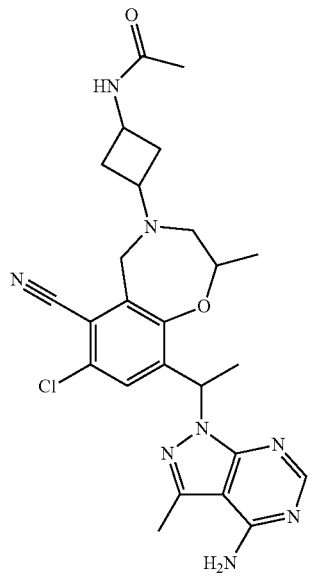 [SMILES: CC(=O)NC1CC(N2Cc3c(C#N)c(Cl)cc(C(C)n4nc(C)c5c(N)ncnc54)c3OC(C)C2)C1]

Step 1: tert-Butyl {3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}carbamate 9-[1-(4-Amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile bishydrochloride (20 mg, 0.05 mmol) from Example 59, step 1, was dissolved in methanol (1.1 mL), and the tert-butyl (3-oxocyclobutyl)carbamate (0.019 g, 0.10 mmol) was added, followed by the sodium cyanoborohydride (0.0063 g, 0.10 mmol). The reaction was heated to 60° C. for 2 h, allowed to cool, diluted with water, and extracted with ethyl acetate. The combined organic layer was washed with brine, dried over magnesium sulfate, filtered, and concentrated to give tert-butyl {3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}carbamate. LCMS calculated for $C_{28}H_{36}ClN_8O_3$ (M+H)$^+$: m/z=567.2; found: 567.3.

Step 2. 4-(3-Aminocyclobutyl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile tris hydrochloride Tert-butyl {3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}carbamate was taken up in 4.0 M hydrogen chloride in dioxane (1 mL, 4 mmol) and was stirred for 1 h. The reaction was concentrated in vacuo to give crude 4-(3-aminocyclobutyl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6- carbonitrile trishydrochloride as a solid. LCMS calculated for $C_{23}H_{28}ClN_8O$ (M+H)$^+$: m/z=467.2; found: 467.2.

Step 3. N-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}acetamide The crude 4-(3-aminocyclobutyl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile trishydrochloride was dissolved in N,N-dimethylformamide (2 mL) and triethylamine (10 µL, 0.1 mmol). To this mixture was added acetic anhydride (7.7 mg, 0.075 mmol). The reaction was stirred for 1 h at room temperature, and the reaction was purified without workup by prep HPLC on C-18 column eluting water:acetonitrile gradient buffered pH 10 to give two diastereomers: Peak #1 (Example 67): LCMS calculated for $C_{25}H_{30}ClN_8O_2$ (M+H)$^+$: m/z=509.2; found: 509.2; Peak #2 (Example 68): LCMS calculated for $C_{25}H_{30}ClN_8O_2$ (M+H)$^+$: m/z=509.2; found: 509.2.

Examples 69 and 70

9-[1-(4-Amino-3-methyl-1H-pyrazolo[3,4-d]pyrimidin-1-yl)ethyl]-7-chloro-2-ethyl-4-(2-hydroxyethyl)-2,3,4,5-tetrahydro-1,4-benzoxazepine-6-carbonitrile

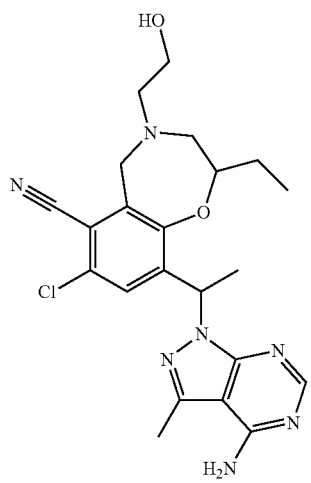 [SMILES: CCC1CN(CCO)Cc2c(C#N)c(Cl)cc(C(C)n3nc(C)c4c(N)ncnc43)c2O1]

Step 1. tert-Butyl (2-hydroxybutyl)carbamate

Di-tert-butyldicarbonate (3.7 g, 17 mmol) was added to a solution of 1-amino-2-butanol (1 g, 10 mmol) and N,N-diisopropylethylamine (3 g, 20 mmol) in methylene chloride (20 mL). The reaction was stirred for 3 h at room temperature and was partitioned between methylene chloride and water. The combined organic layer was washed with 1 N HCl, brine, dried over MgSO$_4$, filtered and concentrated to give crude tert-butyl (2-hydroxybutyl)carbamate (2.0 g, 90%).

Step 2. 9-[1-(4-Amino-3-methyl-1H-pyrazolo[3,4-d]pyrimidin-1-yl)ethyl]-7-chloro-2-ethyl-4-(2-hydroxyethyl)-2,3,4,5-tetrahydro-1,4-benzoxazepine-6-carbonitrile Using methods analogous to Example 61, but using tert-butyl (2-hydroxybutyl)carbamate, the title compound was prepared as a mixture of diastereomers. The reaction was purified by prep HPLC on C-18 column eluting water:acetonitrile gradient buffered pH 10 to give two diastereomers. Peak #1 (Example 69): LCMS calculated for $C_{22}H_{27}ClN_7O_2$ (M+H)$^+$: m/z=456.2; Found: 456.2; Peak #2 (Example 70): LCMS calculated for $C_{22}H_{27}ClN_7O_2$ (M+H)$^+$: m/z=456.2; Found: 456.2.

Examples 71 and 72

4-(1-Acetylazetidin-3-yl)-9-[1-(4-amino-3-methyl-1H-pyrazolo[3,4-d]pyrimidin-1-yl)ethyl]-7-chloro-6-fluoro-2-methyl-4,5-dihydro-1,4-benzoxazepin-3(2H)-one

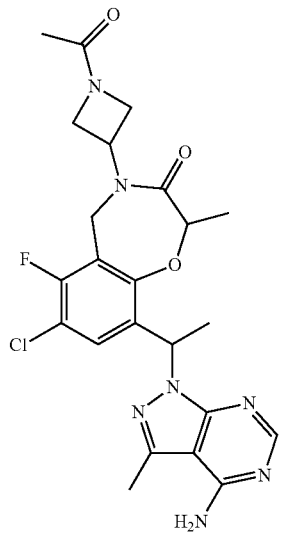 [SMILES: CC(=O)N1CC(N2Cc3c(F)c(Cl)cc(C(C)n4nc(C)c5c(N)ncnc54)c3OC(C)C2=O)C1]

Step 1. Ethyl 2-(6-acetyl-4-chloro-3-fluoro-2-iodophenoxy)propanoate

A solution of 1-(5-chloro-4-fluoro-2-hydroxy-3-iodophenyl)ethanone (5.00 g, 15.9 mmol) in N,N-dimethylformamide (80.0 mL) was treated with potassium carbonate (4.39 g, 31.8 mmol), followed by ethyl 2-bromopropanoate (2.48 mL, 19.1 mmol), and then stirred at 60° C. for 3 h. The reaction was stirred overnight at 60° C., and then worked up per the procedure below. The reaction was then re-submitted to the reaction conditions and stirred at 90° C. for 4 h. The reaction mixture was diluted with water and ethyl acetate. The organic layer was separated and washed with brine, dried over magnesium sulfate, filtered, and concentrated to give a crude residue. Purification by flash column chromatography (100% hexanes to 10% EtOAc/hexanes) gave the desired product (3.66 g, 56%) as a mixture of enantiomers. LCMS calculated for $C_{13}H_{14}ClFIO_4$ (M+H)$^+$: m/z=415.0; found: 414.9.

Step 2. Ethyl 2-[4-chloro-3-fluoro-2-iodo-6-(2-methyl-1,3-dioxolan-2-yl)phenoxy]propanoate A solution of ethyl 2-(6-acetyl-4-chloro-3-fluoro-2-iodophenoxy)propanoate (3.58 g, 8.63 mmol) and 1,2-ethanediol (1.20 mL, 21.6 mmol) in toluene (16.3 mL) was treated with p-toluenesulfonic acid monohydrate (246 mg, 1.30 mmol) and heated at reflux in a flask fitted with a Dean- Stark trap filled with sieves. The reaction mixture was cooled and poured into saturated sodium bicarbonate (150 mL) and extracted with ethyl acetate (2×200 mL). The combined organic layers were washed with brine, dried over sodium sulfate, filtered, and concentrated to give a crude residue. Purification by flash column chromatography (100% hexanes to 10% EtOAc/hexanes) gave the desired product (2.25 g, 57%) as a mixture of enantiomers. LCMS calculated for $C_{15}H_{18}ClFIO_5$ (M+H)$^+$: m/z=459.0; found: 459.0.

Step 3. Ethyl 2-[4-chloro-3-fluoro-6-(2-methyl-1,3-dioxolan-2-yl)-2-vinylphenoxy]propanoate A mixture of ethyl 2-[4-chloro-3-fluoro-2-iodo-6-(2-methyl-1,3-dioxolan-2-yl)phenoxy]propanoate (1.83 g, 3.99 mmol), 4,4,5,5-tetramethyl-2-vinyl-1,3,2-dioxaborolane (0.880 mL, 5.19 mmol), and potassium carbonate (1.65 g, 12.0 mmol) in 1,4-dioxane (15.6 mL) and water (7.8 mL) was degassed with nitrogen for 10 min. The reaction mixture was treated with [1,1'-bis(diphenylphosphino)ferrocene]dichloropalladium(II) complex with dichloromethane (1:1) (163 mg, 0.199 mmol), degassed with nitrogen for another 10 min, and heated at 80° C. for 2 h. The reaction mixture was filtered through Celite and washed with ethyl acetate. The filtrate was poured into water. The aqueous layer was separated and re-extracted with ethyl acetate. The combined organic extracts were washed with brine, dried over sodium sulfate, filtered, and concentrated give a crude residue. Purification by flash column chromatography (100% hexanes to 15% EtOAc/hexanes) gave the desired product (2.25 g, 57%) as a mixture of enantiomers. LCMS calculated for $C_{17}H_{21}ClFO_5$ (M+H)$^+$: m/z=359.1; found: 359.1.

Step 4. Ethyl 2-[4-chloro-3-fluoro-2-formyl-6-(2-methyl-1,3-dioxolan-2-yl)phenoxy]propanoate A solution of ethyl 2-[4-chloro-3-fluoro-6-(2-methyl-1,3-dioxolan-2-yl)-2-vinylphenoxy]propanoate (400 mg, 1.11 mmol) in methylene chloride (40 mL) at −78° C. was treated with ozone until a purple color persisted. The reaction mixture was purged with oxygen, treated with dimethyl sulfide (1 mL) and warmed to room temperature. The reaction mixture was concentrated to give the crude product (392 mg, 98%) as a mixture of enantiomers that was used without further purification. LCMS calculated for $C_{16}H_{19}ClFO_6$ (M+H)$^+$: m/z=361.1; found: 361.1.

Step 5. 1-Acetylazetidin-3-amine hydrochloride

A solution of tert-butyl azetidin-3-ylcarbamate (1.00 g, 5.81 mmol) [Ark Pharma, AK26432] in tetrahydrofuran (50 mL) was treated with triethylamine (1.6 mL, 11.6 mmol) followed by N,N-dimethylformamide (15 mL) and cooled to 0° C. The reaction mixture was treated with acetyl chloride (495 µL, 6.97 mmol) and stirred overnight at room temperature. The reaction mixture was diluted with ether and washed with water and brine, dried over magnesium sulfate, filtered, and concentrated give a crude residue that was used immediately without purification. The intermediate azetidine was diluted with methylene chloride (30 mL), treated with 4.0 M hydrogen chloride in dioxane (22.0 mL, 88.0 mmol), and stirred at rt for 30 min. The reaction mixture was diluted with ether and the precipitated solid was collected by filtration in order to give the desired product (550 mg, 63%) as a HCl salt. LCMS calculated for $C_5H_{11}N_2O$ (M+H)$^+$: m/z=115.1; found: 115.2.

Step 6. 4-(1-Acetylazetidin-3-yl)-7-chloro-6-fluoro-2-methyl-9-(2-methyl-1,3-dioxolan-2-yl)-4,5-dihydro-1,4-benzoxazepin-3(2H)-one A solution of ethyl 2-[4-chloro-3-fluoro-2-formyl-6-(2-methyl-1,3-dioxolan-2-yl)phenoxy]propanoate (392 mg, 1.09 mmol) in methanol (21 mL) was treated with sodium cyanoborohydride (171 mg, 2.72 mmol) followed by 1-acetylazetidin-3-amine hydrochloride (360 mg, 2.39 mmol) and stirred at room temperature overnight. The reaction mixture was quenched with acetic acid (200 µL) and concentrated in vacuo. The residue was diluted with toluene (60 mL) and heated at 110° C. for 2 h. The solvent was concentrated in vacuo, and the residue was purified via preparative LCMS (XBridge C18 column, eluting with a gradient of acetonitrile/water containing 0.1% ammonium hydroxide, at flow rate of 60 mL/min) to give the desired product (142 mg, 32%) as a mixture of enantiomers. LCMS calculated for $C_{19}H_{23}ClFN_2O_5$ (M+H)$^+$: m/z=413.1; found: 413.1.

Step 7. 9-Acetyl-4-(1-acetylazetidin-3-yl)-7-chloro-6-fluoro-2-methyl-4,5-dihydro-1,4-benzoxazepin-3 (2H)-one A solution of 4-(1-acetylazetidin-3-yl)-7-chloro-6-fluoro-2-methyl-9-(2-methyl-1,3-dioxolan-2-yl)-4,5-dihydro-1,4-benzoxazepin-3(2H)-one (190 mg, 0.460 mmol) in methanol (20 mL) and was treated with 6.0 M hydrogen chloride in water (1.15 mL, 6.90 mmol) and stirred at room temperature for 3 h. The reaction mixture was diluted with ethyl acetate and water. The organic layer was separated, washed with brine, dried over sodium sulfate, filtered, and concentrated to give the desired product (132 mg, 78%) as a mixture of enantiomers that was used without further purification. LCMS calculated for $C_{17}H_{19}ClFN_2O_4$ (M+H)$^+$: m/z=369.1; found: 369.1.

Step 8. 4-(1-Acetylazetidin-3-yl)-7-chloro-6-fluoro-9-(1-hydroxyethyl)-2-methyl-4,5-dihydro-1,4-benzoxazepin-3(2H)-one A solution of 9-acetyl-4-(1-acetylazetidin-3-yl)-7-chloro-6-fluoro-2-methyl-4,5-dihydro-1,4-benzoxazepin-3(2H)-one (112 mg, 0.304 mmol) in methanol (5.6 mL) at −10° C. was treated with sodium tetrahydroborate (17 mg, 0.456 mmol) and stirred for 30 min at 0° C. The reaction mixture was quenched with acetic acid (86 µL, 1.52 mmol) at 0° C. and then diluted with ethyl acetate and water. The organic layer was separated, washed with brine, dried over sodium sulfate, filtered, and concentrated to give a crude residue. Purification via preparative LCMS (XBridge C18 column, eluting with a gradient of acetonitrile/water containing 0.1% ammonium hydroxide, at flow rate of 60 mL/min) gave two fractions. Each fraction contained a pair of enantiomers: peak 1 (30 mg, 27%) and peak 2 (50 mg, 44%). Peak 1: LCMS calculated for $C_{17}H_{21}ClFN_2O_4$ (M+H)$^+$: m/z=371.1; found: 371.1. Peak 2: LCMS calculated for $C_{17}H_{21}ClFN_2O_4$ (M+H)$^+$: m/z=371.1; found: 371.1.

Step 9. 4-(1-Acetylazetidin-3-yl)-9-[1-(4-amino-3-methyl-H-pyrazolo[3,4-d]pyrimidin-1-yl)ethyl]-7-chloro-6-fluoro-2-methyl-4,5-dihydro-1,4-benzoxazepin-3(2H)-one The two fractions from step 8 were processed individually and identically. A suspension of 4-(1-acetylazetidin-3-yl)-7-chloro-6-fluoro-9-(1-hydroxyethyl)-2-methyl-4,5-dihydro- 1,4-benzoxazepin-3(2H)-one (49.0 mg, 0.132 mmol) (step 8, peak 2) and N,N-dimethylformamide (1.0 μL, 0.013 mmol) in methylene chloride (1.1 mL) was treated with thionyl chloride (24 μL, 0.330 mmol) and stirred for 2 h. The reaction mixture was added to ice cooled saturated sodium bicarbonate and diluted with dichloromethane. The organic layer was separated, washed with brine, dried over sodium sulfate, filtered, and concentrated to give the intermediate chloride that was used immediately. A solution of the chloro intermediate in N,N-dimethylformamide (2.0 mL) and was treated with 3-methyl-1H-pyrazolo[3,4-d]pyrimidin-4-amine (30 mg, 0.198 mmol) and cesium carbonate (86.1 mg, 0.264 mmol) and heated in a sealed tube at 80° C. for 2 h. The reaction mixture was purified via preparative LCMS (XBridge C18 column, eluting with a gradient of acetonitrile/water containing 0.1% ammonium hydroxide, at flow rate of 60 mL/min) to give the desired product (19 mg, 29%) as a mixture of enantiomers. Product produced starting from the product of step 8, peak 1 (Example 71): LCMS calculated for $C_{23}H_{26}ClFN_7O_3$ (M+H)+: m/z=502.2; found: 502.1; $^1$H NMR (400 MHz, DMSO-$d_6$) δ 8.20 (s, 0.4H), 8.16 (s, 0.6H), 7.74 (br s, 2H), 7.43 (d, J=8.2 Hz, 0.4H), 7.20 (d, J=8.3 Hz, 0.6H), 6.31-6.01 (m, 1H), 5.67-5.55 (m, 0.6H), 5.38-5.25 (m, 0.4H), 5.22-5.04 (m, 2H), 4.65-4.48 (m, 1H), 4.38-4.26 (m, 0.6H), 4.22-4.13 (m, 0.4H), 4.12-3.97 (m, 1H), 3.94-3.79 (m, 1H), 3.74-3.21 (m, 1H), 2.56 (s, 1.8H), 2.53 (s, 1.2H), 1.81-1.62 (m, 6H), 1.40 (d, J=6.2 Hz, 1.8H), 1.23-1.13 (m, 1.2H); Product produced starting from the product of step 8, peak 2 (Example 72): LCMS calculated for $C_{23}H_{26}ClFN_7O_3$ (M+H)+: m/z=502.2; found: 502.1; $^1$H NMR (300 MHz, DMSO-$d_6$) δ 8.15 (s, 0.9H), 8.12 (s, 0.1H), 7.47 (br s, 2H), 7.41 (d, J=8.5 Hz, 0.9H), 7.17 (d, J=8.5 Hz, 0.1H), 6.25-6.06 (m, 1H), 5.71-5.52 (m, 0.1H), 5.39-5.23 (m, 0.9H), 5.22-5.01 (m, 2H), 4.66-4.47 (m, 1H), 4.41-4.25 (m, 0.9H), 4.23-4.12 (m, 0.1H), 4.11-3.96 (m, 1H), 3.94-3.77 (m, 1H), 3.67-3.54 (m, 1H), 2.55 (s, 0.3H), 2.52 (s, 2.7H), 1.82-1.61 (m, 6H), 1.40 (d, J=6.2 Hz, 0.3H), 1.27-1.16 (m, 2.7H).

Compounds Synthesized

Experimental procedures for compounds below are summarized in Table 1 below. Mass spectrometry data and $^1$H NMR data for the compounds are summarized in Table 2.

TABLE 1

| Ex. No. | Name | $R^x$ | $R^w$ | $R^{3b}$ | $R^4$ | $R^5$ | Proc.$^a$ |
|---|---|---|---|---|---|---|---|
| 73 | 3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]-N,N-dimethylazetidine-1-carboxamide | H | H | (azetidinyl-C(=O)-N(CH₃)₂) | F | Cl | 34 |
| 74 | 3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]-N,N-dimethylazetidine-1-sulfonamide | H | H | (azetidinyl-S(=O)₂-N(CH₃)₂) | F | Cl | 34 |
| 75 | 1-(1-{7-chloro-6-fluoro-2-methyl-4-[1-(methylsulfonyl)azetidin-3-yl]-2,3,4,5-tetrahydro-1,4-benzoxazepin-9-yl}ethyl)-3-methyl-1H-pyrazolo[3,4-d]pyrimidin-4-amine | Me | H | (azetidinyl-S(=O)₂-CH₃) | F | Cl | 28 |

TABLE 1-continued

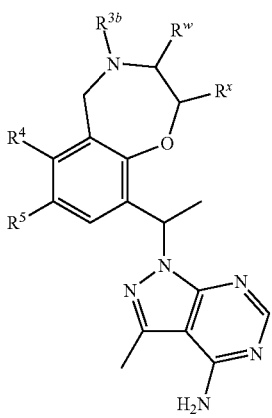

| Ex. No. | Name | $R^x$ | $R^w$ | $R^{3b}$ | $R^4$ | $R^5$ | Proc.[a] |
|---|---|---|---|---|---|---|---|
| 76 | 1-{1-[7-chloro-6-fluoro-2-methyl-4-(1-propionylazetidin-3-yl)-2,3,4,5-tetrahydro-1,4-benzoxazepin-9-yl]ethyl}-3-methyl-1H-pyrazolo[3,4-d]pyrimidin-4-amine | Me | H | azetidine with N-C(=O)-CH2CH3 | F | Cl | 28 |
| 77, 78 | (2R)-1-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]propan-2-ol | Me | H | CH2-CH(OH)-CH3 (R) | F | Cl | 50 Peak 1 (Ex. 77) Peak 2 (Ex. 78) |
| 79, 80 | methyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate | Me | H | azetidine with N-C(=O)-OCH3 | F | Cl | 28 Peak 1 (Ex. 79) Peak 2 (Ex. 80) |
| 81, 82 | 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-sulfonamide | Me | H | azetidine with N-S(=O)2-NH2 | F | Cl | 28 Peak 1 (Ex. 81) Peak 2 (Ex. 82) |
| 83, 84 | 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxamide | Me | H | azetidine with N-C(=O)-NH2 | F | Cl | 28 Peak 1 (Ex. 83) Peak 2 (Ex. 84) |
| 85 | (2S)-1-{3-[(2S)-9-[(1S)-1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidin-1-yl}propan-2-ol | Me | H | azetidine with N-CH2-CH(OH)-CH3 (S) | F | Cl | 50 |

TABLE 1-continued

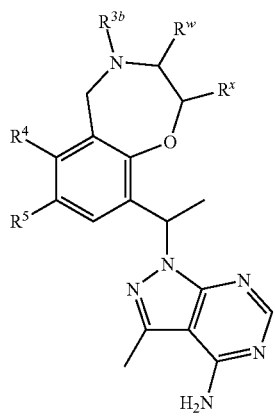

| Ex. No. | Name | R$^x$ | R$^w$ | R$^{3b}$ | R$^4$ | R$^5$ | Proc.$^a$ |
|---|---|---|---|---|---|---|---|
| 86 | (2R)-1-{3-[(2S)-9-[(1S)-1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidin-1-yl}propan-2-ol | Me | H | ![azetidine with CH2-CH(OH)-CH3] | F | Cl | 50 |
| 87, 88 | 2-{3-[(2S)-9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidin-1-yl}acetamide | Me | H | ![azetidine-CH2-C(O)NH2] | F | Cl | 28 Peak 1 (Ex. 87) Peak 2 (Ex. 88) |
| 89 | 9-[1-(4-amino-3-methyl-1H-pyrazolo[3,4-d]pyrimidin-1-yl)ethyl]-7-chloro-4-(1-propionylazetidin-3-yl)-2,3,4,5-tetrahydro-1,4-benzoxazepine-6-carbonitrile | H | H | ![azetidine-C(O)Et] | CN | Cl | 46 |
| 90 | 9-[1-(4-amino-3-methyl-1H-pyrazolo[3,4-d]pyrimidin-1-yl)ethyl]-7-chloro-4-[1-(methylsulfonyl)azetidin-3-yl]-2,3,4,5-tetrahydro-1,4-benzoxazepine-6-carbonitrile | H | H | ![azetidine-SO2Me] | CN | Cl | 46 |
| 91 | 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]-N-isopropylazetidine-1-carboxamide | H | H | ![azetidine-C(O)NHiPr] | CN | Cl | 46 |
| 92 | ethyl 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]azetidine-1-carboxylate | H | H | ![azetidine-C(O)OEt] | CN | Cl | 46 |

TABLE 1-continued

| Ex. No. | Name | R$^x$ | R$^w$ | R$^{3b}$ | R$^4$ | R$^5$ | Proc.$^a$ |
|---|---|---|---|---|---|---|---|
| 93, 94 | 9-[1-(4-amino-3-methyl-1H-pyrazolo[3,4-d]pyrimidin-1-yl)ethyl]-7-chloro-2-methyl-4-[1-(methylsulfonyl)azetidin-3-yl]-2,3,4,5-tetrahydro-1,4-benzoxazepine-6-carbonitrile | Me | H | 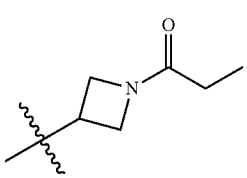 [SMILES: *C1CN(C(=O)CC)C1] | CN | Cl | 48 Peak 1 (Ex. 93) Peak 2 (Ex. 94) |
| 95, 96 | 9-[1-(4-amino-3-methyl-1H-pyrazolo[3,4-d]pyrimidin-1-yl)ethyl]-7-chloro-2-methyl-4-(1-propionylazetidin-3-yl)-2,3,4,5-tetrahydro-1,4-benzoxazepine-6-carbonitrile | Me | H | 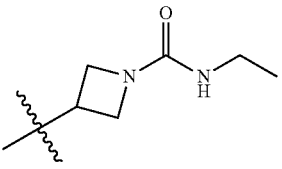 [SMILES: *C1CN(C(=O)NCC)C1] | CN | Cl | 48 Peak 1 (Ex. 95) Peak 2 (Ex. 96) |
| 97, 98 | 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-ethylazetidine-1-carboxamide | Me | H | 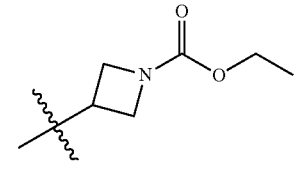 [SMILES: *C1CN(C(=O)OCC)C1] | CN | Cl | 48 Peak 1 (Ex. 97) Peak 2 (Ex. 98) |
| 99, 100 | ethyl 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidine-1-carboxylate | Me | H | 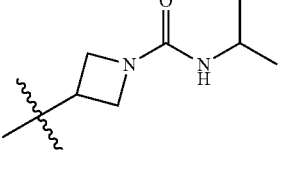 | CN | Cl | 48 Peak 1 (Ex. 99) Peak 2 (Ex. 100) |
| 101, 102 | 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-isopropylazetidine-1-carboxamide | Me | H | 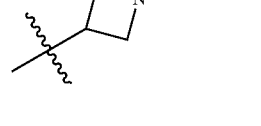 | CN | Cl | 48 Peak 1 (Ex. 101) Peak 2 (Ex. 102) |
| 103, 104 | 9-[1-(4-amino-3-methyl-1H-pyrazolo[3,4-d]pyrimidin-1-yl)ethyl]-7-chloro-4-[1-(2-hydroxyethyl)azetidin-3-yl]-2-methyl-2,3,4,5-tetrahydro-1,4-benzoxazepine-6-carbonitrile | Me | H |  | CN | Cl | 50 Peak 1 (Ex. 103) Peak 2 (Ex. 104) |

TABLE 1-continued

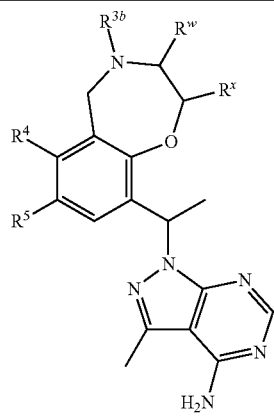

| Ex. No. | Name | R$^x$ | R$^w$ | R$^{3b}$ | R$^4$ | R$^5$ | Proc.$^a$ |
|---|---|---|---|---|---|---|---|
| 105, 106 | 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N,N-dimethylazetidine-1-sulfonamide | Me | H | azetidine-sulfonamide group | CN | Cl | 48 Peak 1 (Ex. 105) Peak 2 (Ex. 106) |
| 107, 108 | 9-[1-(4-amino-3-methyl-1H-pyrazolo[3,4-d]pyrimidin-1-yl)ethyl]-7-chloro-4-(cyanomethyl)-2-methyl-2,3,4,5-tetrahydro-1,4-benzoxazepine-6-carbonitrile | Me | H | CH$_2$CN group | CN | Cl | 59 Peak 1 (Ex. 107) Peak 2 (Ex. 108) |
| 109, 110 | 2-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]acetamide | Me | H | CH$_2$C(O)NH$_2$ group | CN | Cl | 59 Peak 1 (Ex. 109) Peak 2 (Ex. 110) |
| 111, 112 | 9-[1-(4-amino-3-methyl-1H-pyrazolo[3,4-d]pyrimidin-1-yl)ethyl]-7-chloro-4-(2-methoxyethyl)-2-methyl-2,3,4,5-tetrahydro-1,4-benzoxazepine-6-carbonitrile | Me | H | CH$_2$CH$_2$OMe group | CN | Cl | 59 Peak 1 (Ex. 111) Peak 2 (Ex. 112) |
| 113, 114, 115 | 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-methylcyclobutane-carboxamide | Me | H | cyclobutane-N-methylcarboxamide group | CN | Cl | 67 Peak 1 (Ex. 113) Peak 2 (Ex. 114) Peak 3 (Ex. 115) |

$^a$Compound made by an analogous procedure to the indicated Example procedure. Peak information indicates the order in which the diasteromers eluted under the analogous column conditions.

TABLE 2

| Ex. No. | MS [M+H]$^+$ | $^1$H NMR Spectra |
|---|---|---|
| 73 | 503.1 | $^1$H NMR (300 MHz, DMSO-d$_6$): δ 8.14 (s, 1 H), 7.31 (m, 1 H), 6.22 (m, 1 H), 4.20 (m, 1 H), 3.87 (m, 3 H), 3.60 (m, 6 H), 2.80 (m, 2 H), 2.71 (s, 6 H), 2.54 (s, 3 H), 1.69 (m, 3 H) |
| 74 | 539.2 | $^1$H NMR (300 MHz, DMSO-d$_6$): δ 8.12 (s, 1 H), 7.35 (m, 1 H), 6.22 (m, 1 H), 3.95 (m, 1 H), 3.77 (m, 2 H), 3.61 (m, 4 H), 2.80 (m, 2 H), 2.69 (s, 6 H), 2.55 (s, 3 H), 1.69 (m, 3 H) |
| 75 | 524.1 | $^1$H NMR (300 MHz, CD$_3$OD): δ 8.12 (s, 1 H), 7.32 (m, 1 H), 6.38 (m, 1 H), 3.93 (m, 3 H), 3.80 (m, 3 H), 3.52 (m, 2 H), 2.91 (s, 3 H), 2.61 (s, 3 H), 1.79 (m, 3 H), 1.31 (m, 3 H) |

TABLE 2-continued

| Ex. No. | MS [M+H]+ | 1H NMR Spectra |
|---|---|---|
| 76 | 502.2 | 1H NMR (300 MHz, CD3OD): δ 8.14 (s, 1 H), 7.33 (m, 1 H), 6.39 (m, 1 H), 4.20 (m, 1 H), 3.99 (m, 3 H), 3.79 (m, 2 H), 3.60 (m, 1 H), 3.49 (m, 1 H), 2.12 (m, 2 H), 1.78 (m, 3 H), 1.31 (m, 3 H), 1.05 (m, 3 H) |
| 77 | 449.2 | |
| 78 | 449.2 | |
| 79 | 504.1 | |
| 80 | 504.1 | 1H NMR (300 MHz, DMSO-d6): δ 8.11 (s, 1 H), 7.39 (m, 1 H), 6.28 (m, 1 H), 3.82 (m, 5 H), 3.65 (m, 3 H), 3.50 (s, 3 H), 2.85 (m, 1 H), 2.63 (m, 1 H), 2.55 (s, 3 H), 1.66 (m, 3 H), 1.29 (m, 3 H) |
| 81 | 525.1 | |
| 82 | 525.1 | 1H NMR (300 MHz, DMSO-d6): δ 8.11 (s, 1 H), 7.40 (m, 1 H), 6.85 (s, 2 H), 6.28 (m, 1 H), 3.82 (m, 3 H), 3.69 (m, 2 H), 3.52 (m, 3 H), 2.80 (m, 1 H), 2.62 (m, 1 H), 2.55 (s, 3 H), 1.67 (m, 3 H), 1.28 (m, 3 H) |
| 83 | 489.2 | |
| 84 | 489.2 | |
| 85 | 504.2 | |
| 86 | 504.2 | |
| 87 | 503.2 | |
| 88 | 503.2 | |
| 89 | 495.1 | |
| 90 | 517.1[b] | |
| 91 | 524.2 | |
| 92 | 511.1 | |
| 93 | 531.1 | |
| 94 | 531.1 | |
| 95 | 509.3 | |
| 96 | 509.2 | |
| 97 | 524.3 | |
| 98 | 524.2 | |
| 99 | 525.2 | |
| 100 | 525.3 | |
| 101 | 538.2 | |
| 102 | 538.2 | |
| 103 | 497.2 | |
| 104 | 497.1 | |
| 105 | 560.1 | |
| 106 | 560.1 | |
| 107 | 437.1 | |
| 108 | 437.2 | |
| 109 | 455.2 | |
| 110 | 455.1 | |
| 111 | 456.2 | |
| 112 | 456.1 | |
| 113 | 509.1 | |
| 114 | 509.1 | |
| 115 | 509.2 | |

[b][M + Na]

Example A1

PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5)P3 Detector Protein is purchased from Echelon Biosciences (Salt Lake City, Utah). AlphaScreen™ GST Detection Kit including donor and acceptor beads is purchased from PerkinElmer Life Sciences (Waltham, Mass.). PI3Kδ (p110δ/p85α) is purchased from Millipore (Bedford, Mass.). ATP, MgCl$_2$, DTT, EDTA, HEPES and CHAPS are purchased from Sigma-Aldrich (St. Louis, Mo.).
AlphaScreen™ Assay for PI3Kδ

The kinase reaction are conducted in 384-well REMP plate from Thermo Fisher Scientific in a final volume of 40 μL. Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5 mM MgCl$_2$, 50 mM NaCl, 5 mM DTT and CHAPS 0.04%. Reactions are initiated by the addition of ATP, the final reaction mixture consisted of 20 μM PIP2, 20 μM ATP, 1.2 nM PI3Kδ are incubated for 20 minutes. 10 μL of reaction mixture are then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/ml. After plate sealing, the plates are incubated in a dark location at room temperature for 2 hours. The activity of the product is determined on Fusion-alpha microplate reader (Perkin-Elmer). IC$_{50}$ determination is performed by fitting the curve of percent control activity versus the log of the inhibitor concentration using the GraphPad Prism 3.0 software. Compounds with an IC$_{50}$ of less than 10 μM in in the assay of Example A1 are considered to be active.

Example A2

PI3K Enzyme Assay

Materials: Lipid kinase substrate, phosphoinositol-4,5-bisphosphate (PIP2), are purchased from Echelon Biosciences (Salt Lake City, Utah). PI3K isoforms α, β, δ and γ are purchased from Millipore (Bedford, Mass.). ATP, MgCl$_2$, DTT, EDTA, MOPS and CHAPS are purchased from Sigma-Aldrich (St. Louis, Mo.).

The kinase reaction are conducted in clear-bottom 96-well plate from Thermo Fisher Scientific in a final volume of 24 μL. Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM MgCl$_2$, 5 mM DTT and CHAPS 0.03%. The reaction mixture is prepared containing 50 μM PIP2, kinase and varying concentration of inhibitors. Reactions are initiated by the addition of ATP containing 2.2 μCi [γ-$^{33}$P]ATP to a final concentration of 1000 μM. The final concentration of PI3K isoforms α, β, δ and γ in the assay were 1.3, 9.4, 2.9 and 10.8 nM, respectively. Reactions are incubated for 180 minutes and terminated by the addition of 100 μL of 1 M potassium phosphate pH 8.0, 30 mM EDTA quench buffer. A 100 μL aliquot of the reaction solution are then transferred to 96-well Millipore MultiScreen IP 0.45 μm PVDF filter plate (The filter plate is prewetted with 200 μL 100% ethanol, distilled water, and 1 M potassium phosphate pH 8.0, respectively). The filter plate is aspirated on a Millipore Manifold under vacuum and washed with 18×200 μL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 μL Microscint 20 scintillation cocktail (Perkin Elmer) in each well. After the plate sealing, the radioactivity of the product is determined by scintillation counting on Topcount (Perkin-Elmer). IC$_{50}$ determination is performed by fitting the curve of percent control activity versus the log of the inhibitor concentration using the GraphPad Prism 3.0 software. Compounds with an IC$_{50}$ of less than 10 μM in in the assay of Example A2 are considered to be active.

Example A3

PI3Kδ Scintillation Proximity Assay

Materials

[γ-$^{33}$P]ATP(10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P]ATP, 4 nM PI3Kδ. Reactions were incubated for 210 min and terminated by the addition of 40 μL SPA beads suspended in quench buffer: 150 mM potassium phosphate pH 8.0, 20% glycerol. 25 mM EDTA, 400 μM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism 3.0 software. Compounds with an IC$_{50}$ of less than 10 μM in in the assay of Example A3 are considered to be active. IC$_{50}$ data for Examples 1-25 is presented in Table 3 for PI3Kδ as determined by the assay of Example A2 or A3 as indicated

TABLE 3

| Example # | PI3Kδ IC$_{50}$ (nM)* | Assay |
|---|---|---|
| 1 | ++ | A3 |
| 2 | + | A3 |
| 3 | + | A3 |
| 4 | + | A3 |
| 5 | + | A3 |
| 6 | + | A3 |
| 7 | + | A3 |
| 8 | + | A3 |
| 9 | + | A3 |
| 10 | + | A3 |
| 11 | + | A3 |
| 12 | + | A3 |
| 13 | + | A3 |
| 14 | + | A3 |
| 15 | + | A3 |
| 16 | + | A3 |
| 17 | + | A3 |
| 18 | + | A3 |
| 19 | + | A3 |
| 20 | + | A3 |
| 21 | + | A3 |
| 22 | + | A3 |
| 23 | + | A3 |
| 24 | + | A3 |
| 25 | + | A3 |

TABLE 3-continued

| Example # | PI3Kδ IC$_{50}$ (nM)* | Assay |
|---|---|---|
| 26 | + | A2 |
| 27 | + | A2 |
| 28 | + | A2 |
| 29 | + | A2 |
| 30 | + | A2 |
| 31 | +++++ | A2 |
| 32 | + | A2 |
| 33 | ++ | A2 |
| 34 | + | A2 |
| 35 | + | A2 |
| 36 | +++ | A2 |
| 37 | + | A2 |
| 38 | +++++ | A2 |
| 39 | +++++ | A2 |
| 40 | + | A2 |
| 41 | + | A2 |
| 42 | + | A2 |
| 43 | + | A2 |
| 44 | + | A2 |
| 45 | + | A2 |
| 46 | + | A2 |
| 47 | + | A2 |
| 48 | ++ | A2 |
| 49 | + | A2 |
| 50 | + | A2 |
| 51 | + | A2 |
| 52 | + | A2 |
| 53 | + | A2 |
| 54 | + | A2 |
| 55 | + | A2 |
| 56 | + | A2 |
| 57 | + | A2 |
| 58 | + | A2 |
| 59 | + | A2 |
| 60 | + | A2 |
| 61 | +++++ | A2 |
| 62 | + | A2 |
| 63 | + | A2 |
| 64 | ++ | A2 |
| 65 | + | A2 |
| 66 | + | A2 |
| 67 | + | A2 |
| 68 | + | A2 |
| 69 | + | A2 |
| 70 | + | A2 |
| 72 | ++ | A2 |
| 73 | + | A2 |
| 74 | + | A2 |
| 75 | + | A2 |
| 76 | + | A2 |
| 77 | + | A2 |
| 78 | + | A2 |
| 79 | + | A2 |
| 80 | + | A2 |
| 81 | + | A2 |
| 82 | + | A2 |
| 83 | + | A2 |
| 84 | + | A2 |
| 85 | + | A2 |
| 86 | + | A2 |
| 87 | ++ | A2 |
| 88 | + | A2 |
| 89 | + | A2 |
| 90 | + | A2 |
| 91 | + | A2 |
| 92 | + | A2 |
| 93 | + | A2 |
| 94 | + | A2 |
| 95 | + | A2 |
| 96 | + | A2 |
| 97 | + | A2 |
| 98 | + | A2 |
| 99 | + | A2 |
| 100 | + | A2 |
| 101 | + | A2 |
| 102 | + | A2 |
| 103 | + | A2 |
| 104 | + | A2 |

TABLE 3-continued

| Example # | PI3Kδ IC$_{50}$ (nM)* | Assay |
|---|---|---|
| 105 | + | A2 |
| 106 | + | A2 |
| 107 | + | A2 |
| 108 | + | A2 |
| 109 | + | A2 |
| 110 | + | A2 |
| 111 | + | A2 |
| 112 | + | A2 |
| 113 | + | A2 |
| 114 | + | A2 |
| 115 | + | A2 |

*column symbols:
+ refers to ≤100 nM,
++ refers to >100 nM to 500 nM,
+++ refers to >500 nM to 1000 nM,
++++ refers to >1000 nM to 10,000 nM,
+++++ refers to >800 nM

Example B1

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells (2×10$^5$/well/200 μL) are cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.) in the presence of different amount of test compounds for three days. [$^3$H]-thymidine (1 μCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience). Compounds with an IC$_{50}$ of less than 10 μM in in the assay of Example B1 are considered to be active.

Example B2

Pfeiffer Cell Proliferation Assay

Pfeiffer cell line (diffuse large B cell lymphoma) are purchased from ATCC (Manassas, Va.) and maintained in the culture medium recommended (RPMI and 10% FBS). To measure the anti-proliferation activity of the compounds, the Pfeiffer cells are plated with the culture medium (2×10$^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS is then added to the cell culture for an additional 12 hours before the incorporated radioactivity is separated by filtration with water through GF/B filters (Packard Bioscience, Meridenj, Conn.) and measured by liquid scintillation counting with a TopCount (Packard Bioscience). Compounds with an IC$_{50}$ of less than 10 μM in in the assay of Example B2 are considered to be active.

Example B3

SUDHL-6 Cell Proliferation Assay

SUDHL-6 cell line (diffuse large B cell lymphoma) was purchased from ATCC (Manassas, Va.) and maintained in the culture medium recommended (RPMI and 10% FBS). To measure the anti-proliferation activity of the compounds through ATP quantitation, the SUDHL-6 cells was plated with the culture medium (5000 cells/well/per 200 μl) into 96-well polystyrene clear black tissue culture plate (Greiner-bio-one through VWR, NJ) in the presence or absence of a concentration range of test compounds. After 3 days, Cell Titer-GLO Luminescent (Promega, Madison, Wis.) cell culture agent was added to each well for 10 minutes at room temperature to stabilize the luminescent signal. This determines the number of viable cells in culture based on quantitation of the ATP present, which signals the presence of metabolically active cells. Luminescence was measured with the TopCount 384 (Packard Bioscience through Perkin Elmer, Boston, Mass.). Compounds with an IC$_{50}$ of less than 10 μM in in the assay of Example B3 are considered to be active. IC$_{50}$ data for the Examples is presented in Table 4 determined by the assay of Example B3.

TABLE 4

| Example # | SUDHL IC$_{50}$ (nM)* |
|---|---|
| 3 | + |
| 4 | + |
| 5 | + |
| 6 | + |
| 10 | + |
| 12 | + |
| 13 | + |
| 18 | ++ |
| 20 | + |
| 21 | + |
| 23 | + |
| 24 | ++ |
| 26 | + |
| 27 | + |
| 28 | + |
| 29 | + |
| 30 | + |
| 32 | + |
| 34 | + |
| 35 | + |
| 37 | + |
| 40 | + |
| 41 | + |
| 42 | + |
| 44 | + |
| 45 | + |
| 46 | + |
| 47 | + |
| 48 | ++ |
| 49 | + |
| 50 | + |
| 51 | + |
| 53 | + |
| 54 | + |
| 55 | + |
| 56 | + |
| 57 | + |
| 58 | + |
| 60 | + |
| 62 | + |
| 63 | + |
| 65 | + |
| 66 | + |
| 67 | + |
| 68 | + |
| 69 | + |
| 70 | + |

TABLE 4-continued

| Example # | SUDHL IC$_{50}$ (nM)* |
|---|---|
| 71 | ++ |
| 73 | + |
| 74 | ++ |
| 75 | + |
| 76 | + |
| 78 | + |
| 80 | + |
| 82 | + |
| 83 | + |
| 84 | + |
| 85 | + |
| 86 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 104 | + |
| 105 | + |
| 106 | + |
| 108 | + |
| 110 | + |
| 112 | + |
| 114 | + |
| 115 | + |

*column symbols:
+ refers to ≤500 nM,
++ refers to >500 nM to 1000 nM,
+++ refers to >1000 nM to 2000 nM,
++++ refers to >2000 nM to 10,000 nM

Example C

Akt Phosphorylation Assay

Ramos cells (B lymphocyte from Burkitts lymphoma) are obtained from ATCC (Manassas, Va.) and maintained in RPMI1640 and 10% FBS. The cells (3×10$^7$ cells/tube/3 mL in RPMI) are incubated with different amounts of test compounds for 2 hrs at 37° C. and then stimulated with goat F(ab')2 anti-human IgM (5 μg/mL) (Invitrogen) for 17 minutes in a 37° C. water bath. The stimulated cells are spun down at 4° C. with centrifugation and whole cell extracts are prepared using 300 μL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula II:

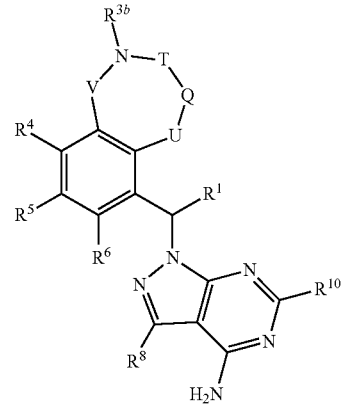

or a pharmaceutically acceptable salt thereof, wherein:
V is CH$_2$;
T is CH$_2$, or CH(CH$_3$);
Q is CH$_2$, CH(CH$_3$), or CH(CH$_2$CH$_3$);
U is O;
R$^1$ is C$_{1-3}$ alkyl;
R$^{3b}$ is H, Cy, —(C$_{1-3}$alkylene)-Cy, C$_{1-6}$ alkyl, C$_{2-6}$ alkenyl, C$_{2-6}$ alkynyl, C$_{1-6}$ haloalkyl, C(=O)R$^b$, C(=O)NR$^c$R$^d$, C(=O)OR$^a$, S(=O)$_2$R$^b$, or S(=O)$_2$NR$^c$R$^d$; wherein said C$_{1-6}$ alkyl, C$_{2-6}$ alkenyl, and C$_{2-6}$ alkynyl are optionally substituted by 1, 2, 3, or 4 independently selected R$^{13b}$ groups;
R$^4$ is H, halo, OH, CN, C$_{1-4}$ alkyl, C$_{1-4}$ haloalkyl, C$_{1-4}$ alkoxy, or C$_{1-4}$ haloalkoxy;
R$^5$ is halo, OH, CN, C$_{1-4}$ alkyl, C$_{1-4}$ haloalkyl, C$_{1-4}$ alkoxy, C$_{1-4}$ haloalkoxy, or cyclopropyl;
R$^6$ is H;
R$^8$ is H, halo, —OH, —CN, C$_{1-6}$ alkyl, or C$_{1-6}$ haloalkyl;
R$^{10}$ is H or C$_{1-4}$ alkyl;
each R$^{11}$ is independently selected from halo, OH, NO$_2$, CN, C$_{1-3}$ alkyl, C$_{1-3}$ haloalkyl, C$_{1-3}$ alkoxy, C$_{1-3}$ haloalkoxy, amino, C$_{1-3}$ alkylamino, di(C$_{1-3}$ alkyl) amino, carbamyl, C$_{1-3}$ alkylcarbamyl, and di(C$_{1-3}$ alkyl) carbamyl;
each R$^{13b}$ is independently selected from halo, CN, NO$_2$, C$_{1-6}$ alkyl, C$_{2-6}$ alkenyl, C$_{2-6}$ alkynyl, C$_{1-6}$ haloalkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$S(=O)R$^{b1}$, NR$^{c1}$S(=O)$_2$NR$^{c1}$R$^{d1}$, S(=O)R$^{b1}$, S(=O)$_2$R$^{b1}$, and S(=O)$_2$NR$^{c1}$R$^{d1}$; wherein said C$_{1-6}$ alkyl, C$_{2-6}$ alkenyl, C$_{2-6}$ alkynyl are each optionally substituted with 1, 2, or 3 independently selected R$^{11}$ groups;
each Cy is independently selected from C$_{3-7}$ cycloalkyl, 4-10 membered heterocycloalkyl, phenyl, and 5-10 membered heteroaryl, wherein said C$_{3-7}$ cycloalkyl, 4-10 membered heterocycloalkyl, phenyl, and 5-10 membered heteroaryl are optionally substituted with 1, 2, 3, or 4 independently selected R$^{13b}$ groups;
each R$^a$, R$^c$, and R$^d$ is independently selected from H, C$_{1-6}$ alkyl, C$_{1-6}$ haloalkyl, C$_{2-6}$ alkenyl, C$_{2-6}$ alkynyl, and Cy; wherein said C$_{1-6}$ alkyl, C$_{2-6}$ alkenyl, and C$_{2-6}$ alkynyl are each optionally substituted with 1, 2, or 3 independently selected R$^{13b}$ groups;

each $R^b$ is independently selected from $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{13b}$ groups; or each $R^{a1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups; and each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups.

2. A compound of claim 1, having Formula IV:

IV or a pharmaceutically acceptable salt thereof.

3. A compound of claim 1, having Formula IVa:

IVa or a pharmaceutically acceptable salt thereof.

4. A compound of claim 1, or a pharmaceutically acceptable salt thereof, wherein:

$R^1$ is methyl;
$R^4$ is $C_{1-4}$ alkyl, halo or CN;
$R^5$ is halo;
$R^6$ is H;
$R^{3b}$ is H, Cy, —($C_{1-3}$alkylene)-Cy, $C_{1-6}$ alkyl, $C_{1-6}$ haloalkyl, C(=O)$R^b$, C(=O)NR$^c$R$^d$, C(=O)OR$^a$, or S(=O)$_2$R$^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl, $C_{1-6}$ haloalkyl, and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, OR$^{a1}$, C(=O)R$^{b1}$, C(=O)NR$^{c1}$R$^{d1}$, C(=O)OR$^{a1}$, NR$^{c1}$C(=O)R$^{b1}$, S(=O)$_2$R$^{b1}$, and S(=O)$_2$NR$^{c1}$R$^{d1}$, wherein said $C_{1-6}$ alkyl is optionally substituted with 1, 2, or 3 independently selected $R^{11}$ groups;

each $R^{11}$ is independently selected from OH, CN, $C_{1-3}$ alkoxy, amino, $C_{1-3}$ alkylamino, di($C_{1-3}$ alkyl)amino, carbamyl, $C_{1-3}$ alkylcarbamyl, and di($C_{1-3}$ alkyl)carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

5. A compound of claim 1, having Formula IV:

IV or a pharmaceutically acceptable salt thereof, wherein:

V is CH$_2$;
$R^1$ is methyl;
$R^4$ is methyl, F or CN;
$R^5$ is Cl;
$R^6$ is H;
$R^{3b}$ is H, Cy, —($C_{1-3}$alkylene)-Cy, $C_{1-6}$ alkyl, $C_{1-6}$ haloalkyl, C(=O)$R^b$, C(=O)NR$^c$R$^d$, C(=O)OR$^a$, or S(=O)$_2$R$^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

6. A compound of claim 1, having Formula XXI:

XXI

[Structural formula]

or a pharmaceutically acceptable salt thereof, wherein:
$R^1$ is methyl;
$R^{3a}$ is methyl or ethyl;
$R^4$ is methyl, F or CN;
$R^5$ is Cl;
$R^6$ is H;
$R^{3b}$ is H, Cy, —($C_{1-3}$alkylene)-Cy, $C_{1-6}$ alkyl, $C_{1-6}$ haloalkyl, $C(=O)R^b$, $C(=O)NR^cR^d$, $C(=O)OR^a$, or $S(=O)_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, $C(=O)R^{b1}$, $C(=O)NR^{c1}R^{d1}$, $C(=O)OR^{a1}$, $NR^{c1}C(=O)R^{b1}$, $S(=O)_2R^{b1}$, and $S(=O)_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

7. A compound of claim 1, wherein said compound is selected from:

tert-Butyl 9-[1-(4-amino-3-methyl-1H-pyrazolo[3,4-d]pyrimidin-1-yl)ethyl]-7-chloro-6-methyl-2,3-dihydro-1,4-benzoxazepine-4(5H)-carboxylate;

1-[1-(7-Chloro-6-methyl-2,3,4,5-tetrahydro-1,4-benzoxazepin-9-yl)ethyl]-3-methyl-1H-pyrazolo[3,4-d]pyrimidin-4-amine;

tert-Butyl 3-[9-[1-(4-amino-3-methyl-1H-pyrazolo[3,4-d]pyrimidin-1-yl)ethyl]-7-chloro-6-methyl-2,3-dihydro-1,4-benzoxazepin-4(5H)-yl]azetidine-1-carboxylate;

1-{1-[4-(1-Acetylazetidin-3-yl)-7-chloro-6-methyl-2,3,4,5-tetrahydro-1,4-benzoxazepin-9-yl]ethyl}-3-methyl-1H-pyrazolo[3,4-d]pyrimidin-4-amine;

1-[1-(7-Chloro-4-cyclobutyl-6-methyl-2,3,4,5-tetrahydro-1,4-benzoxazepin-9-yl)ethyl]-3-methyl-1H-pyrazolo[3,4-d]pyrimidin-4-amine;

1-[1-(7-Chloro-4-cyclopentyl-6-methyl-2,3,4,5-tetrahydro-1,4-benzoxazepin-9-yl)ethyl]-3-methyl-1H-pyrazolo[3,4-d]pyrimidin-4-amine;

1-[1-(7-Chloro-4-cyclohexyl-6-methyl-2,3,4,5-tetrahydro-1,4-benzoxazepin-9-yl)ethyl]-3-methyl-1H-pyrazolo[3,4-d]pyrimidin-4-amine;

1-{1-[7-Chloro-4-(4-methoxycyclohexyl)-6-methyl-2,3,4,5-tetrahydro-1,4-benzoxazepin-9-yl]ethyl}-3-methyl-1H-pyrazolo[3,4-d]pyrimidin-4-amine;

1-[1-(7-Chloro-4,6-dimethyl-2,3,4,5-tetrahydro-1,4-benzoxazepin-9-yl)ethyl]-3-methyl-1H-pyrazolo[3,4-d]pyrimidin-4-amine;

1-[1-(7-Chloro-4-isopropyl-6-methyl-2,3,4,5-tetrahydro-1,4-benzoxazepin-9-yl)ethyl]-3-methyl-1H-pyrazolo[3,4-d]pyrimidin-4-amine;

[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]acetonitrile;

3-[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]-3-oxopropanenitrile;

1-{1-[7-Chloro-6-methyl-4-(methylsulfonyl)-2,3,4,5-tetrahydro-1,4-benzoxazepin-9-yl]ethyl}-3-methyl-1H-pyrazolo[3,4-d]pyrimidin-4-amine;

1-{1-[7-Chloro-6-methyl-4-(phenylsulfonyl)-2,3,4,5-tetrahydro-1,4-benzoxazepin-9-yl]ethyl}-3-methyl-1H-pyrazolo[3,4-d]pyrimidin-4-amine;

9-[1-(4-Amino-3-methyl-1H-pyrazolo[3,4-d]pyrimidin-1-yl)ethyl]-7-chloro-6-methyl-N-(2-methylphenyl)-2,3-dihydro-1,4-benzoxazepine-4(5H)-carboxamide;

1-[1-(4-Benzoyl-7-chloro-6-methyl-2,3,4,5-tetrahydro-1,4-benzoxazepin-9-yl)ethyl]-3-methyl-1H-pyrazolo[3,4-d]pyrimidin-4-amine;

1-(1-{7-Chloro-4-[(3,5-dimethylisoxazol-4-yl)sulfonyl]-6-methyl-2,3,4,5-tetrahydro-1,4-benzoxazepin-9-yl}ethyl)-3-methyl-1H-pyrazolo[3,4-d]pyrimidin-4-amine;

1-{1-[7-Chloro-4-(cyclopropylsulfonyl)-6-methyl-2,3,4,5-tetrahydro-1,4-benzoxazepin-9-yl]ethyl}-3-methyl-1H-pyrazolo[3,4-d]pyrimidin-4-amine;

1-[1-(4-Acetyl-7-chloro-6-methyl-2,3,4,5-tetrahydro-1,4-benzoxazepin-9-yl)ethyl]-3-methyl-1H-pyrazolo[3,4-d]pyrimidin-4-amine;

1-[1-(7-Chloro-6-methyl-4-propionyl-2,3,4,5-tetrahydro-1,4-benzoxazepin-9-yl)ethyl]-3-methyl-1H-pyrazolo[3,4-d]pyrimidin-4-amine;

1-{1-[7-Chloro-4-(methoxyacetyl)-6-methyl-2,3,4,5-tetrahydro-1,4-benzoxazepin-9-yl]ethyl}-3-methyl-1H-pyrazolo[3,4-d]pyrimidin-4-amine;

1-[1-(7-Chloro-4-isobutyryl-6-methyl-2,3,4,5-tetrahydro-1,4-benzoxazepin-9-yl)ethyl]-3-methyl-1H-pyrazolo[3,4-d]pyrimidin-4-amine;

2-[9-[1-(4-Amino-3-methyl-1H-pyrazolo[3,4-d]pyrimidin-1-yl)ethyl]-7-chloro-6-methyl-2,3-dihydro-1,4-benzoxazepin-4(5H)-yl]-1,3-thiazole-5-carbonitrile; and 1-[1-(7-Chloro-6-methyl-4-pyrazin-2-yl-2,3,4,5-tetrahydro-1,4-benzoxazepin-9-yl)ethyl]-3-methyl-1H-pyrazolo[3,4-d]pyrimidin-4-amine;

or a pharmaceutically acceptable salt of any of the aforementioned.

8. A compound of claim 1, selected from:

tert-Butyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate;

1-{1-[4-(1-Acetylazetidin-3-yl)-7-chloro-6-fluoro-2-methyl-2,3,4,5-tetrahydro-1,4-benzoxazepin-9-yl]ethyl}-3-methyl-1H-pyrazolo[3,4-d]pyrimidin-4-amine;

1-{1-[4-(1-Acetylazetidin-3-yl)-7-chloro-6-fluoro-2,3,4,5-tetrahydro-1,4-benzoxazepin-9-yl]ethyl}-3-methyl-1H-pyrazolo[3,4-d]pyrimidin-4-amine;

1-{1-[(3S)-7-Chloro-6-fluoro-3-methyl-4-(methylsulfonyl)-2,3,4,5-tetrahydro-1,4-benzoxazepin-9-yl]ethyl}-3-methyl-1H-pyrazolo[3,4-d]pyrimidin-4-amine;

1-{1-[7-Chloro-6-fluoro-2-methyl-4-(methylsulfonyl)-2,3,4,5-tetrahydro-1,4-benzoxazepin-9-yl]ethyl}-3-methyl-1H-pyrazolo[3,4-d]pyrimidin-4-amine;

3-[9-[1-(4-Amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]cyclobutanecarboxylic acid;

3-[(2S)-9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutanecarboxamide;

4-(1-Acetylazetidin-3-yl)-9-[1-(4-amino-3-methyl-1H-pyrazolo[3,4-d]pyrimidin-1-yl)ethyl]-7-chloro-2,3,4,5-tetrahydro-1,4-benzoxazepine-6-carbonitrile;

9-[1-(4-Amino-3-methyl-1H-pyrazolo[3,4-d]pyrimidin-1-yl)ethyl]-7-chloro-4-[1-(2-hydroxyethyl)azetidin-3-yl]-2,3,4,5-tetrahydro-1,4-benzoxazepine-6-carbonitrile;

4-(1-Acetylazetidin-3-yl)-9-[1-(4-amino-3-methyl-1H-pyrazolo[3,4-d]pyrimidin-1-yl)ethyl]-7-chloro-2-methyl-2,3,4,5-tetrahydro-1,4-benzoxazepine-6-carbonitrile;

2-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidin-1-yl}acetamide;

9-[1-(4-Amino-3-methyl-1H-pyrazolo[3,4-d]pyrimidin-1-yl)ethyl]-7-chloro-4-[1-(2-hydroxy-2-methylpropyl)azetidin-3-yl]-2-methyl-2,3,4,5-tetrahydro-1,4-benzoxazepine-6-carbonitrile;

(2S)-9-[1-(4-Amino-3-methyl-1H-pyrazolo[3,4-d]pyrimidin-1-yl)ethyl]-7-chloro-4-[1-(2-hydroxyethyl)azetidin-3-yl]-2-methyl-2,3,4,5-tetrahydro-1,4-benzoxazepine-6-carbonitrile;

9-[1-(4-Amino-3-methyl-1H-pyrazolo[3,4-d]pyrimidin-1-yl)ethyl]-7-chloro-4-(2-hydroxyethyl)-2,3,4,5-tetrahydro-1,4-benzoxazepine-6-carbonitrile;

9-[1-(4-Amino-3-methyl-1H-pyrazolo[3,4-d]pyrimidin-1-yl)ethyl]-7-chloro-2-methyl-4-(pyridin-3-ylmethyl)-2,3,4,5-tetrahydro-1,4-benzoxazepine-6-carbonitrile;

9-[1-(4-Amino-3-methyl-1H-pyrazolo[3,4-d]pyrimidin-1-yl)ethyl]-7-chloro-4-(2-hydroxyethyl)-2-methyl-2,3,4,5-tetrahydro-1,4-benzoxazepine-6-carbonitrile;

9-[1-(4-Amino-3-methyl-1H-pyrazolo[3,4-d]pyrimidin-1-yl)ethyl]-7-chloro-4-(2-hydroxy-2-methylpropyl)-2-methyl-2,3,4,5-tetrahydro-1,4-benzoxazepine-6-carbonitrile;

N-{3-[9-[1-(4-Amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]cyclobutyl}acetamide;

9-[1-(4-Amino-3-methyl-1H-pyrazolo[3,4-d]pyrimidin-1-yl)ethyl]-7-chloro-2-ethyl-4-(2-hydroxyethyl)-2,3,4,5-tetrahydro-1,4-benzoxazepine-6-carbonitrile;

3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]-N,N-dimethylazetidine-1-carboxamide;

3-[9-[1-(4-amino-3-methyl-1H-pyrazolo[3,4-d]pyrimidin-1-yl)ethyl]-7-chloro-6-fluoro-2,3-dihydro-1,4-benzoxazepin-4(5H)-yl]-N,N-dimethylazetidine-1-sulfonamide;

1-(1-{7-chloro-6-fluoro-2-methyl-4-[1-(methylsulfonyl)azetidin-3-yl]-2,3,4,5-tetrahydro-1,4-benzoxazepin-9-yl}ethyl)-3-methyl-1H-pyrazolo[3,4-d]pyrimidin-4-amine;

1-{1-[7-chloro-6-fluoro-2-methyl-4-(1-propionylazetidin-3-yl)-2,3,4,5-tetrahydro-1,4-benzoxazepin-9-yl]ethyl}-3-methyl-1H-pyrazolo[3,4-d]pyrimidin-4-amine;

(2R)-1-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]propan-2-ol;

methyl 3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxylate;

3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-sulfonamide;

3-[9-[1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidine-1-carboxamide;

(2S)-1-{3-[(2S)-9-[(1S)-1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidin-1-yl}propan-2-ol;

(2S)-1-{3-[(2S)-9-[(1S)-1-(4-amino-3-methyl-1H-pyrazolo[3,4-d]pyrimidin-1-yl)ethyl]-7-chloro-6-fluoro-2-methyl-2,3-dihydro-1,4-benzoxazepin-4(5H)-yl]azetidin-1-yl}propan-2-ol;

2-{3-[(2S)-9-[1-(4-amino-3-methyl-1H-pyrazolo[3,4-d] pyrimidin-1-yl)ethyl]-7-chloro-6-fluoro-2-methyl-2,3-dihydro-1,4-benzoxazepin-4(5H)-yl]azetidin-1-yl}acetamide;

9-[1-(4-amino-3-methyl-1H-pyrazolo[3,4-d]pyrimidin-1-yl)ethyl]-7-chloro-4-(1-propionylazetidin-3-yl)-2,3,4,5-tetrahydro-1,4-benzoxazepine-6-carbonitrile;

9-[1-(4-amino-3-methyl-1H-pyrazolo[3,4-d]pyrimidin-1-yl)ethyl]-7-chloro-4-[1-(methylsulfonyl)azetidin-3-yl]-2,3,4,5-tetrahydro-1,4-benzoxazepine-6-carbonitrile;

3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]-N-isopropylazetidine-1-carboxamide;

ethyl 3-[9-[1-(4-amino-3-methyl-1H-pyrazolo[3,4-d]pyrimidin-1-yl)ethyl]-7-chloro-6-cyano-2,3-dihydro-1,4-benzoxazepin-4(5H)-yl]azetidine-1-carboxylate;

9-[1-(4-amino-3-methyl-1H-pyrazolo[3,4-d]pyrimidin-1-yl)ethyl]-7-chloro-2-methyl-4-[1-(methylsulfonyl)azetidin-3-yl]-2,3,4,5-tetrahydro-1,4-benzoxazepine-6-carbonitrile;

9-[1-(4-amino-3-methyl-1H-pyrazolo[3,4-d]pyrimidin-1-yl)ethyl]-7-chloro-2-methyl-4-(1-propionylazetidin-3-yl)-2,3,4,5-tetrahydro-1,4-benzoxazepine-6-carbonitrile;

3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-ethylazetidine-1-carboxamide;

ethyl 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]azetidine-1-carboxylate;

3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-isopropylazetidine-1-carboxamide;

9-[1-(4-amino-3-methyl-1H-pyrazolo[3,4-d]pyrimidin-1-yl)ethyl]-7-chloro-4-[1-(2-hydroxyethyl)azetidin-3-yl]-2-methyl-2,3,4,5-tetrahydro-1,4-benzoxazepine-6-carbonitrile;

3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N,N-dimethylazetidine-1-sulfonamide;

9-[1-(4-amino-3-methyl-1H-pyrazolo[3,4-d]pyrimidin-1-yl)ethyl]-7-chloro-4-(cyanomethyl)-2-methyl-2,3,4,5-tetrahydro-1,4-benzoxazepine-6-carbonitrile;

2-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]acetamide;

9-[1-(4-amino-3-methyl-1H-pyrazolo[3,4-d]pyrimidin-1-yl)ethyl]-7-chloro-4-(2-methoxyethyl)-2-methyl-2,3,4,5-tetrahydro-1,4-benzoxazepine-6-carbonitrile; and 3-[9-[1-(4-amino-3-methyl-1H-pyrazolo[3,4-d]pyrimidin-1-yl)ethyl]-7-chloro-6-cyano-2-methyl-2,3-dihydro-1,4-benzoxazepin-4(5H)-yl]-N-methylcyclobutanecarboxamide;

or a pharmaceutically acceptable salt of any of the aforementioned.

9. A pharmaceutical composition comprising a compound of claim 1, or a pharmaceutically acceptable salt thereof, and at least one pharmaceutically acceptable carrier.

10. A compound of claim 1, or a pharmaceutically acceptable salt thereof, wherein $R^1$ is methyl.

11. A compound of claim 1, or a pharmaceutically acceptable salt thereof, wherein $R^4$ is $C_{1-4}$ alkyl, halo or CN.

12. A compound of claim 1, or a pharmaceutically acceptable salt thereof, wherein $R^4$ is methyl, F, or CN.

13. A compound of claim 1, or a pharmaceutically acceptable salt thereof, wherein $R^5$ is halo.

14. A compound of claim 1, or a pharmaceutically acceptable salt thereof, wherein $R^5$ is chloro.

15. A compound of claim 1, or a pharmaceutically acceptable salt thereof, wherein $R^{3b}$ is H, Cy, —($C_{1-3}$alkylene)-Cy, $C_{1-6}$ alkyl, $C_{1-6}$ haloalkyl, C(=O)$R^b$, C(=O)NR$^c$R$^d$, C(=O)OR$^a$, or S(=O)$_2$R$^b$, wherein said $C_{1-6}$ alkyl is optionally substituted by 1, 2, 3, or 4 independently selected $R^{13b}$ groups.

16. A compound of claim 1, or a pharmaceutically acceptable salt thereof, wherein each $R^a$, $R^b$, $R^c$, and $R^d$ is independently selected from $C_{1-6}$ alkyl, $C_{1-6}$ haloalkyl, and Cy; wherein said $C_{1-6}$ alkyl are each optionally substituted with 1, 2, or 3 independently selected $R^{13b}$ groups.

17. A compound of claim 1, or a pharmaceutically acceptable salt thereof, wherein each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups.

18. A compound of claim 1, or a pharmaceutically acceptable salt thereof, wherein each $R^{13b}$ is independently selected from CN, $C_{1-6}$ alkyl, $C_{1-6}$ haloalkyl, OR$^{a1}$, C(=O)R$^{b1}$, or C(=O)OR$^{a1}$.

19. A compound of claim 1, or a pharmaceutically acceptable salt thereof, wherein each $R^{13b}$ is independently selected from CN, $C_{1-6}$ alkyl, $C_{1-6}$ haloalkyl, OR$^{a1}$, C(=O)R$^{b1}$, C(=O)NR$^{c1}$R$^{d1}$, C(=O)OR$^{a1}$, NR$^{c1}$C(=O)R$^{b1}$, S(=O)$_2$R$^{b1}$, and S(=O)$_2$NR$^{c1}$R$^{d1}$, wherein said $C_{1-6}$ alkyl is optionally substituted with 1, 2, or 3 independently selected $R^{11}$ groups.

20. A compound of claim 1, or a pharmaceutically acceptable salt thereof, wherein each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

21. A compound of claim 1, or a pharmaceutically acceptable salt thereof, wherein each $R^{11}$ is independently selected from OH, CN, $C_{1-3}$ alkoxy, amino, $C_{1-3}$ alkylamino, di($C_{1-3}$alkyl)amino, carbamyl, $C_{1-3}$alkylcarbamyl, and di($C_{1-3}$alkyl)carbamyl.

22. A compound of claim 1, or a pharmaceutically acceptable salt thereof, wherein each $R^{11}$ is independently selected from OH and carbamyl.

23. A compound of claim 1, having Formula XXII:

XXII or a pharmaceutically acceptable salt thereof, wherein:

$R^1$ is methyl;

$R^{3a}$ is methyl;

$R^4$ is methyl, F or CN;

$R^5$ is Cl;

$R^6$ is H;

$R^{3b}$ is H, Cy, —($C_{1-3}$alkylene)-Cy, $C_{1-6}$ alkyl, $C_{1-6}$ haloalkyl, C(=O)$R^b$, C(=O)$NR^cR^d$, C(=O)$OR^a$, or S(=O)$_2R^b$, wherein said $C_{1-6}$ alkyl is optionally substituted by 1, 2, 3, or 4 independently selected $R^{13b}$ groups;

each $R^a$, $R^b$, $R^c$, and $R^d$ is independently selected from $C_{1-6}$ alkyl and Cy; wherein said $C_{1-6}$ alkyl is optionally substituted with 1, 2, or 3 independently selected $R^{13b}$ groups;

each Cy is independently selected from monocyclic $C_{3-7}$ cycloalkyl, monocyclic 4-7 membered heterocycloalkyl, phenyl, and monocyclic 5-6 membered heteroaryl, wherein said monocyclic $C_{3-7}$ cycloalkyl, monocyclic 4-7 membered heterocycloalkyl, phenyl, and monocyclic 5-6 membered heteroaryl are optionally substituted with 1, 2, 3, or 4 independently selected $R^{13b}$ groups;

each $R^{13b}$ is independently selected from CN, $C_{1-6}$ alkyl, $C_{1-6}$ haloalkyl, $OR^{a1}$, C(=O)$R^{b1}$, C(=O)$NR^{c1}R^{d1}$, C(=O)$OR^{a1}$, $NR^{c1}$C(=O)$R^{b1}$, S(=O)$_2R^{b1}$, and S(=O)$_2NR^{c1}R^{d1}$, wherein said $C_{1-6}$ alkyl is optionally substituted with 1 or 2 independently selected $R^{11}$ groups;

each $R^{11}$ is independently selected from OH and carbamyl;

each $R^{a1}$, $R^{c1}$, and $R^{d1}$ is independently selected from H, $C_{1-6}$ alkyl, and $C_{1-6}$ haloalkyl; and each $R^{b1}$ is independently selected from $C_{1-6}$ alkyl and $C_{1-6}$ haloalkyl.

24. A method of treating B cell lymphoma in a patient, comprising administering to said patient a therapeutically effective amount of a compound of claim 1, or a pharmaceutically acceptable salt thereof.

25. A method of treating diffuse large B cell lymphoma in a patient, comprising administering to said patient a therapeutically effective amount of a compound of claim 1, or a pharmaceutically acceptable salt thereof.

26. A method of treating chronic lymphocytic leukemia in a patient, comprising administering to said patient a therapeutically effective amount of a compound of claim 1, or a pharmaceutically acceptable salt thereof.

27. A method of treating follicular B-cell Non-Hodgkin lymphoma in a patient, comprising administering to said patient a therapeutically effective amount of a compound of claim 1, or a pharmaceutically acceptable salt thereof.

28. A method of treating small lymphocytic lymphoma in a patient, comprising administering to said patient a therapeutically effective amount of a compound of claim 1, or a pharmaceutically acceptable salt thereof.

29. A method of treating Non-Hodgkin lymphoma in a patient, comprising administering to said patient a therapeutically effective amount of a compound of claim 1, or a pharmaceutically acceptable salt thereof.

* * * * *